United States Patent
Pinyayev et al.

(10) Patent No.: US 8,214,958 B2
(45) Date of Patent: Jul. 10, 2012

(54) SENSOR RESPONSIVE ELECTRIC TOOTHBRUSHES AND METHODS OF USE

(75) Inventors: Aleksey Mikhailovich Pinyayev, West Chester, OH (US); Eric Altman Goulbourne, Jr., Hamilton, OH (US); Stephen Andras Kovacs, Loveland, OH (US); Chanchal Kumar Ghosh, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 267 days.

(21) Appl. No.: 11/899,657

(22) Filed: Sep. 7, 2007

(65) Prior Publication Data

US 2008/0060148 A1    Mar. 13, 2008

(51) Int. Cl.
*A61C 3/00* (2006.01)
(52) U.S. Cl. .......................................... 15/22.1
(58) Field of Classification Search ............... 15/167.1, 15/21.1, 22.1; 433/29
See application file for complete search history.

(56) References Cited

U.S. PATENT DOCUMENTS

| | | | |
|---|---|---|---|
| 4,066,745 A | 1/1978 | Tomlinson | |
| 5,082,444 A | 1/1992 | Rhoades | |
| 5,281,363 A | 1/1994 | Shacklette | |
| 5,376,006 A | 12/1994 | Fischer | |
| 5,378,403 A | 1/1995 | Shacklette | |
| 5,493,747 A | 2/1996 | Inakagata et al. | |
| 5,546,624 A * | 8/1996 | Bock .............................. | 15/22.1 |
| 5,617,601 A | 4/1997 | McDougall | |
| 5,645,428 A | 7/1997 | Yarborough | |
| 5,662,833 A | 9/1997 | Laakso | |
| 5,713,738 A | 2/1998 | Yarborough | |
| 5,846,058 A | 12/1998 | Fischer | |
| 5,866,043 A | 2/1999 | Ikkala | |
| 5,894,620 A * | 4/1999 | Polaert et al. .................. | 15/22.1 |
| 5,958,303 A | 9/1999 | Narkis | |
| 6,000,083 A | 12/1999 | Blaustein | |
| 6,030,550 A | 2/2000 | Angelopoulos | |
| 6,214,320 B1 | 4/2001 | Gaffar | |
| 6,287,120 B1 | 9/2001 | Wiesel | |
| 6,343,932 B1 | 2/2002 | Wiesel | |
| 6,360,395 B2 | 3/2002 | Blaustein | |

(Continued)

FOREIGN PATENT DOCUMENTS

DE    4032779 A1    4/1992

(Continued)

OTHER PUBLICATIONS

International Search Report for PCT/US2005/008050 dated Nov. 17, 2005; 4 pages.

(Continued)

*Primary Examiner* — Laura C Guidotti
(74) *Attorney, Agent, or Firm* — John P. Colbert; George H. Leal; Vladimir Vittenberg

(57) ABSTRACT

A sensor-responsive toothbrush that can adjust its output or operation depending upon information received by one or more sensors incorporated in the toothbrush or as selected by a user. The information typically relates to certain conditions or the presence of particular substances or agents within or outside of the oral cavity. The sensor-responsive toothbrush also includes one or more responsive output components that provide a responsive output in response to the sensed information. A method of providing an oral care benefit, comprising steps of: activating a toothbrush comprising a sensor; detecting a sensor input with the sensor; and initiating a responsive output from the toothbrush in response to the sensor input.

6 Claims, 19 Drawing Sheets

U.S. PATENT DOCUMENTS

| | | | |
|---|---|---|---|
| 6,375,459 B1 * | 4/2002 | Kamen et al. | 433/80 |
| 6,447,757 B1 | 9/2002 | Orlowski | |
| 6,485,300 B1 * | 11/2002 | Muller et al. | 433/29 |
| 6,521,215 B2 | 2/2003 | Okay | |
| 6,533,582 B2 | 3/2003 | Lindquist | |
| 6,555,020 B1 | 4/2003 | Chadwick | |
| 6,558,654 B2 | 5/2003 | McLaughlin | |
| 6,611,780 B2 | 8/2003 | Lundell | |
| 6,646,540 B1 | 11/2003 | Lussey | |
| 6,648,904 B2 | 11/2003 | Altshuler | |
| 6,685,921 B2 | 2/2004 | Lawlor | |
| 6,725,490 B2 | 4/2004 | Blaustein | |
| 6,892,413 B2 | 5/2005 | Blaustein | |
| 6,951,463 B2 | 10/2005 | Masuhara | |
| 6,964,569 B2 | 11/2005 | Nordmo | |
| 7,013,522 B2 | 3/2006 | Kumagai | |
| 7,025,950 B2 | 4/2006 | Majeti | |
| 7,223,270 B2 | 5/2007 | Altshuler | |
| 7,223,281 B2 | 5/2007 | Altshuler | |
| 7,240,390 B2 | 7/2007 | Pfenniger | |
| 7,329,274 B2 | 2/2008 | Altshuler | |
| 7,354,448 B2 | 4/2008 | Altshuler | |
| 7,422,598 B2 | 9/2008 | Altshuler | |
| 7,748,070 B2 | 7/2010 | Chan | |
| 7,845,039 B2 | 12/2010 | Chan | |
| 2003/0084525 A1 | 5/2003 | Blaustein | |
| 2003/0084526 A1 | 5/2003 | Brown | |
| 2003/0163881 A1 | 9/2003 | Driesen | |
| 2003/0194678 A1 | 10/2003 | Viltro | |
| 2004/0060138 A1 | 4/2004 | Pfenniger | |
| 2004/0191729 A1 * | 9/2004 | Altshuler et al. | 433/215 |
| 2004/0199227 A1 | 10/2004 | Altshuler et al. | |
| 2005/0050659 A1 | 3/2005 | Chan | |
| 2005/0053895 A1 | 3/2005 | Pinyayev | |
| 2005/0053896 A1 | 3/2005 | Pinyayev | |
| 2005/0053898 A1 | 3/2005 | Ghosh | |
| 2005/0066459 A1 | 3/2005 | Pinyayev | |
| 2007/0298370 A1 | 12/2007 | Pinyayev | |
| 2007/0298371 A1 | 12/2007 | Pinyayev | |
| 2007/0298372 A1 | 12/2007 | Pinyayev | |
| 2008/0072389 A1 | 3/2008 | Ghosh | |

FOREIGN PATENT DOCUMENTS

| | | |
|---|---|---|
| DE | 10224043 A1 | 12/2003 |
| EP | 1104669 | 6/2001 |
| JP | 2003-093416 | 4/2003 |
| JP | 2004-065838 | 3/2004 |
| RU | 2033235 | 4/1995 |
| RU | 2089083 | 9/1997 |
| WO | WO 03/063722 | 8/2003 |
| WO | WO 2005/023131 | 3/2005 |
| WO | WO 2005/023143 | 3/2005 |
| WO | WO 2005/023144 | 3/2005 |
| WO | WO 2005/023145 | 3/2005 |
| WO | WO 2005/023146 | 3/2005 |

OTHER PUBLICATIONS

Written Opinion for PCT/US2005/008050 dated Nov. 17, 2005; 6 pages.

* cited by examiner

SENSOR RESPONSIVE ELECTRIC TOOTHBRUSHES AND METHODS OF USE

CROSS REFERENCE TO RELATED APPLICATIONS

This application claims the benefit of PCT US 2005/008050, filed on Mar. 9, 2005, incorporated herein by reference.

FIELD OF THE INVENTION

The present invention relates to sensor-responsive toothbrushes that utilize one or more sensors for detecting certain conditions or the presence of certain agents in the oral cavity and which can provide one or more responsive outputs. The present invention also relates to responsive toothbrushes which can provide one or more user selectable responsive outputs.

SUMMARY OF THE INVENTION

In a first aspect, the present invention provides a method for providing an oral care benefit comprising brushing the teeth with a toothbrush comprising a sensor. The method also comprises detecting a sensor input with the sensor. And, the method comprises initiating an output from the toothbrush in response to the sensor input.

In another aspect, the present invention provides a sensor responsive electric toothbrush comprising a handle, a head, and a neck extending between the handle and the head. The handle includes a hollow interior region. The head has bristles disposed thereon. And the toothbrush defines a longitudinal axis. The toothbrush additionally includes a sensor filter. And, the toothbrush comprises one or more movable bristle holders disposed on the head. The holders have a collection of bristles disposed thereon. The toothbrush also comprises a motor disposed in the hollow region which is operatively connected to the bristle holders by a drive shaft.

In yet another aspect, the present invention provides a sensor-responsive toothbrush comprising a body including a handle, a head, and a plurality of bristles disposed on the head. The toothbrush also comprises at least one sensor disposed on the body. And, the toothbrush comprises at least one output component in association with the sensor. The output is adapted to provide in response to the at least one sensor, at least one of (i0 a mechanical output, (ii) a light-based output, (iii) a chemical-based output and (iv) combinations thereof.

BRIEF DESCRIPTION OF THE DRAWINGS

The invention may take physical form in certain parts and arrangements of parts, embodiments of which will be described in detail in this specification and illustrated in the accompanying drawings which form a part hereof, and wherein.

DETAILED DESCRIPTION OF THE EMBODIMENTS

Figure 1:
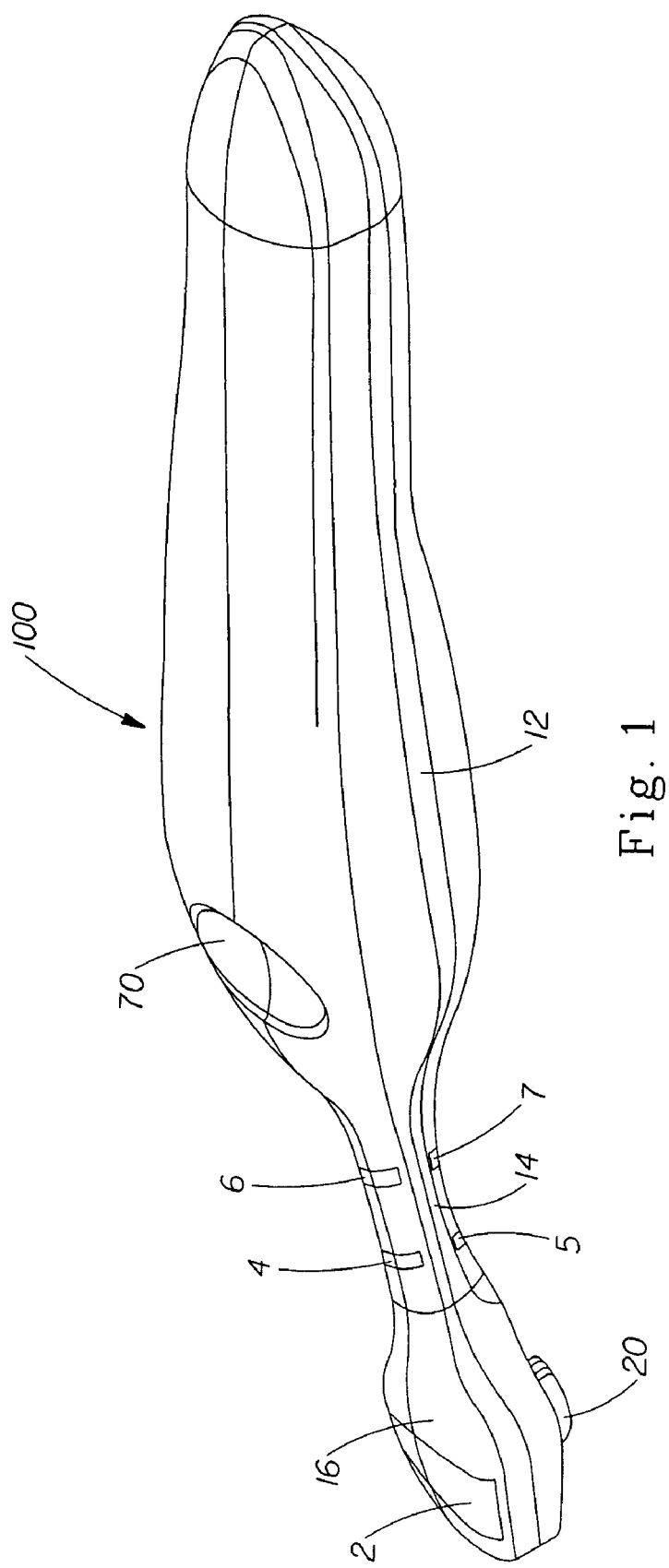
FIG. 1 is a perspective view of an embodiment of an electric toothbrush in accordance with the present invention.

Generally, the present invention relates to sensor-responsive toothbrushes. The toothbrushes comprise one or more sensors to detect particular conditions or the existence of certain agents in the oral cavity. The toothbrushes further comprise one or more components, assemblies, or systems that produce an output or combination of outputs to treat the detected conditions or agents based upon information obtained from the sensor(s).

Before describing the various embodiments of the present invention, it is instructive to describe various terms used herein. The term "toothbrush output" or "responsive output" is used to refer to an action initiated by the toothbrush in response to one or more markers, conditions, stimuli, or agents detected by the brush or in response to programmable or manually selectable responsive outputs designated by a user or the manufacturer of the toothbrush. Examples of such responsive outputs include mechanical outputs, energy based outputs (e.g., light, heat, or acoustic energy), chemical-based outputs, or any combinations of these outputs. The responsive output may be the initiation of the responsive output or a change in an already existing output of the toothbrush. Non-limiting examples of mechanical outputs include but are not limited to a movement or change in movement of the bristles or bristle holders, dispensing of a composition, generation of vibration of the toothbrush or components thereof, or a combination of these. An example of a change in motion of a movable bristle holder refers for example to the bristle holder changing direction of rotation, and can change in type of motion (i.e. rocking, reciprocating, oscillating, rotating), increase or decrease in speed. Another example of a mechanical output is moving or operating movable bristles or bristle carriers on the toothbrush at prescribed frequencies or patterns of motion. An example of a change in an energy-based responsive output may be an increase in the intensity of a light output. An example of a chemical output is the release or administration of one or more substances, compositions, or agents from the toothbrush. An example of a combination of these outputs is the emission of light and release of a dentifrice composition from the toothbrush. Each of these types of outputs are described in greater detail herein. A "responsive output element" is an assembly or structure that provides the responsive output. For example, a light source that emits light having a wavelength suitable for killing bacteria may be considered a responsive output element.

The one or more sensors utilized in the present invention toothbrushes include one or more sensor input elements and can optionally include one or more sensor output elements associated therewith. The term "sensor" refers to a device, component, or assembly that detects a condition, marker, or stimulus, typically found within the oral cavity although the detection may occur outside of the oral cavity. The detection can occur during the brushing process or upon activation of the toothbrush. Activation of the toothbrush can include, for example, turning the toothbrush on to initiate motion of the bristle holders, removing the toothbrush from a recharging stand, or other step that prepares the toothbrush for use (e.g., pushing a button that provides a signal to the toothbrush that it is about to be used). The condition may also include nature of a user's brushing habits (e.g., how long and when a user brushes) or the date/time of use where the responsive output has been selected by a user to occur at particular times/days of use. Generally the sensors as used herein provide a signal that provides information as to the detected condition, marker, or stimulus. The sensors of the present may be electrically powered and are therefore in electrical communication with a power source, such as one or more disposable or rechargeable batteries.

A "sensor input element" or "sensor input component" refers to an element on the toothbrush that detects or senses a condition, marker, or stimulus, such as the presence of a substance, material, or agent found within the oral cavity and/or which detects a user's brushing habits such as how often, when and how long a user brushes. As explained below, the sensor input element can operate in conjunction with a sensor output element to detect or sense a condition, marker, or stimulus within the oral cavity. However, the sensor input element may detect information from the oral cavity without the presence of a sensor output element. For example, the sensor input element may detect a tissue or dental surface color or a chemical in the mouth without the presence of a sensor output element. The sensor input element and the sensor output element are sometimes collectively referred to herein as "sensor." Examples of sensor input elements include light sensors (for detecting bacteria or caries), malodor sensors that can detect the presence of certain chemical compounds or agents, current or voltage sensors (for detecting brushing habits), and clock where the sensor input is the day and/or time of use. While the sensor input element may be located on the toothbrush head in most instances, it is contemplated that the sensor input element may be located elsewhere, such as the handle, based on the size of the sensor. For instance, a malodor sensor might be located in the handle due to its size. A "sensor output element" or "sensor output component" refers to an element on the toothbrush which can provide an output (e.g., light, heat, chemicals etc.) into the oral cavity that can interact with the condition, marker or stimulus so that the latter may be detected by the sensor input element. For example, light in the 655-740 nanometer wavelength, 1 mW intensity can be used to fluoresce caries in a manner that may be detectable by a sensor input element. A light source emitting light for this purpose would be considered a sensor output element. Alternatively, the combination of a chemical and light emission can be used to fluoresce bacteria in a manner that can be detected by a sensor input element. It is also contemplated that a sensor output element may provide a dual function, such as functioning as a sensor output element and providing a responsive output. For example, a light source might be used in combination with a sensor input element to detect bacteria and then the light source could provide a responsive output (e.g., changing the power output to kill the bacteria) in response to the detection of bacteria by the sensor input element. Sensors can also provide the user with a variety of other information, such as, sensing and alerting a user when a treatment session is complete, when the toothbrush is properly positioned, when the toothbrush is in contact with tissue, and/or if the temperature in the treatment area rises above a predetermined level. Sensors can also be used with a controller to provide automatic feedback control of a treatment session(s). In one embodiment, a controller is coupled with a diagnostic sensor to control a light or heat source based on signals from the sensor. In another optional embodiment, a controller could be combined with a sensor to emit light or heat only when the toothbrush is in contact with tissue. The sensor may simply comprise a sensor input element that detects when, how often, and/or how long a user brushes and initiates a responsive output based upon the user's brushing habits. For example, a responsive output may be a change in the motion of the bristle holders for a user who brushes less frequently or automatic application of a light based responsive output to kill bacteria more aggressively.

The sensor input and sensor output elements can be placed anywhere on the toothbrush, the head, the handle etc. The responsive output component or element can be placed anywhere on the toothbrush which allows for access to the oral cavity. Fiber optics can be used to transfer certain qualities of light to the different areas of the oral cavity.

An example of a commercially available light sensor, which may be suitable for use as a sensor input element for detecting bacteria or caries, and one which converts detected light to a signal of varying voltage is a light-to-voltage sensor available from TAOS, Inc., of Plano, Tex. under the designation No. TSL12S. A sensor filter may also be used in conjunction with this light sensor to facilitate the detection. An example of a commercially available sensor filter is a long wavelength pass filter that can be used in conjunction with a light sensor. The long wavelength pass filter is available from Gentex Corporation of Carbondale, Pa. A under the designation Filtron E780.

As described herein, the various preferred embodiment toothbrushes provide one or more responsive outputs (including adjustments of one or more existing outputs of the toothbrush) in response to detection of particular conditions or presence of markers, conditions, stimuli, substances, materials, or agents within the oral cavity. The responsive output can treat, remedy or partially remedy the detected conditions or presence of agents. The present invention toothbrush is not limited to such actions however. That is, the present invention includes embodiments in which the toothbrush responsive output(s) do not immediately treat or remedy the detected conditions or presence of agents. For example, the responsive outputs can exhibit a delayed effect or only a partial effect. The responsive output(s) may also form part of a long term treatment regime that may occur over a period of weeks or months depending on brushing frequency. The treatment regime may be user selected following detection of the marker, condition, or stimuli by the sensor input element or may be initiated and tracked by a controller (e.g., a programmable processor containing a clock) that can track when and/or how long a user brushes and provide a responsive output treatment regime tailored to a user's brushing habits. Moreover, the responsive outputs can operate to address a secondary factor in the detected condition or agents. Furthermore, the outputs can be designated as part of a treatment regime for an entirely different malady than that directly responsible for the detected conditions or agents.

Another aspect of the present invention includes embodiments of the toothbrushes that await for selection or input from the user prior to adjusting their operation. That is, a semi-automatic mode of operation is contemplated in which the responsive output of the toothbrush depends, in whole or at least in part, upon parameters or selection of parameters from the user. Examples of such parameters include, but are not limited to, (i) the time frame or duration for performing the output, (ii) the manner in which the output is performed, (iii) where multiple outputs are possible, the selection of one or more of these outputs, and (iv) combinations of these scenarios.

The present invention toothbrushes encompass a wide array of variant embodiments. For example, the toothbrush output may be of limited duration. Or, for a light-based output toothbrush, the tissues of the oral cavity may be exposed to only light of a particular wavelength, i.e. red light, for less than some prescribed period of time, such as a minute (e.g., for bacteria kill).

The toothbrush can be used to detect and treat caries, cavities, oral malodor, whiten teeth, bacteria in the oral cavity, tartar, plaque, and a combination of these things. The toothbrush can be an AM/PM brush (which may be programmable) which can sense or undertake certain treatments depending on the time of day, as selected by a user or programmed by the manufacturer. A user may program the toothbrush via an interface, which can include for example a display and one or more input buttons, located on the handle or, if the electric toothbrush is rechargeable, via an interface located on the rechargeable stand that receives the electric toothbrush for recharging. For example, the toothbrush can be configured to provide a responsive output for malodor or plaque/tartar in the morning and a responsive output for whitening teeth or treating caries in the evening. These responsive outputs can be provided either automatically upon detection of a marker, condition, or stimulus by a sensor input element or selectably based upon user inputs via the interface. For example, a user may select which condition is treated in the morning versus the evening. The toothbrush can utilize a date and time clock to track the time and/or date and then activate certain sensors and/or responsive outputs depending on the time of day and/or date. For instance, a sensor input element may be activated in the morning to detect malodor for a user who selects malodor treatment in the morning, or a responsive output for malodor may be provided automatically in the morning. A timer can be used to set the length of a treatment regimen automatically or the length of a treatment regimen can be selected by user via interface. The clock and/or timer may be linked to or form part of a control board (e.g., a circuit board, programmable controller, microprocessor or the like) which then activates the desired sensors and/or responsive outputs depending on the time of day and/or date.

The toothbrush can optionally include a removable head that uses certain sensors and output emitters on various interchangeable heads. For example, such a toothbrush can include a tooth whitening head and its associated sensor(s) and responsive output element(s) and a separate antibacterial head. The controller may be programmed to detect which head is attached to the toothbrush handle and adjust the toothbrush operation accordingly. For example, the controller may alter the motion of the bristle holders or may process the electrical signals from the sensor using algorithms associated with the particular sensor attached to the toothbrush.

The sensor-responsive toothbrushes can also comprise one or more alarms or signaling devices (e.g., a speaker or light source) to indicate for example (i) the beginning, progress, or completion of a particular treatment regime or process, (ii) sensing or detecting of certain markers, conditions, stimuli, the presence (or absence) of certain chemicals in the oral cavity, or (iv) combinations of these. The alarms or signals can also be configured to indicate initiation of a particular responsive output by the toothbrush. The alarms or signals can be in the form of auditory, visual, or tactile signals. Tactile signals may include vibration or other motion of certain parts of the toothbrush, for example the handle or the moving bristle holders. Examples of auditory alarms include, but are not limited to one or more beeps, a series of notes, a song of portion thereof, one or more tones, one or more rings, and combinations of these. It is also contemplated that the toothbrush could utilize an auditory alarm that generates prerecorded spoken words or phrases. Non-limiting examples of visual alarms or signals include emitting light in which the emission is in the form of a graphic symbol, picture, text or other indicia on the toothbrush. Additionally, signaling or alarming can be accomplished by changing color of a signal light on the toothbrush. Also, it may in certain versions of the sensor-responsive toothbrush, be preferred to indicate a state, such as initiation or completion of an output by a combination of (i) auditory signals, (ii) visual signals, and (iii) tactile signals.

A. Responsive Mechanical Outputs

The present invention toothbrushes can utilize one or more responsive mechanical outputs. As noted, non-limiting examples of such outputs can include inducing movement or changes in movement of bristles, bristle holders or bristle carriers, or other movable components on the toothbrush. Mechanical responsive outputs may be initiated in response the detection of a variety of markers, conditions, stimuli, or agents inside or outside the oral cavity. For example, a mechanical responsive output may be provided in response to detection of bacteria or caries by a sensor input element or based upon a user's brushing habits.

The head includes a longitudinal axis, one or more moving bristle holders or carriers and, optionally, one or more static or fixed bristle holders. The moving bristle holders may rotate, swivel, gyrate, oscillate, linearly reciprocate, or undergo any combination of motions. The type of motion provided by the electric toothbrushes of the present invention can be widely varied. The static bristle holders and the arrangement of the static bristles disposed thereon can also be widely varied. For example, the static bristles might partially or wholly circumscribe the moving bristle holders or may be disposed in a gap between the moving bristle holders. Examples of some bristle holder motions and bristle arrangements suitable for use with the present invention are described in US 20030126699; US 20030084525; US 20030084524; US 20030084526; and WO 03/063723; and WO 03/063722. The bristles can be made from conventional non-elastomeric materials, such as polyethylene, or can be made from elastomeric materials such as natural or synthetic rubbers, polyolefins, polyetheramides, polyesters, styrenic polymers, polyurethanes, etc., or a combination of materials.

The handle has a hollow portion with a motor disposed therein that is operably connected to the moving bristle holders. A shaft extends from the motor through the neck and into at least a portion of the head. The shaft may rotate, oscillate, linearly reciprocate, gyrate, orbit, or move in a conical fashion when driven by the motor in order to impart one or more motions to the moving bristle holders. A gearing arrangement can be provided between the motor and the shaft or between the shaft and the moving bristle holders in order to impart the motion thereto. Exemplary shaft and/or gearing arrangements are shown in U.S. Pat. Nos. 6,360,395 and 5,617,601, and U.S. Patent Application Nos. 2003/0134567 and 2003/0163881 as well as in other patents and patent publications referenced herein. The handle also has a power source, such as one or more batteries, disposed therein for powering the motor and the light-emitting elements. Alternatively, the electric toothbrush may be connected to an external power source for powering the motor. A switch is disposed on the handle for activating the motor and/or light-emitting elements. The switch includes an actuator button and a metal contact. The switch is manually depressed by pressing a molded actuator button down, which presses against a metal contact, completing the circuit, as in a conventional momentary switch. The switch allows continuous operation, through a ramp design, by depressing and sliding the actuator button forward as in a conventional continuous switch. By combining these two functions in one switch, the consumer can try the unit and see its operation prior to purchase, and still operate it continuously once out of the package. The switch can also activate one or more light-emitting elements. The light-emitting elements are energized whenever the motor is activated, however, the electric toothbrush can also have a switch designated to activate the light-emitting element.

Details of various preferred assemblies, components, and configurations for the mechanical outputs are provided in the descriptions of light-based outputs and chemical-based outputs set forth herein.

The sensor-responsive toothbrushes can include vibrating mechanisms, such as mechanical or ultrasonic vibrators, to promote mechanical cleaning. The vibrations generated by the vibrator can be employed not only for better tooth cleaning but also for enhancing phototherapy. For example, the vibrations can increase light penetration into soft tissue and/or increase the effect of light treatment on cells and/or bacteria. One mechanism of such enhancements is better oxygen delivery to a phototreated target.

B. Light-Based Responsive Outputs

Preferred embodiment toothbrushes comprising one or more light-based responsive outputs can include one or more electrically powered elements disposed on the head including, but not limited to, light-emitting diodes (LEDs), light-emitting elements using incandescent elements, laser elements, halogen elements, neon elements, fluorescent elements, plasma elements, xenon elements, and combinations thereof. The present invention includes a wide array of oral care implements such as, but are not limited to, electric toothbrushes, powered flossers, tooth polishers, gum massagers, etc. For simplicity's sake the invention shall be referred to as a sensor responsive electric toothbrush.

As used herein, the term "light" is intended to encompass the spectrum of both visible and non-visible (e.g., ultraviolet and infra-red) light. In one embodiment of the toothbrush of the present invention the light emitted from the light-emitting element can be from about 370, 390, 410, 430, 450, 470, 490, 510, 530, 550, 570, 590, 610, 630, 650, 670, 690, 710 nm and/or less than about 770, 750, 730, 710, 690, 670, 650, 630, 610, 500, 400 nm. In another embodiment the light emitted can have a wavelength of greater than about 420, 430, 440, 450, 460, 470, 480, and/or 490 nm and/or less than about 490, 480, 470, 460, 450, 440, 430 nm. In yet another embodiment the light emitted can have a wave length from about 420, 430, 440, 450, 460, 470 nm and/or less than about 470, 460, 450, 430 nm. It will be appreciated that the particular range of wavelengths selected can depend upon the desired color of the light. In one embodiment the light emitted can be a blue color. The oral care implement can also emit light of a particular intensity. Intensity can be either luminous intensity measured in candelas (or lumens/steradian), or flux density measured in Watts/meter$^2$. In one embodiment the flux density of the inventive illuminated electric toothbrush is from about 20, 30, 35, 40, 45, 50, 55, 60, 70, 100, 200, 250 mW/cm$^2$ and/or less than about 300, 250, 200, 150, 100, 70, 60, 50, 40, 30 mW/cm$^2$ or any combination of these.

Typically, the light-based outputs emit light for a prescribed period of time. For example, light can be used which has 632-904 nanometer wavelength, 5-10 mW intensity for 0.5 to 2 minutes with compositions toluidine blue and methylene blue (blue, red and purple dyes from phenylmethane family) which can be used to generate radicals that may be effective at killing bacteria and other agents. Thus, a toothbrush of the present invention can be provided with a light source that emits light having a wavelength between about 632-904 nanometers upon the detection of bacteria by a sensor input element or based upon a selected regime as previously described. Toluidine blue or methylene blue may be provided in the dentifrice used with the toothbrush or dispensed by the toothbrush as described more fully hereafter. Other responsive agents can be included in the dentifrice or dispensed which are responsive (e.g., are activated or otherwise interact with the responsive output) to other light based responsive outputs or other responsive outputs, such as heat. The dentifrice may contain one or more of these responsive agents that may remain inactive until activated by a responsive output from the toothbrush. Other responsive agents are described throughout the application hereafter and it will be appreciated that these may be incorporated individually or combined in dentifrices suitable for use with the present invention. Where the various responsive agents are incorporated separately within the dentifrice, it is contemplated that a signal may be provided to the user regarding which dentifrice to use based upon the detection of a condition, marker, or stimuli and a determination which responsive agent is best suited for use with a responsive output associated with the detected condition, marker, or stimuli. In order to maintain a current list of manufactured dentifrices and their responsive agents as well as well as provide data necessary for providing new responsive outputs or regimens for the toothbrush and/or new replaceable toothbrush heads as technology and the understanding of oral health progress, it is contemplated that the recharging stands for toothbrushes of the present invention may be connected to a computer network, such as the Internet, to facilitate the downloading of dentifrice, responsive output, or regimen data for use by the toothbrush. The responsive agents may be dispensed alone or in combination from the toothbrushes of the present invention. Other light based responsive agents for killing bacteria may include riboflavin (vitamin B2) in combination with light having a wavelength between about 430 nm, chlorophyll in combination with light having a wavelength about 440 nm, or other radical generating agents such as hydrogen peroxide, urea peroxide, percarbonate and the like at a variety of wavelengths. Metals such as silver, iron, and manganese may be responsive agents if the wavelength of the light results in heat generation that can kill bacteria. Light having a wavelength between about 380 nm and about 420 nm may be effective at killing bacteria without the use of a responsive agent.

In one embodiment, the electric toothbrush includes an elongated body portion or handle, a head, and a neck extending between the head and the handle. One or more light-emitting elements can be provided on the head, adjacent to, on, or in one or more static or moving bristle holders having a plurality of bristles thereon. The bristles may be formed into one or more groups or tufts. In certain embodiments, a light-emitting element can be positioned at the center or at the axis of movement of an oscillating bristle holder. Additionally, the light-emitting element can act as the pin which serves as the axis and/or center of rotation for the movable bristle holder. The light-emitting element can be stationary, or it can be secured to the movable bristle holder so that the element moves with the bristle holder. The bristle holder can, in certain embodiments, feature a region, such as an aperture, which promotes the passage of light there through. That region may be formed from a transparent or translucent material, or alternatively, the region can be an aperture or other open area substantially free of bristles thereby permitting the passage of light. This region can be provided at any portion of the head of the toothbrush, including the center of a movable bristle holder.

Referring now to the drawings wherein the showings are for the purposes of illustrating the embodiments of the invention only and not for purposes of limiting same, FIG. 1 shows a sensor responsive illuminated electric toothbrush 100 according to one embodiment of the present invention. The electric toothbrush can be used for personal hygiene such as brushing one's teeth and gums. As shown in FIG. 1, the electric toothbrush includes a handle 12 and a neck 14 attached to the handle 12. A head 16 is attached to neck 14. Typically, the head is larger than the neck 14, which is also typically smaller than the handle 12. The toothbrush 100 comprises one or more sensor elements or components 2, 4, 5, 6, and 7. One or more of these elements can be sensor input elements or one or more can be optional sensor output elements. Although the toothbrush 100 is shown with particular locations for these elements, it will be appreciated that the sensor elements can be disposed at different locations on the toothbrush 100.

Figure 2:
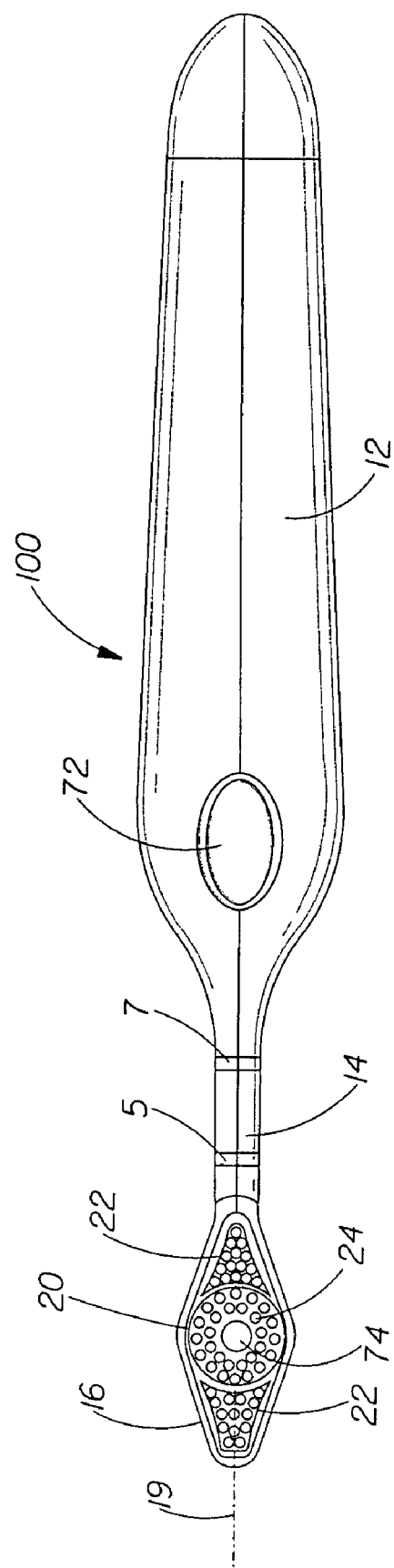
FIG. 2 is a top planar view of the electric toothbrush of FIG. 1.

Referring now to FIG. 2, the head 16 further is defined by a longitudinal axis 19, and comprises a moving bristle holder 20 and one or more optional static bristle holders 22. In this embodiment the static bristle holders 22 are located on opposite sides of the moving bristle holder 20. The moving bristle holder 20 in this embodiment is located at the center of the head 16. The moving bristle holder 20 includes a plurality of bristles 24 supported and retained on the holder 20. The moving bristle holder can oscillate or rotate about an axis of motion approximately normal to the longitudinal axis 19 of the head 16, although other motions may be provided as previously described. As described in greater detail herein, disposed along this axis of motion of the moving bristle holder, is an electrically powered element. In a particular embodiment (as shown in FIG. 2), the electrically powered element is a light-emitting element 75 such as a light-emitting diode positioned on the head of the toothbrush and generally below or under where the surface of the light-emitting element does not extend beyond the bristle bearing surface of the moving bristle holder. This embodiment of the toothbrush also has gripping portions 70 and 72.

Figure 3:
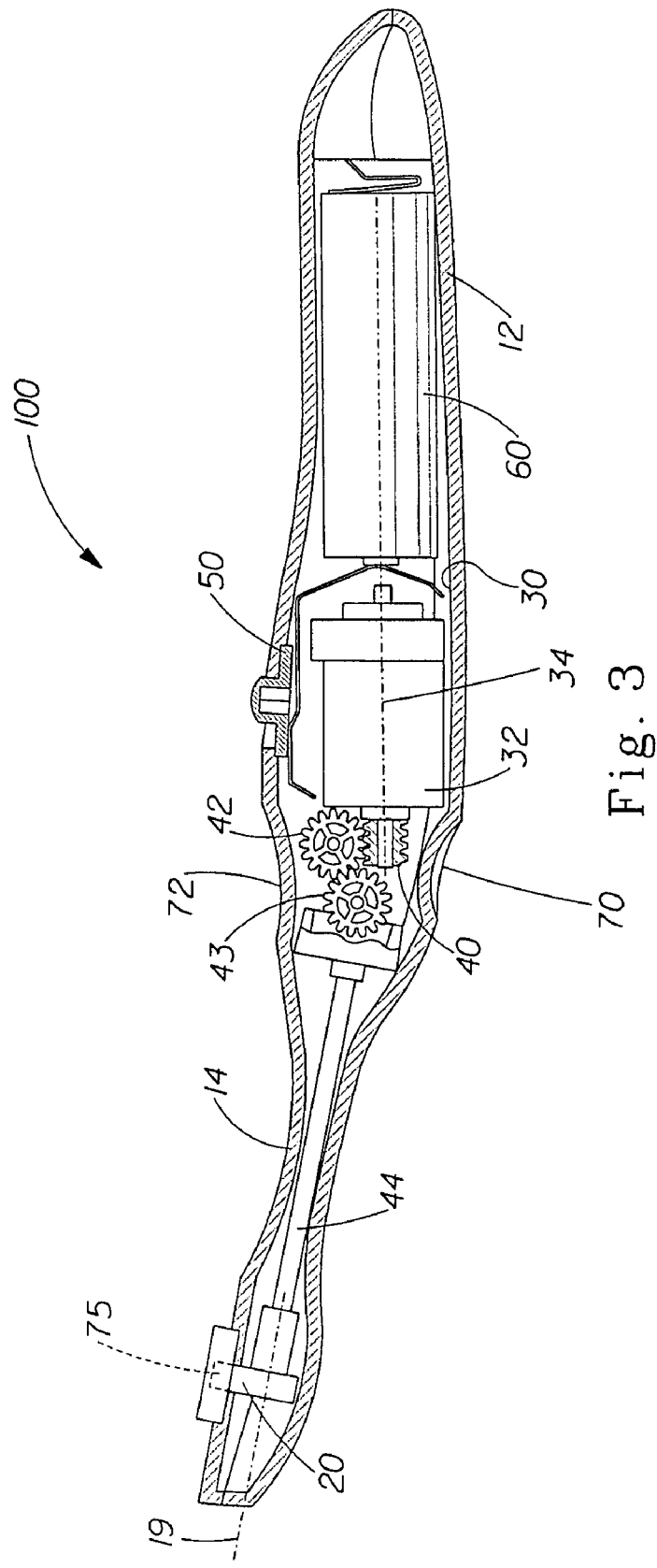
FIG. 3 is a cross-sectional side elevational view of the electric toothbrush of FIG. 1.

As shown in FIG. 3, the handle 12 further includes a hollow portion 30 which houses a motor 32, and has a longitudinal axis 34. The motor 32 powers the moving bristle holder 20 through a rotatable shaft 44. A gearing arrangement is operatively interconnected between the shaft 44 and the motor 32. The gearing arrangement includes a worm gear 40 and a pair of step gears 42, 43. The motor 32 is operatively connected to the worm gear 40. Step gear 42 is operatively connected to step gear 43 and the worm gear 40. A light-emitting element 75 is provided that is disposed in the interior of the moving bristle holder 20. As used herein, the term "light-emitting" element is intended to refer to an element that converts electrical energy into light, as opposed to an element that merely conducts or transmits light, such as a fiber optic cable or wire. However, in certain embodiments, the present invention toothbrushes providing a light-based output can utilize fiber optic cable or wire to emit light from the toothbrush. In one embodiment the light-emitting element of the present invention is a light-emitting diode or LED.

For light-emitting diodes, the dominant or central wavelength can determined by the equations:

$$\lambda_c = \int_{\lambda min}^{\lambda max} I(\lambda) \cdot \lambda \cdot d\lambda \bigg/ \int_{\lambda min}^{\lambda max} I(\lambda) \cdot d\lambda$$

For continuous spectrums, and $$\lambda_c = \sum_i I_i \lambda_i \bigg/ \sum_i I_i$$

For discrete spectrums.

Wherein I is illumination intensity and λ is wavelength.

These equations are further described in CIE 127 (1997) entitled "Measurement of LEDs", which is published by the International Commission of Illumination. These equations and methodology can be also be applied to light-emitting elements other than LEDs, or other methodologies and equations known in the art can be utilized to determine the dominant or central wavelength of a light-emitting element. The spectral (e.g., peak wavelength), photometric (e.g., luminous intensity), radiometric (e.g., radiant intensity), and colormetric (e.g., dominant wavelength) characteristics of the light-emitting elements can be measured using devices known in the art, such as OL 730CV Radiometer/Photometer manufactured by Optronic Laboratories, Inc. of Orlando, Fla. Some light may not have a dominant or central wavelength (e.g., white light).

Figure 4:
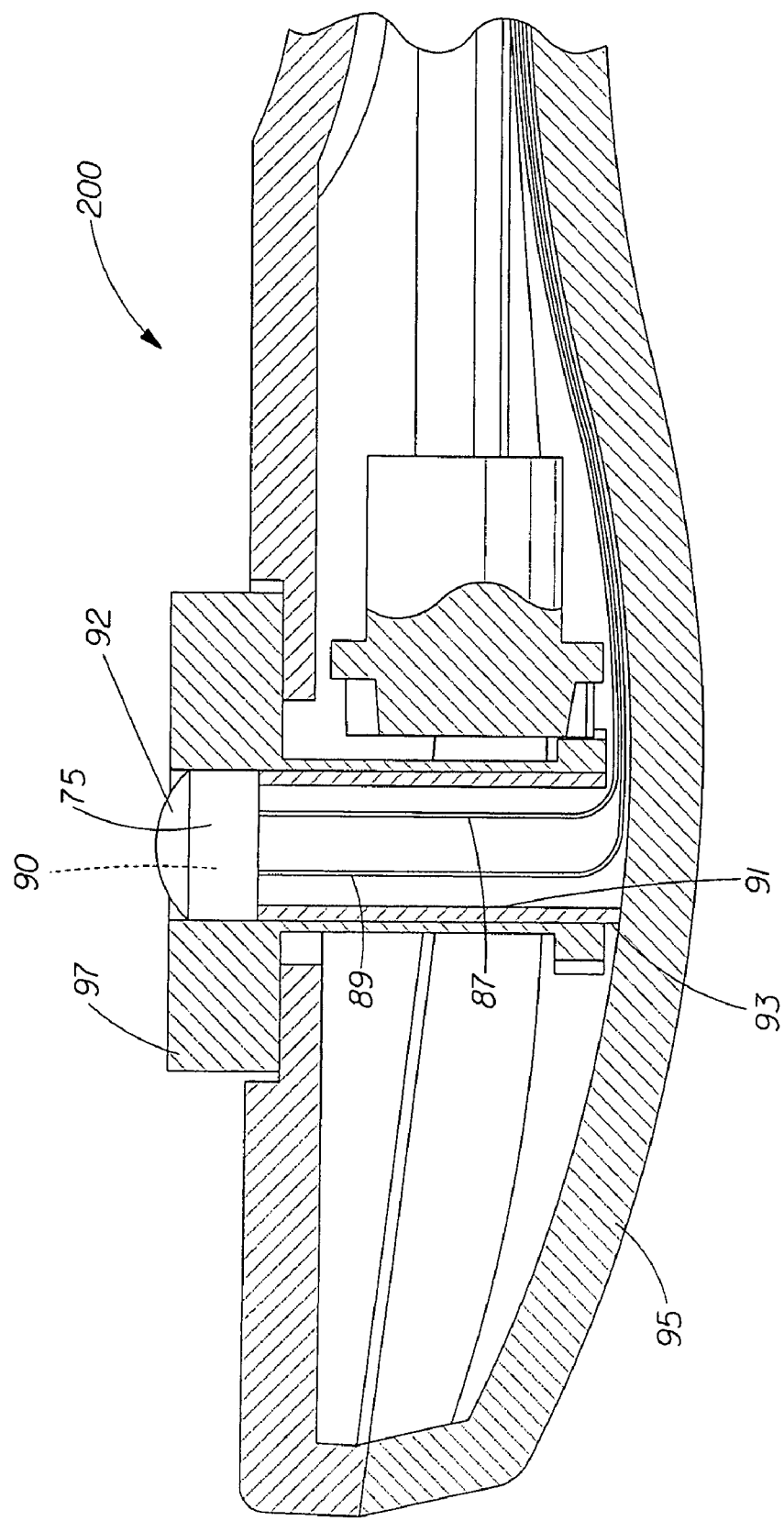
FIG. 4 is a cross-sectional side view of a head and neck of an embodiment of an electric toothbrush according to the present invention.

FIG. 4 illustrates an embodiment of a toothbrush 200 having a stationary light-emitting element 75 that is connected to and/or disposed within a pillar 91 that is stationary and fixed to the head 95 at point 93 of the toothbrush. In this embodiment the moving bristle holder 97 oscillates or rotates around the stationary light-emitting element 75 disposed within pillar 91. This light-emitting element 75 disposed within the pillar 91 serves as the axis of rotation for the moving bristle holder 97 on the head 95 of the toothbrush. The positive lead 87 and the negative lead 89 can run from the light-emitting element 75 through the pillar 91 and then down the length of the head 95 and neck (not shown) of the toothbrush to the power source (not shown).

Figures 5, 6:
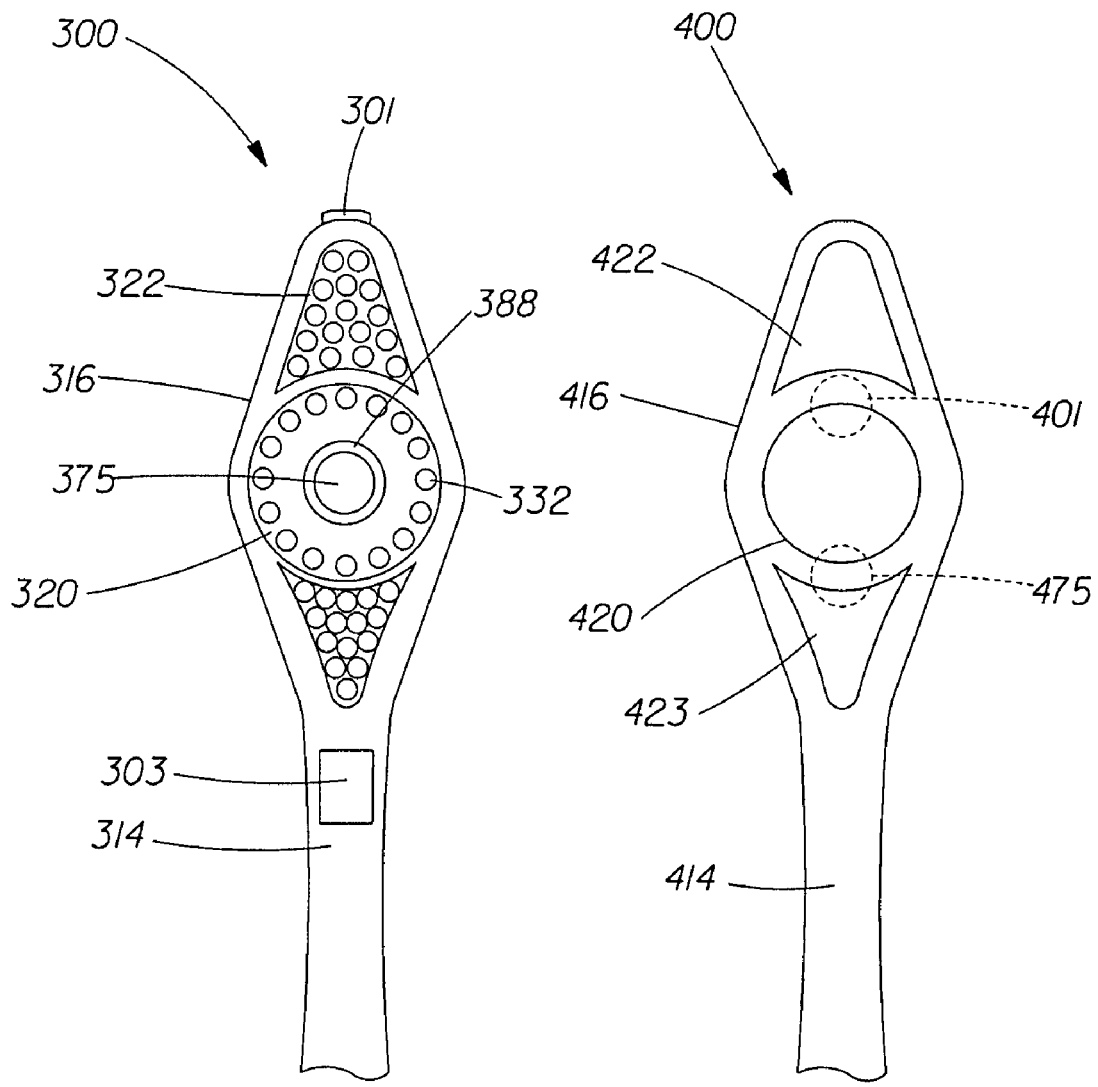
FIG. 5 is a partial front elevational view of a head and neck of another embodiment of the present invention.
FIG. 6 is a partial front elevational view of a head and neck of yet another embodiment of the present invention.

In another embodiment, a light-emitting element 375 of a toothbrush 300 is disposed within an aperture or hole 388 that extends through a moving bristle holder 320, as best seen in FIG. 5, so that the light-emitting element is stationary and the moving bristle holder 320 oscillates or rotates about the stationary light-emitting element 375. The toothbrush 300 also comprises one or more sensors such as 301 and 303. In this embodiment, the light-emitting element 375 is fixedly secured to the head 316. The light-emitting element 375 might extend partially through the hole 388 or it may be disposed below the lower surface of the moving bristle holder 320 so that it is completely contained within the head 316. The centerline or axis of the light-emitting element 375 may also be the axis of rotation or oscillation for the moving bristle holder 320. In some of the above-described embodiments, particularly where the light-emitting element is disposed below the movable bristle holder 320, the moving bristle holder can be formed from a transparent or translucent material. When the light-emitting element is disposed within the head, the light-emitting element may be placed so that it is between bristle holders and not aligned with an axis of rotation/oscillation of a moving bristle holder, as shown by way of example in FIG. 6, wherein the bristles have been deleted for clarity. FIG. 6 illustrates a toothbrush 400 comprising a head 416, a neck 414, a movable bristle holder 420, static bristle holder 422 and 423, one or more sensors such as 401, and a light-emitting element 475. The sensor(s) 401 and the light-emitting element 475 are disposed underneath the movable bristle holder 420 and the static bristle holder 423. In this embodiment, the top surface of the head and the bristle holders may be formed from a transparent or translucent material.

A variety of materials may be used for forming a transparent or translucent bristle holder and/or head. Examples of such materials include, but are not limited to, polystyrene (PS), polycarbonate (PC), polymethyl methacrylate (PMMA), polyethylene terephthalate glycol (PETG) (commercially available under the designation Eastoman BR003), cellulose acetate propylate (CAP), and combinations thereof. It is contemplated that one or more thermal treatments may be employed to facilitate processing of these materials.

The light-emitting elements can be arranged so that the principle direction of light emission is generally perpendicular to the top surface of the bristle holders and/or generally parallel to the direction of the bristles of the bristle holder. In other words, the light-emitting element can be arranged so that the centerline 90 of the light-emitting element is generally perpendicular to the top surface of the head and/or bristle holder, as best seen in FIG. 4. The centerline 90 typically passes through the lens 92 or aperture of the light-emitting element. When the light-emitting element is disposed within, on, or below a moving and/or static bristle holder, a cylindrical region or volume about the centerline 90 of the light-emitting element can be devoid of bristles so that light is transmitted to the brushing surface without interference from the bristles. In one embodiment the diameter of the cylindrical volume that is devoid of bristles is between about 2 mm and about 8 mm, in another embodiment between about 3 mm and about 6 mm. The moving bristle holder still, however, can have at least one ring of bristles that encircle the light-emitting element, as shown by way of example in FIG. 5. Additional bristle tufts or an inner ring of bristle tufts might, however, be provided.

Referring again to FIG. 3, a switch 50 is provided to control operation of the sensor responsive illuminated electric toothbrush and is operatively connected to the motor 32. The switch 50 is also configured to operate the sensing and control circuits and to optionally operate one or more lighting elements of the toothbrush. Such operation can be momentary or continuous and can be independent of the operation of the light-based output(s). That is, the present invention toothbrushes include embodiments in which the light-based outputs are activated by the sensing circuit(s) of the toothbrush, or by a user.

The two modes of activation can be independent of one another. When the switch 50 is closed, a circuit is completed between a battery 60 provided within the hollow portion 30 of the handle 10 and the motor 32 and lighting element 75.

Figure 7:
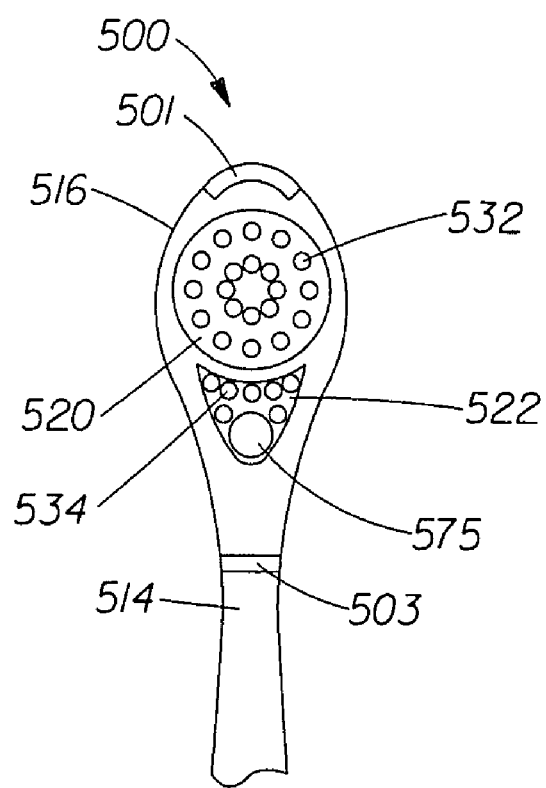
FIG. 7 is a partial front elevational view of a head and neck of still another embodiment of the present invention.
Figure 8:
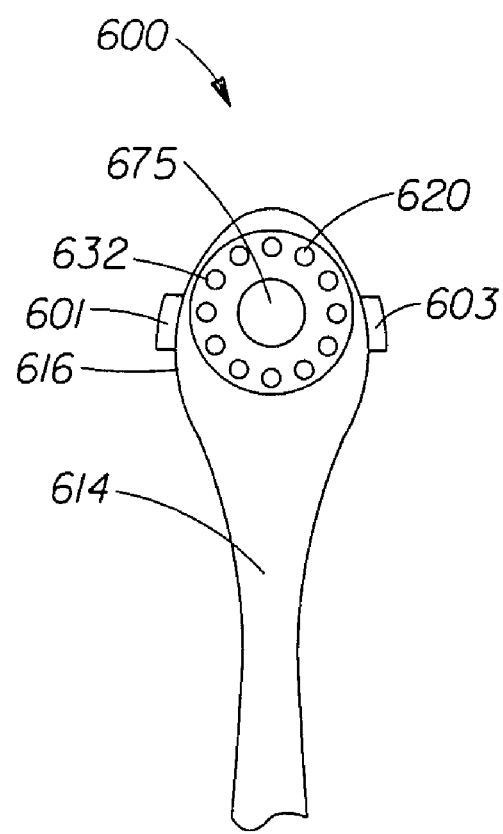
FIG. 8 is a partial front elevational view of a head and neck of yet another embodiment of the present invention.
Figure 9:
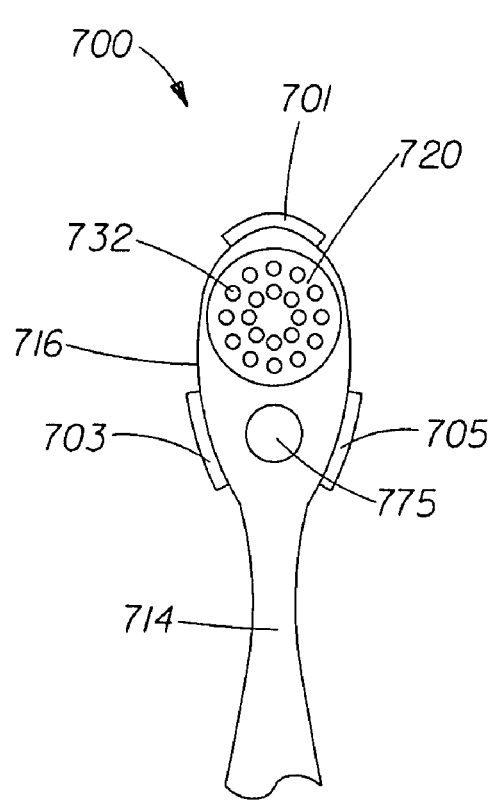
FIG. 9 is a partial front elevational view of a head and neck of yet another embodiment of the present invention.
Figure 10:
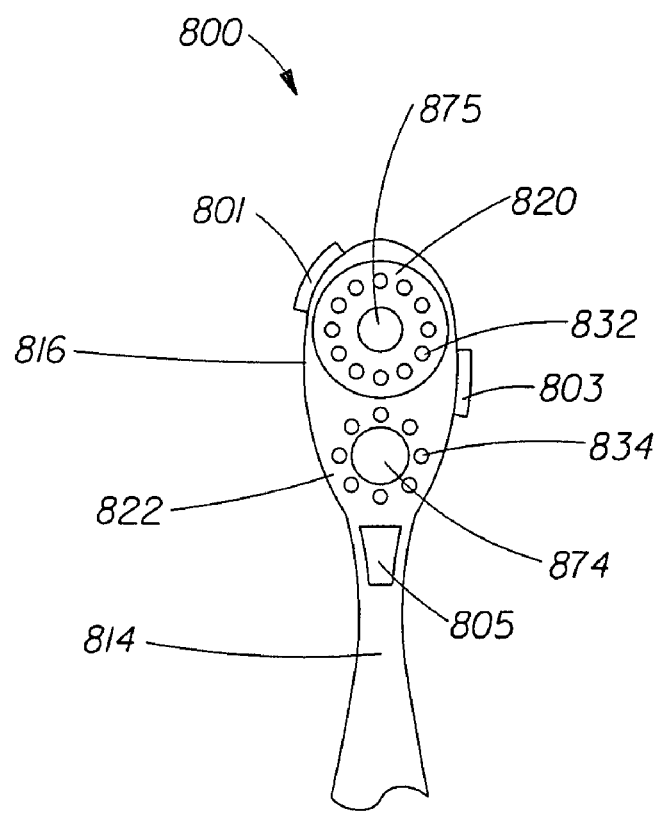
FIG. 10 is a partial front elevational view of a head and neck of still another embodiment of the present invention.

FIGS. 7-10 illustrate other head, bristle holder and bristle configurations for sensor responsive illuminated electric toothbrushes, all of which contain one or more light-emitting elements. FIG. 7 illustrates a toothbrush 500 comprising a head 516 and a neck 514. The toothbrush also comprises sensors 501 and 503, such as the previously described light sensor and/or filter. It will be appreciated that the neck 514 extends between the head 516 and a handle of the toothbrush (not shown). Disposed on the head 516 is a single moving bristle holder 520 having a plurality of bristles tufts 532 disposed thereon. Disposed on a second bristle holder 522 is a light-emitting element 575. FIG. 8 depicts another embodiment toothbrush 600 comprising a head 616 and neck 614 and sensors 601 and 603 in accordance with the present invention. The head 616 comprises a single bristle holder 620 comprising bristles 632, and having a light-emitting element 675 disposed therein. FIG. 9 depicts yet another toothbrush 700 including a head 716 having a single bristle holder 720 disposed thereon and a neck 714. The toothbrush 700 comprises one or more sensors such as sensors 701, 703, and 705. A light-emitting element 775 is disposed adjacent the bristle holder 720 on the head 716. The light-emitting element 775, however, is not disposed on bristle holder. FIG. 10 depicts still another toothbrush 800 comprising a head 816 having a first bristle holder 820 that moves, a second bristle holder 822 that is fixed or stationary, and a neck 814 connected to the head 816. The toothbrush 800 includes sensors 801, 803, and 805. Both bristle holders have light-emitting elements 875 disposed thereon. The first bristle holder 820 has a plurality of bristle tufts 832 that encircle the light-emitting element 875 disposed thereon, and the second bristle holder 822 has a plurality of bristle tufts 834 that encircle the light-emitting element 874 disposed thereon.

Figure 11:
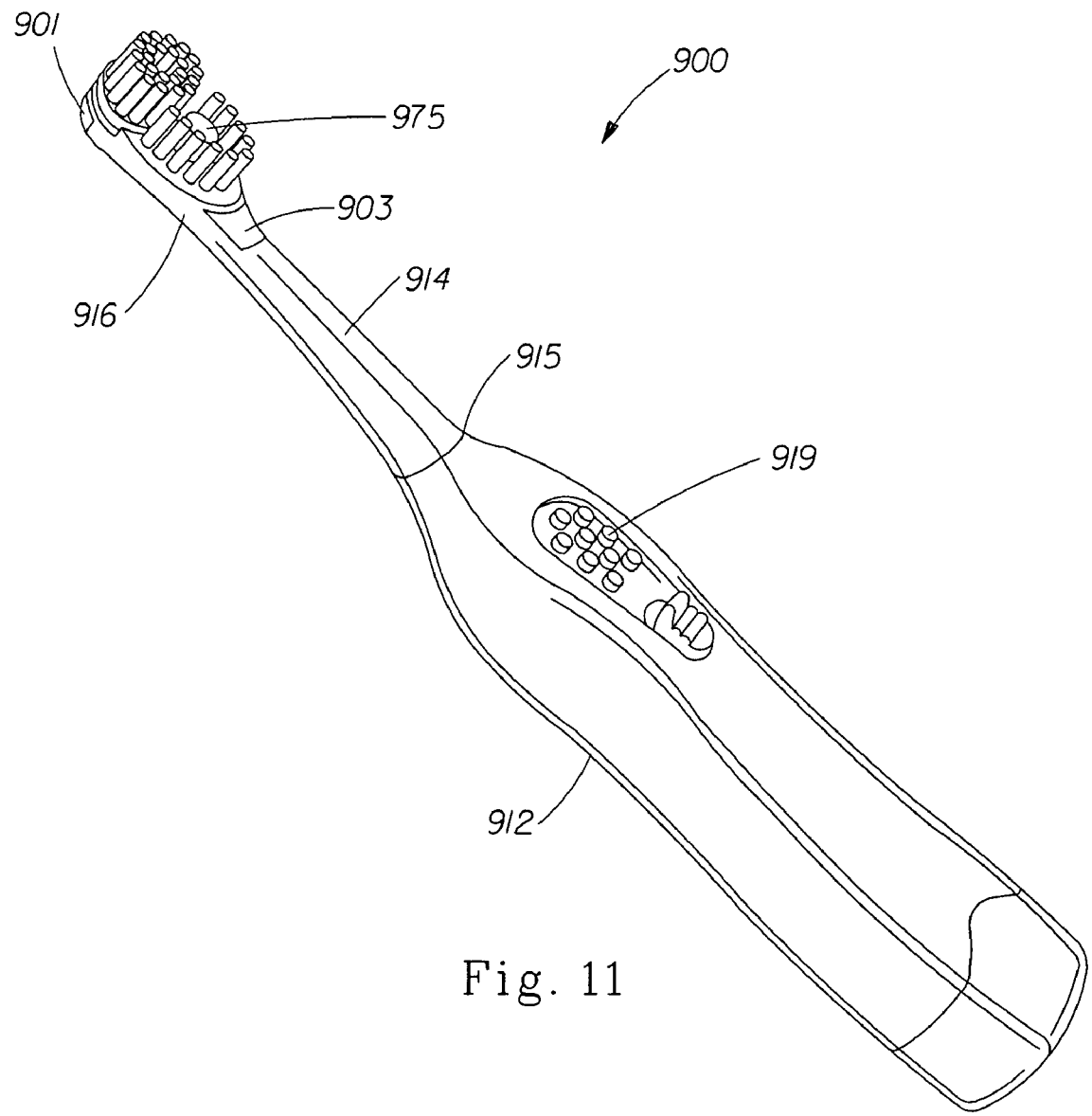
FIG. 11 is a perspective view of another embodiment of the electric toothbrush of the present invention in which the toothbrush includes a head and neck that can be separated from the handle.

Another embodiment of an electric toothbrush 900 according to the present invention is shown in FIG. 11, having a head 916, neck 914, and a handle 912. The toothbrush 900 comprises sensors 901 and 903. Disposed on the head 916 is a light-emitting element 975. The neck and handle are releasably connected at 915 and contain corresponding structures for their physical engagement and for establishing electrical communication between the lighting-emitting element and the power source. This embodiment of the invention also comprises a gripping portion 919.

A wide variety of light-emitting elements may be used with the present invention. In one embodiment the lighting-emitting element is a small, low power consumption, light-emitting diode (LED) such as those commercially available under the designation Luxeon™ manufactured by Lumileds Lighting, LLC of San Jose Calif. Other commercially available lighting units include those from American Opto Plus LED Corporation. The LED can operate from a relatively low voltage DC power supply, such as in one embodiment between about 0.5 volt and about 5 volts, an in another embodiment between about 1 volt and 3 volts, and in another embodiment between about 1.6 to about 2.4 volts.

In other embodiments, the light radiation source is solid-state lighting (SSL) including a light-emitting diode (LED) and LED variations, such as, edge emitting LED (EELED), surface emitting LED (SELED) or high brightness LED (HBLED). The LED can be based on different materials such as AlInGaN/AlN (emitting from 285 nm), SiC, AlInGaN, GaAs, AlGaAs, GaN, InGaN, AlGaN, AlIn—GaN, BaN, InBaN, AlGaInP (emitting in NIR and IR), etc. LEDs also include organic LEDs which are constructed with a polymer as the active material and which have a broad spectrum of emission. The radiation source can be an LED such as shaping of LED dies, LED with transparent confinement region, photonics crystal structure, or resonant-cavity light-emitting diodes (RCLED).

Other possibilities include a superluminescent diode (SLD) or LED which preferably can provide a broad emission spectrum source. In addition, laser diode (LD), waveguide laser diode (WGLD), and a vertical cavity surface emitting laser (VCSEL) can also be utilized. The same materials used for LED's can be used for diode lasers. Other possibilities include a fiber laser (FL) with laser diode pumping. Fluorescence solid-state light source (FLS) with electro or light pumping from LD, LED or current/voltage sources can also be the radiation source. The FLS can be an organic fiber with electrical pumping.

Lamps such as incandescent lamps, fluorescent lamps, micro halide lamps or other suitable lamps may also be used with the present invention. A lamp can provide the radiation source for white, red, NIR and IR irradiation. For the 5-100 micron range, quantum cascade lasers (QCL) or far infrared emitting diodes can be used. One skilled in the art will appreciate that a variety of radiation sources can provide the necessary optical radiation for the sensor-responsive toothbrush depending on size, power requirements, desired treatment regimen, and combinations thereof.

The various embodiment toothbrushes described herein may utilize lighting-emitting elements having a variety of characteristics. Generally, the electric toothbrushes described herein utilizing light-based outputs can emit light having a central wave length between about 10 nm and about $10^6$ nm, and in one embodiment from about 390 nm to about 770 nm, and in another embodiment from about 420 nm to about 490 nm, and for a blue light between about 420 nm and about 470 nm.

Figure 12:
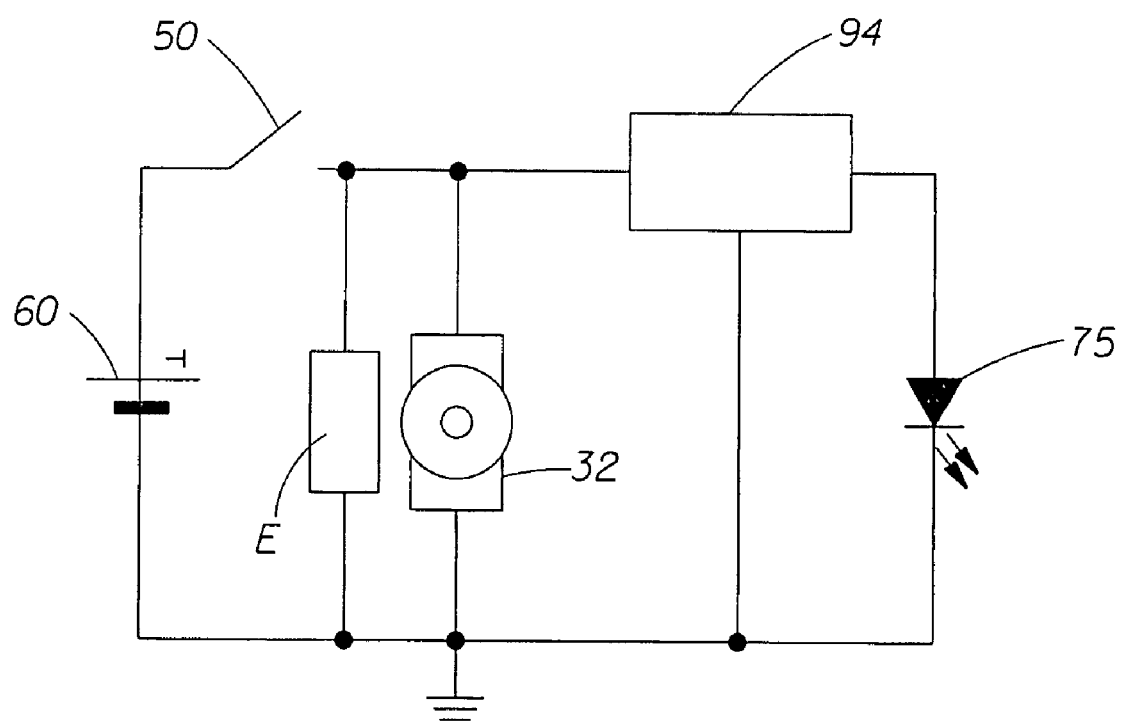
FIG. 12 is a schematic of an electrical configuration suitable for use with the present invention.

FIG. 12 illustrates an exemplary schematic of an electrical configuration for a representative embodiment sensor-responsive toothbrush. In this configuration, the light-emitting element 75, one or more sensors E, and the motor 32 are powered or activated concurrently with one another by switch 50. When the light-emitting element 75 is an LED, it may be desirable to include a voltage or current driver 94 which provides a constant voltage or current output to the LED despite changes to the input voltage or current, especially as the voltage or current output from a battery tends to decrease over time. A voltage or current driver suitable for use with the present invention is the ZXSC310 Single or Multi Cell LED Driver manufactured by Zetex Semiconductors, Oldham, UK. Other embodiments of the invention include, for example, separate switches can be provided to separately active the light-emitting element, the sensor(s), and the motor. Additionally, more than one light-emitting element might be provided. Light-emitting elements having different spectral, photometric, radiometric, and colormeteric characteristics (e.g., different dominant wavelengths, peak wavelengths, radiometric power, etc.) might be provided to accommodate multiple uses in a single electric toothbrush. Alternatively, a first light-emitting element might function as a sensor output element and a second light-emitting element might provide a responsive output in response to a sensor input.

Figure 13:
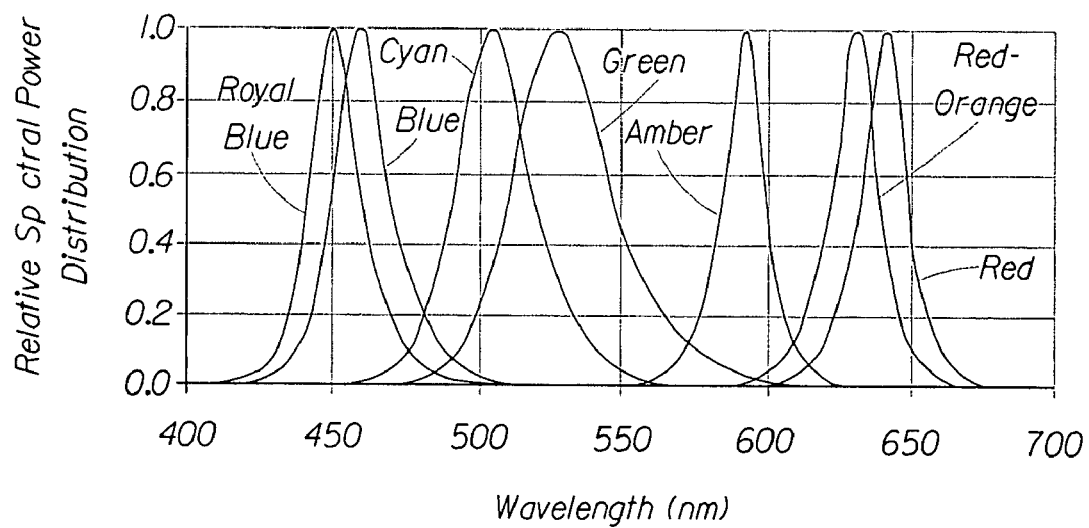
FIG. 13 is a graph of the spectral distribution for a variety of colors for light-emitting elements that are suitable for use with the present invention.
Figure 14:
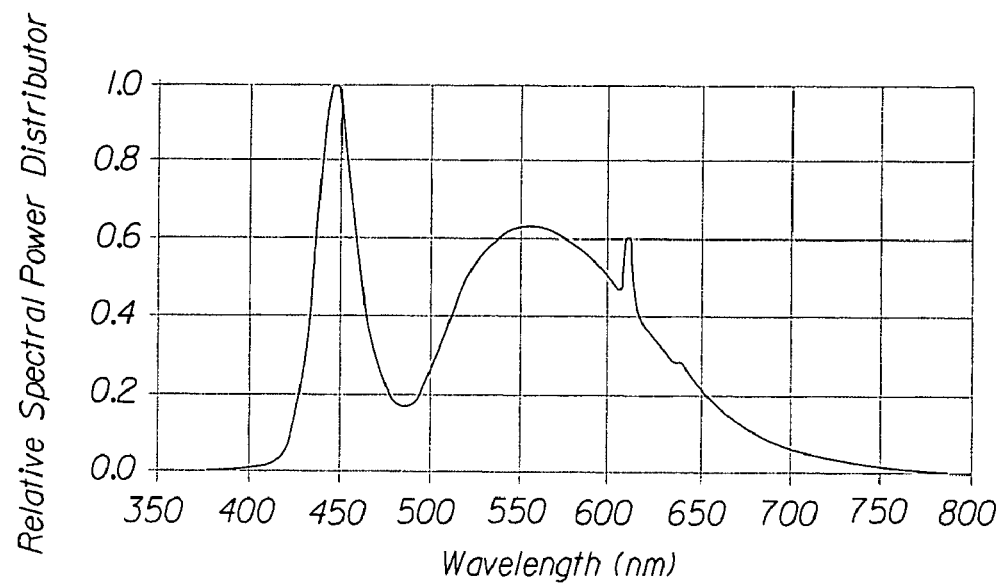
FIG. 14 is a graph of the spectral distribution for a light-emitting element that emits a white light that is suitable for use with the present invention.
Figure 15:
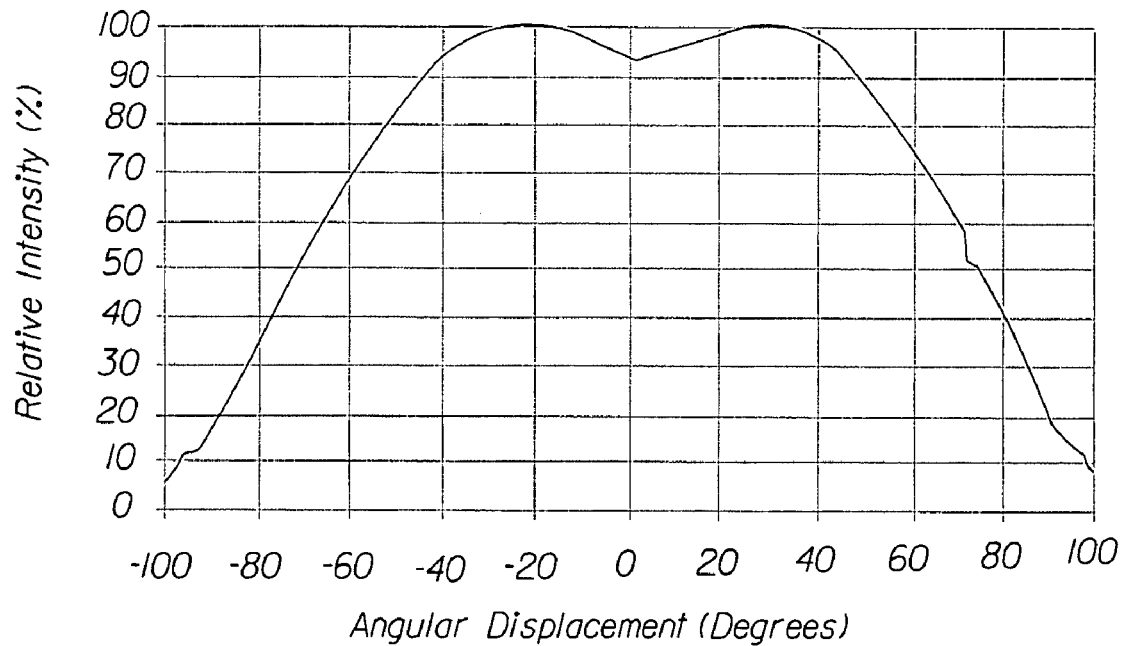
FIG. 15 is a graph illustrating a light radiation pattern suitable for use with the present invention.

FIGS. 13 and 14 illustrate spectral distributions for various colors of commercially available LED lighting unit used in the electric toothbrushes described herein. These spectral distribution graphs are for Luxeon™ 1-watt emitter lighting elements, however these distribution patterns may be achieved with other lighting units. Specifically, FIG. 13 is a graph of the relative spectral power distribution for various colors light-emitting elements. FIG. 14 illustrates the colors of royal blue, blue, cyan, green, amber, red-orange, and red. FIG. 15 is the relative spectral power distribution for a white color lighting element.

A sensor-responsive toothbrush of the present invention can additionally include sensors for monitoring treatment and/or diagnosing conditions within the oral cavity. A sensor output element can be used to generate a sensor input, such as a fluorescence signal from bacteria or caries, by emitting light at a wavelength that fluoresces bacteria in a manner that is detectable by a sensor input element. The fluorescence signal detected by the sensor input elements can provide information about the concentration of bacteria in a periodontal packet, hard tissue (carious lesion), saliva or mycosis, as well as, information about teeth whitening and brightening. An additional fluorescence signal can be employed for early diagnosis of different mucosal diseases including cancer. In one embodiment, the sensor-responsive toothbrush can include a signal mechanism for indicating to a user when a treatment is complete or a condition has been detected based on the fluorescence signal. In another embodiment, a reflectometer can be incorporated. For example, photo-induced current through LED can be utilized for reflected light detection. In other embodiments, separate LED and photodetectors can be employed for measuring reflections within the oral cavity at different wavelengths. Reflections can be employed for diagnostic of caries, whitening, brightening of hard tissue and/or mucosa diseases.

The preferred embodiment toothbrushes can utilize a responsive output that emits light or electromagnetic radiation that serves to heat the oral cavity or otherwise dissipate energy therein. Thus, the term "light-based output" may include outputs that emit or produce heat in response to the visible or invisible light energy. There are two systems for measuring light: radiometry and photometry, wherein radiometry is measurement of electromagnetic radiation within the frequency range between $3\times10^{11}$ and $3\times10^{16}$ Hz and photometry is the measurement of electromagnetic radiation that is detectable by the human eye. As known in the art, radiometric units include: Energy (Newton meter or joules), Power or Radiant Flux which is the flow of Energy with respect to time (joules/second or watts), Irradiance or Flux Density which is power per unit area (watts/$m^2$), Radiant Intensity which is power per unit solid angle (watts/steradian), and Radiance which is the power per unit projected area per unit solid angle (watts/$m^2$-steradian). Equivalent photometric units include: Power or Luminous Flux (lumen) and Luminous Intensity (lumen/sr or candela). Another characteristics of the light that will be discussed is the viewing or half angle. As described herein the half angle is two times the included angle (in degrees) between the peak and the point on one side of the beam axis at which the luminous intensity is fifty percent of the maximum or half of the beam angle. Yet another characteristic that will be discussed hereafter relates to the amount of heat or Emission Temperature (Celsius) which is generated by an LED at a tooth surface. Additionally, the total electric power consumed by the LED ("power dissipation") disposed on the head of the illuminated electric toothbrush will be characterized. For simplicity herein, units may be discussed in either radiometric units or photometric units, although radiometric units are preferred. Intensity can be either luminous intensity measured in candelas (or lumens/steradian), or flux density measured in Watts/meter$^2$.

All test methods described herein are performed when the sensor responsive illuminated electric toothbrush is operated at the current normally drawn to operate the device when the brush is fully charged and turned on, the bristles are moving, and the LED is illuminated.

Characteristics of the LEDs of the present invention are discussed more fully below.

1. Flux Density at a Representative Tooth Surface ("FDRT")

Figure 16:
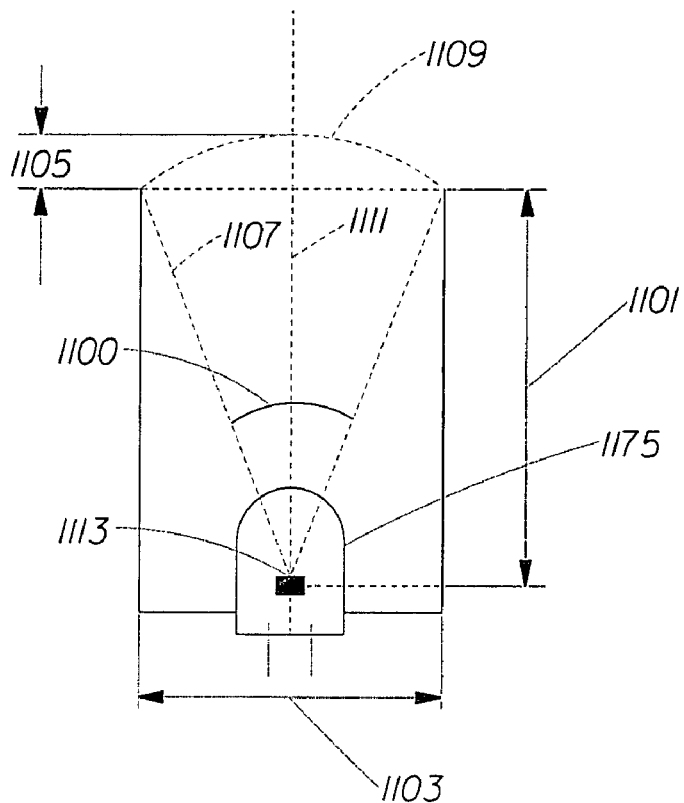
FIG. 16 is a diagram illustrating the geometry of the void between a light-emitting diode and the surface to be exposed to light.

This test is intended to represent the radiant flux density projected onto a tooth surface in W/m$^2$. A detector calibrated in Watts having a detector aperture area of less than about 3.14, 1.77, 1.54, 1.33, 1.23, 1.13, 1.04, 0.95, 0.87, 0.79, 0.70, 0.64, 0.50, and/or 0.46 cm$^2$ and/or greater than about 0.28, 0.31, 0.32, 0.33, 0.38, 0.44, 0.46, and/or 0.50 cm$^2$ and a detector aperture diameter of at least about 0.60, 0.63, 0.64, 0.70, 0.76, 0.80, 0.90, 0.95, 1.00, 1.05, 1.10, 1.15, and/or 1 cm and/or less than about 2.0, 1.50, 1.40, 1.30, 1.25, 1.20, 1.15, 1.10, 1.00 cm, and the detector aperture has a distance ("detector distance") of greater than about 0.55, 0.60, 0.63, 0.64, 0.66, 0.68, 0.70, 0.72, 0.74, 0.76, 0.80, 0.85, 0.90 and/or 1.0 cm, and/or less than about 2.0, 1.5, 1.4, 1.3, 1.25, 1.20, 1.15, 1.10, 1.05 and/or 1.0 cm from the light-emitting point of the LED. Traditionally, the detector comprises an iris that can provide a detector aperture area of the desired size. The LED should be positioned facing the detector aperture, and the mechanical axis of the LED should pass through the center of this detector aperture. The detector measures radiant flux (Watts) at the detector. The detector measures the radiant flux over the entire detector aperture area. Therefore, the resulting number is a total value of the radiant flux. The FDRT is the total value of the radiant flux divided by the Spherical Area of the cap 1109 (as shown in FIG. 16 which illustrates the geometrical relationship between the LED and the surface to be exposed to light). The spherical area of the cap can be calculated by the following equations:

$$S=2\pi R(R-l)$$

where:

$$R=\sqrt{l^2+d^2/4}$$

S=spherical area of the cap
l=detector distance
d=diameter of detector aperture area.

FDRT=Total Radiant Flux (Watts)/S

Figure 17:
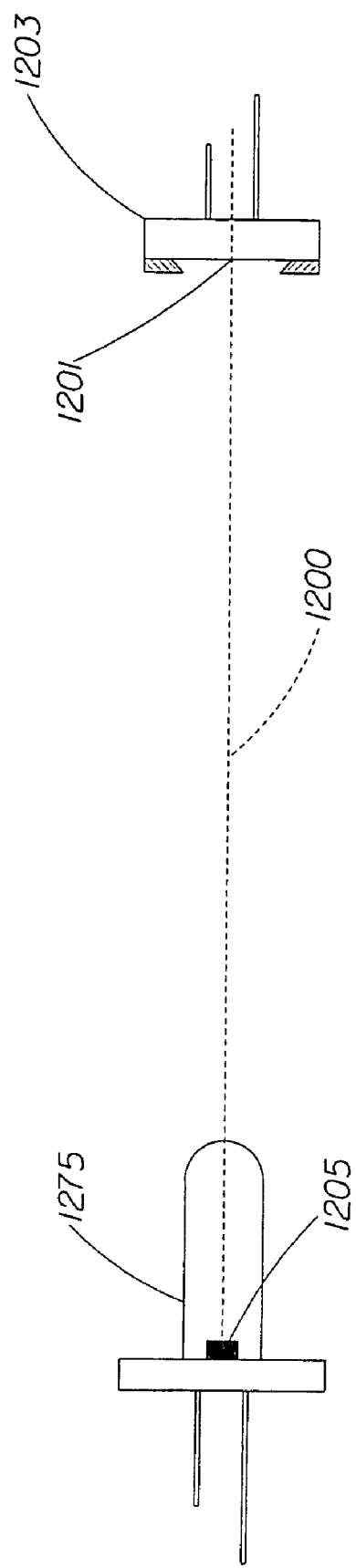
FIG. 17 is a diagram illustrating a test method for measuring average intensity of the light within a particular solid angle.

This radiant flux (Watts) is divided by the spherical area of the cap to result in flux density at a representative tooth surface (W/m$^2$). An example of a device suitable for measuring the FDRT includes the OL 730CV Radiometer/Photometer manufactured by Optronic Laboratories, Inc. of Orlando, Fla. As illustrated in FIG. 17 detector distance "l" (as shown at 1200) is the distance between the light-emitting point 1205 of LED 1275 and the entrance aperture 1201 of detector 1203. This detector distance "l" (as shown at 1200) is measured from the light-emitting point 1205 of the LED 1275 to the plane of the detector aperture 1201 of the detector 1203.

The FDRT of the inventive sensor responsive illuminated electric toothbrush is from at least about 30, 35, 40, 45, 50, 55, 60, 70, and/or 100 mW/cm$^2$ and/or less than about 300, 250, 200, 150, and/or 100 mW/cm$^2$ or any combination of these. It is believed that toothbrushes comprising LEDs that individually emit light at the aforementioned FDRT can result in whitening and other oral care benefits when used in the mouth alone or in combination with other oral care compositions. To achieve these oral care benefits at least one of the LEDs disposed on the head of the toothbrush must emit light having an FDRT of at least about 30 mW/cm$^2$. Light having a higher FDRT may also result in whitening or other oral care benefit, however if 300 mW/cm$^2$ is exceeded a user may need to take safety measures to prevent damage to the oral cavity.

2. Percent Total Luminous Flux within a Solid Angle

In one embodiment of the LED of the electric toothbrush, at least about 75%, 80%, 85%, 90%, 95%, 100% of the total power (watts) of the LED is contained within the solid angle with a vertex in the center of the LED of at least about 0, 0.5, 0.55, 0.6, 0.65, 0.7, 0.75, 0.8, 0.9, 0.95, and/or 1 steradian ("sr") and/or less than about 6.3, 5.5, 5, 4.5, 4, 3.5, 3, 2.5, 2, 1.5, 1.3, 1.2, 1.1, and/or 1 sr. The solid angle having a vertex in the light-emitting point of the LED can be calculated using the equations below:

$$\alpha=S/R^2=2\pi h/R,$$

where:

$$h=R-a \text{ and}$$

$$R=\sqrt{a^2+b^2/4}$$

α=solid angle (sr)
S=spherical area of the cap
a=axial distance
b=diameter of the dimensional area These calculations are similar to the calculations as used above to calculate the FDRT, and the axial distance and dimensional area have similar values to the detector distance and detector area, however no detector is present in the calculation of the solid angle.

Figure 20:
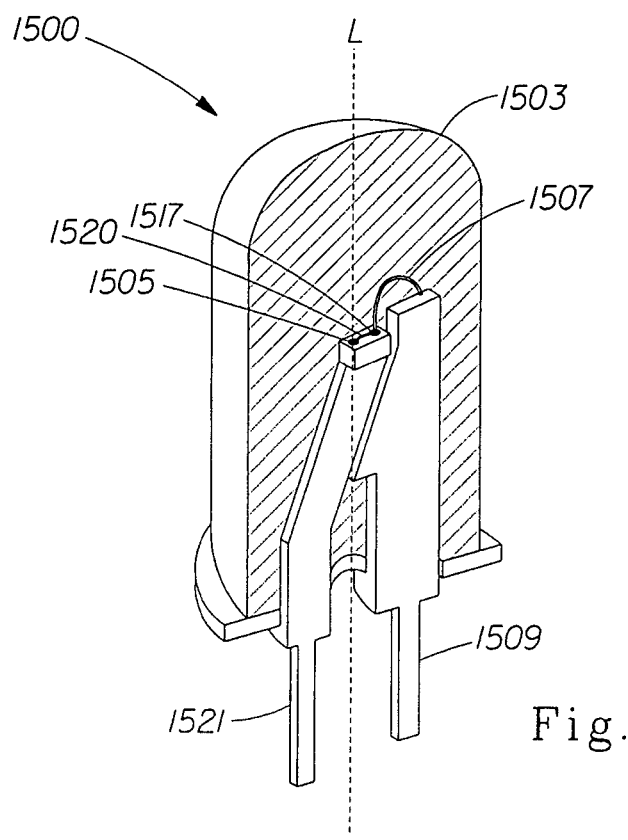
FIGS. 20-23 are cross-sectional views of a light-emitting diode having more than one light emitter, and a single optical output.

A diagram of the void space within which the LED emits light towards the surface to be exposed to light is shown in FIG. 16. The elements of the equation are depicted in FIG. 20 wherein "α" is the solid angle (shown at 1110) with a vertex (shown at 1111) in the light-emitting point 1113 of the LED 1175. "a" (illustrated in FIG. 20 at 1101) is the vertical distance between the emitting surface of the LED and the surface to be exposed to the light-emitting from the LED ("axial distance"), "b" (shown at 1103) is the diameter of a circular area comprising the LED, and "S" (shown at 1109) is the spherical area of the cap. "h" (shown at 1105) equals "R" (shown at 1107) minus "a" (shown at 1101). "b" can be at least about 0.60, 0.63, 0.64, 0.65, 0.70, 0.76, 0.80, 0.90, 0.95 and/or 1.00 cm, and/or less than about 2.0, 1.50, 1.40, 1.30, 1.25, 1.20, 1.15, 1.10, 1.05 and/or 1.00 cm. "a" can be greater than about 0.55, 0.60, 0.63, 0.64, 0.66, 0.68, 0.70, 0.72, 0.74, 0.76, 0.80, 0.85, 0.90 and/or 1.00 cm, and/or less than about 2.0, 1.50, 1.40, 1.30, 1.25, 1.20, 1.15, 1.10, 1.05 and/or 1.00 cm.

To determine the percent of power within the solid angle, first, the total power emitted from the LED must be measured, and second, the power within a particular solid angle area must be measured. Finally, the percent power within a particular solid angle is calculated. The total power emitted from the LED can be determined by either the goniophotometer method and/or the integrating sphere method. The goniophotometer method allows for the total radiant flux to be measured in Watts (when the goniophotometer is calibrated in Watts). The rotating detector of the goniophotometer scans the surface of a spherical shaped area surrounding the LED. The partial fluxes dΦ incident on each element dA of the surface represent a total radiant flux:

$$E(\theta, \phi) = d\Phi/dA$$

Which can be weighted and integrated to give the value of the total radiant flux Φ, $$\Phi = \int_{(A)} E\, dA$$

Another method of measuring the total radiant flux from an LED is to use an integrating sphere (calibrated in Watts) to compare the tested LED to a standard LED with a similar spatial and spectral power distribution. If no perfectly matches standard is available, a correction for color can be calculated; however a correction for spatial power differences is more difficult to calculate. Most integrating spheres are no more than 10 cm in diameter. Therefore, an auxiliary LED of the same type should be inserted into the integrating sphere to allow for a correction to be applied for the self-absorption of the test LED. Spheres with two entrance and one exit port for the detector should work. Both of these methods are described in CIE 127 (1997) entitled "Measurement of LEDs", which is published by the International Commission of Illumination.

Second, the power within a particular solid angle is measured. To choose the solid angle within which the power is measured, the axial distance and diameter of dimensional area for the desired solid angle must be determined using the aforementioned equations. The axial distance value corresponds to the detector distance value, and the diameter of the dimensional area value corresponds to the detector aperture area value. By choosing these values when performing the test, the power within the desired solid angle is measured. If the detector has been calibrated in Watts, this results in total radiant flux within the desired solid angle.

The measurement of total radiant flux (within a particular solid angle) of the LED involves a detector calibrated in Watts having a circular aperture 1201 as shown in FIG. 17 with an area of less than about 3.14, 1.77, 1.54, 1.33, 1.23, 1.13, 1.04, 0.95, 0.87, 0.79, 0.70, 0.64, 0.50, and/or 0.46 cm and/or greater than about 0.28, 0.31, 0.32, 0.33, 0.38, 0.44, 0.46, and/or 0.50 cm$^2$, and a detector aperture diameter of at least about 0.60, 0.63, 0.64, 0.70, 0.76, 0.80, 0.90, 0.95, 1.00, 1.05, 1.10, 1.15, and/or 1 cm and/or less than about 2.0, 1.50, 1.40, 1.30, 1.25, 1.20, 1.15, 1.10, 1.00 cm. The LED should be positioned facing the detector aperture 1201 at a detector distance 1200 from the light-emitting point 1205 of the LED 1275 of about 0.55, 0.60, 0.63, 0.64, 0.66, 0.68, 0.70, 0.72, 0.74, 0.76, 0.80, 0.85, 0.90 and/or 1.00 cm, and/or less than about 2.0, 1.50, 1.40, 1.30, 1.25, 1.20, 1.15, 1.10, 1.05 and/or 1.00 cm. The mechanical axis of the LED should pass through the center of this detector aperture.

Finally, the percentage of light emitted within the desired solid angle is calculated by the equation:

$$\frac{\text{Total Radiant Flux Within the Desired Solid Angle}}{\text{Total Radiant Flux}} =$$

% of Light Emitted Within the Desired Solid Angle

3. Half Angle and/or Viewing Angle

Another method for determining if a sensor responsive illuminated electric toothbrush emits light having the desired characteristics is to examine the half angle and/or viewing angle of the LED. As described herein the half angle is two times the included angle (in degrees) between the peak and the point on one side of the beam axis at which the luminous intensity is fifty percent of the maximum or half of the beam angle. This can also be referred to as the viewing angle. The smaller the half angle the more focused the light. The more focused the light-emitting from the LED, the less light is needed to achieve the desired luminous intensity and/or FDRT. Having a more focused angle of light results in less light wasted from shining in non-preferred directions, i.e. shining into the bristles areas. If light is shined in non-preferred directions, more light will be required to achieve the desired luminous intensity or FDRT, often resulting in increased heat levels. Increased heat emission from the illuminated electric toothbrush can result in damage to the teeth and tissues in the oral cavity. The half angle $$\left(2\theta\tfrac{1}{2}\right)$$

of the LED can be less than about 50°, 49°, 48°, 47°, 46°, 45°, 44°, 43°, 42°, 41°, 40°, 38°, 36°, 34°, 32°, 30°, and/or 28° and/or greater than about 0° and/or 5°.

4. Emission Temperature

Using an LED on the head of a toothbrush, which is then placed into the oral cavity for brushing and/or treating the teeth, may introduce heat as well as light into the oral cavity. The light can be absorbed by the surface of the tooth, thereby generating additional heat at the tooth surface. If heat is generated within the oral cavity, the pulp chamber of the tooth can be increased, which may result in pulpitis or other damage to the oral cavity. To avoid causing damage in the oral cavity, the temperature of the surface of the teeth should remain less than about 43° C., 40° C., 39° C., 38° C., 37° C., 36° C., 34° C., 30° C., and/or 25° C. If the temperature of the surface of the teeth is increased beyond the aforementioned temperatures, the pulp chamber of the tooth may be overheated, thereby resulting in pulpitis. Therefore, the light emitted by the illuminated electric toothbrush should not produce heat that raises the temperature of the surface of the teeth greater than about 43° C., 40° C., 39° C., 38° C., 37° C., 36° C., 34° C., 30° C., and/or 25° C. In one embodiment the temperature of the surface of the teeth is kept below about 43° C. by using a standard LED and providing a continuous forward current less than about 200 milliamps ("mA") to the standard LED.

Figure 18:
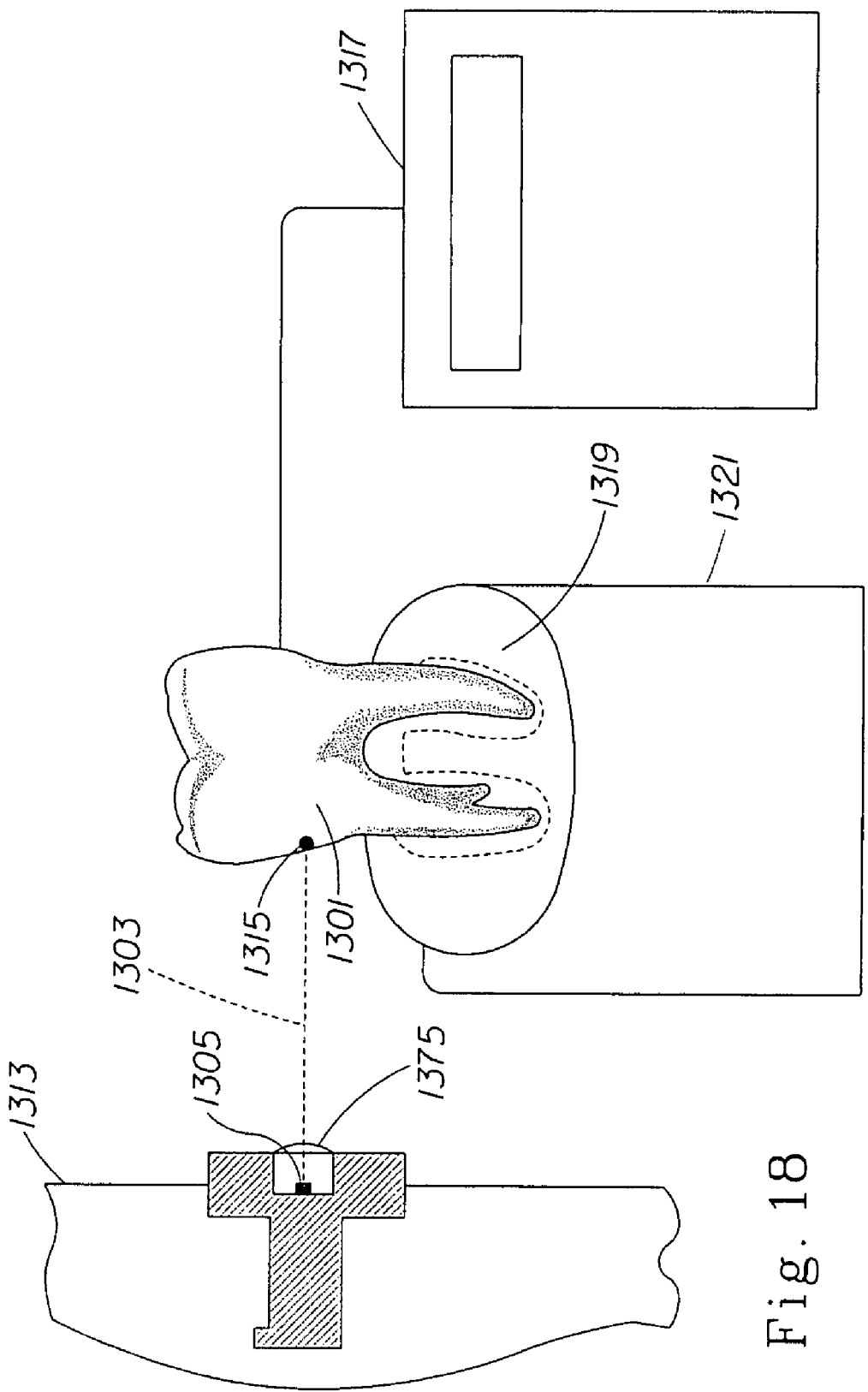
FIG. 18 is a diagram illustrating a test method for measuring the effect of a sensor responsive illuminating electric toothbrush on the temperature at the surface of the teeth.

The temperature generated at the surface of the teeth resulting from exposure to light emitted from the illuminated electric toothbrush is the "emission temperature." The emission temperature can be measured by devices known in the art such as a thermocouple 1315 (as shown in FIG. 18). One thermocouple suitable for use in the present test method is the SC-GG-T-30-36 thermocouple manufactured by Omega Engineering, Inc. The thermocouple can be attached, preferably with adhesive, to the surface of the tooth exposed to light-emitting from the LED. One suitable dental adhesive to use in this test method is Lucitone 199 manufactured by Dentsply. Alternatively, the temperature at the surface of the tooth can be measured after exposure to the light, so long as the thermocouple is touched to the tooth and the temperature reading is completed within a testing time of less than about 10, 9, 8, 7, 6, 5, 4, 3, 2, 1 seconds of terminating exposure of the tooth to the light. One method of measuring temperature after exposure to the light is terminated is by using a standard cotton swab to apply and hold the thermocouple on the tooth for the duration of the testing time to gather the temperature data. Additionally, a unit 1317 which translates the data from the thermocouple into temperature in degrees can be used; hand held unit HH5-08 manufactured by Omega Engineering, Inc. is suitable to be used with aforementioned thermocouple to translate data received from the thermocouple into temperature in degrees. This testing is performed in vitro on standard extracted human or bovine tooth 1301 samples, within an incubator set at 32° C. The test is performed within a incubator set at 32° C. to replicate the normal base temperature of a tooth placed in the mouth. A suitable incubator for this test is the THELCO 3DG, catalog #51221122 available from the Jouan Group of Companies. The tooth is placed in cast aluminum stand 1319 comprising a piece of cast aluminum with a space removed for placement of the tooth. The cast aluminum stand 1319 connects the tooth 1301 to a heat sink 1321. A heat sink suitable for use in the present test method includes heat sink 11-5602-48 VIS #031608 manufactured by Aavid Thermalloy. A power supply (not shown) can be provided to the heat sink. The "emission distance" is the distance 1303 between the light-emitting point 1305 of the LED 1375 and the surface of the tooth 1301. The emission distance 1303 can be less than about 3.14, 1.77, 1.54, 1.33, 1.23, 1.13, 1.04, 0.95, 0.87, 0.79, 0.70, 0.64, 0.50, and/or 0.46 cm and/or greater than about 0.28, 0.31, 0.32, 0.33, 0.38, 0.44, 0.46, and/or 0.50 cm from the surface of the tooth. The light-emitting point 1305 of the LED 1375 is placed at an emission distance of less than about 3.14, 1.77, 1.54, 1.33, 1.23, 1.13, 1.04, 0.95, 0.87, 0.79, 0.70, 0.64, 0.50, and/or 0.46 cm and/or greater than about 0.28, 0.31, 0.32, 0.33, 0.38, 0.44, 0.46, and/or 0.50 cm from the surface of the tooth 1301, and the illuminated electric toothbrush 1313 is turned on; thereby operating the LED 1375 and illuminating the surface of the tooth 1301. The tooth 1301 is then exposed to light-emitting from the LED 1375 for an emission time of less than about 15, 14, 13, 12, 11, 10, 9, 8, 7, 6, 5, 4, 3, 2, 1, and/or 0 minutes and the temperature of the tooth 1301 is measured by the standard thermo-couple 1315. The thermo-couple can be attached to a separate hand-held unit 1317 to translate the readings from the thermo-couple 1315 into temperature readings. The emission temperature should not exceed about 43° C., 40° C., 39° C., 38° C., 37° C., 36° C., 34° C., 30° C., and/or 25° C.

5. Power Dissipation

Additionally, to avoid damage to the oral cavity due to excessive heat generation, the total electric power consumed ("power dissipation") by the LED disposed on the head of the illuminated electric toothbrush should not exceed about 2, 1.5, 1, 0.95, 0.9, 0.85, 0.8, 0.75, 0.7, 0.5, 0.4, 0.3, 0.2, 0.1 Watts ("W").

6. Examples of Light-Based Responsive Outputs

A responsive output to an input signal could be to provide a particular luminiuos intensity or other spectral responsive output to treat a detected condition within the oral cavity, such as caries or bacteria. Luminous intensity of at least about 7 candelas and/or FDRT of at least about 30 mW/cm$^2$ can be achieved in the inventive sensor responsive illuminated electric toothbrush comprising a standard LED by increasing the forward current beyond that recommended by the manufacturer ("overpowering"), including more than one light emitter in the LED, and/or pulsing the light emitted from the LED, or any combination of these. Overpowering of the LED can shorten the life span of the LED. The amount the life span of the LED is shortened depends on the level of current used to overpower the LED and the characteristics of LED. However, this shortened life span will still exceed what is needed for use on a toothbrush, as a toothbrush is a disposable and/or replaceable item. In one embodiment the LED is disposed on a replaceable portion of the toothbrush, and can therefore be replaced if desired.

As previously noted, the term "light" is intended to encompass the spectrum of both visible and non-visible (e.g., ultraviolet and infra-red) light. This spectrum may extend from light having a dominant or centroid wavelength of about 10 nm (far ultraviolet) to light having a centroid wavelength of 106 nm (infrared), or the spectrum may include visible light having a centroid wavelength between about 370 nm and about 770 nm. Further, the spectrum may include visible light having a centroid wavelength between about 370 to about 500. As used herein, the term "centroid wavelength" is intended to refer to the wavelength which represents the perceived color of the light. This may be different than the peak wavelength which is the wavelength at which the radiant intensity of the LED is maximum.

Certain embodiment sensor responsive illuminated electric toothbrush comprises LEDs that emit light having a luminous intensity of at least about 7, 10, 15, 20, 30, and/or 40 and/or less than about 60, 50, 45, and/or 40 Candelas or any combination of these, or a FDRT of at least about 30, 35, 40, 45, 50, 55, 60, 70, and/or 100 mW/cm$^2$ and/or less than about 300, 250, 200, 150, and/or 100 mW/cm$^2$ or any combination of these.

Figure 19:
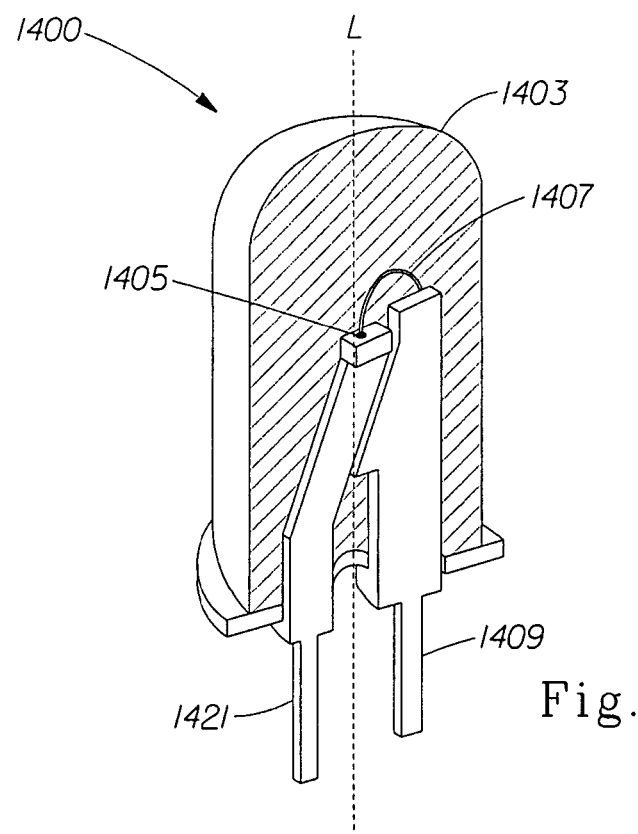
FIG. 19 is a cross-sectional view of a light-emitting diode.

One embodiment of the sensor responsive illuminated electric toothbrush comprises an LED as shown in FIG. 19. FIG. 19 shows a cross section of LED package 1400 comprising a lens 1403, a single light-emitting dice 1405, a wire bonding 1407, a positive lead 1421 and negative lead 1409, and a Longitudinal axis L. Various types of semi-conductor substrates having light-emitting properties can be used in LEDs of the sensor-responsive toothbrushes. One type of semi-conductor substrate having a light-emitting property is a dice. A "dice" is a single semi-conductor substrate having light-emitting properties. It is contemplated that the LED disposed on the head of the inventive illuminated electric toothbrush can comprise any type of semi-conductor substrate having light-emitting properties, including but not limited to a dice, so long as the illuminated electric toothbrush provides light having the desired properties described herein. The LED can have a diameter of at least about 0.5, 1, 2, 3, 4, 5, and/or 6 mm and/or less than about 5, 10, 15, and/or 20 mm.

Light can emit from many surfaces of the light-emitting point of an LED. However, for simplicity hereinafter all measurements of the distance from the light-emitting point and/or surface of the LED refer to the front surface of the semi-conductor substrate, such as the front surface of the dice 1405. If the LED has multiple dices, and therefore multiple front surfaces of the semi-conductor substrate, the distance from the light-emitting point of an LED should be the average of the distances from the front surface of the semi-conductor substrates. Light emits from a surface of the dice and is directed to the lens 1403 of the LED. Therefore, to measure a distance from the light-emitting point of a semi-conductor substrate, the front surface of the light-emitting element of the semi-conductor substrate must be identified. In one embodiment of the illuminating electric toothbrush the front surface of the light-emitting element of the LED is the surface of the dice 1405 (as shown in FIG. 19). Therefore, all measurements of distance from this embodiment of a light-emitting surface begin with the front surface of dice 1405.

Overpowering the LED results in the desired luminous intensity and/or FDRT because, luminous intensity and/or FDRT of a LED increases, within limits, as forward current input increases. Therefore, the luminous intensity and/or FDRT levels desired for the inventive illuminated electric toothbrush can be achieved by increasing the current to a standard LED beyond that recommended by the manufacturer. Increasing the current twice the maximum recommended by the manufacturer will almost double the luminous intensity and/or FDRT, while still resulting in a lifespan of the LED acceptable for use in an illuminated electric toothbrush. A standard driver can be used to deliver the chosen current level to achieve the desired luminous intensity and/or FDRT. A voltage or current driver suitable for use with the present invention is the ZXSC310 Single or Multi Cell LED Driver manufactured by Zetex Semiconductors, Oldham, UK. The minimum current to achieve the desired luminous intensity and/or FDRT can be greater than the maximum current recommended by the manufacturer for continuous operation, two times the maximum recommended by the manufacturer for continuous operation, or three times the maximum recommended by the manufacturer for pulsed operation. At a maximum the current can be increased to the level which causes immediate failure of the LED. One embodiment of the invention comprises a standard LED which delivers the desired luminous intensity and/or FDRT via a continuous forward current greater than about 35 mA, 40 mA, 45 mA, 50 mA, 55 mA, 60 mA, 65 mA, 70 mA, 75 mA, 80 mA, 90 mA, 100 mA, 150 mA and/or 200 mA and/or less than about 700 mA, 600 mA, 500 mA, 400 mA, 300 mA, 250 mA, 200 mA, 150 mA, 100 mA, 90 mA, 80 mA, 75 mA, 70 mA, 65 mA, 60 mA, 55 mA, 50 mA, 45 mA, 40 mA, and/or 35 mA. In one embodiment the minimum continuous current level can be the maximum continuous current rating for continuous operation, and the maximum continuous current level can be about the current causing immediate failure of the LED. Although the luminous intensity and/or FDRT does increase as the current increases, there is a point at which this correlation levels out, and further current increase does not result in luminous intensity and/or FDRT increase. This exact point depends on the properties and design of the LED. Additionally, as time passes and the LED is exposed to currents beyond that recommended by the manufacturer, the luminous intensity and/or FDRT begins to fade. One way of maintaining the desired luminous intensity and/or FDRT includes, but is not limited to, further increasing the current in order to maintain the same luminous intensity and/or FDRT. Although the current is increased to the standard LED to achieve the desired luminous intensity and/or FDRT, the current used is still lower than traditionally used for high power non-standard LEDs. Therefore, the heat generated by the standard LEDs does not increase the temperature of the surface of the teeth above about 43° C.

Stabilizing the current of the LED in a standard driver design does partially stabilize the luminous intensity and/or FDRT over time since the current stays the same as the LED decays. However, as the LED decays the current may need to be increased to maintain the same level of luminous intensity and/or FDRT. One way of maintaining constant luminous intensity and/or FDRT as the LED decays is to measure the luminous intensity and/or FDRT emitted from the LED with a built in sensor and adjust the current according to the measured value. Adjusting the current as the LED decays results in an illuminated electric toothbrush which continues to deliver light at the specified luminous intensity and/or FDRT over time. Another way of maintaining approximately the same luminous intensity and/or FDRT without including a built in sensor, is to include a timing circuit which increases the current to the LED over time as the LED decays. This can maintain approximated steady luminous intensity and/or FDRT via a simple design, and with minimal additional expense. A voltage or current driver suitable for use with the present invention is the ZXSC310 Single or Multi Cell LED Driver manufactured by Zetex Semiconductors, Oldham, UK.

Figure 21:
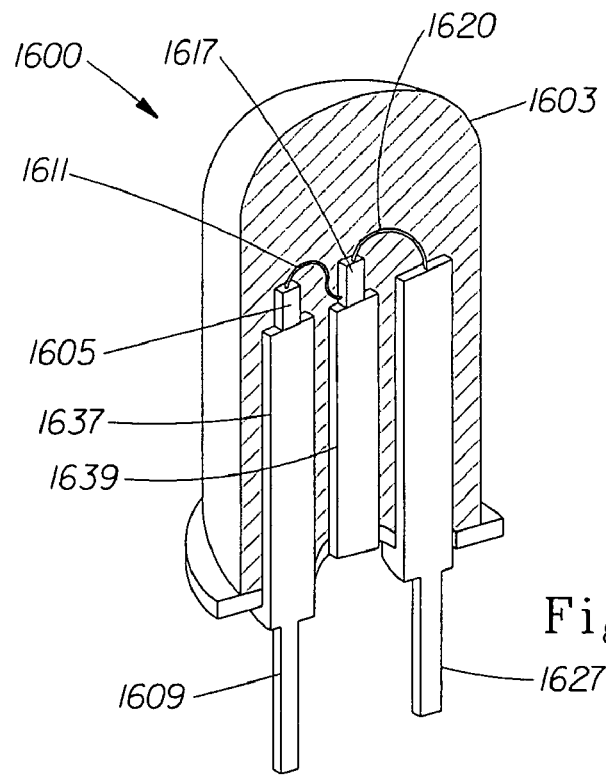
Figure 22:
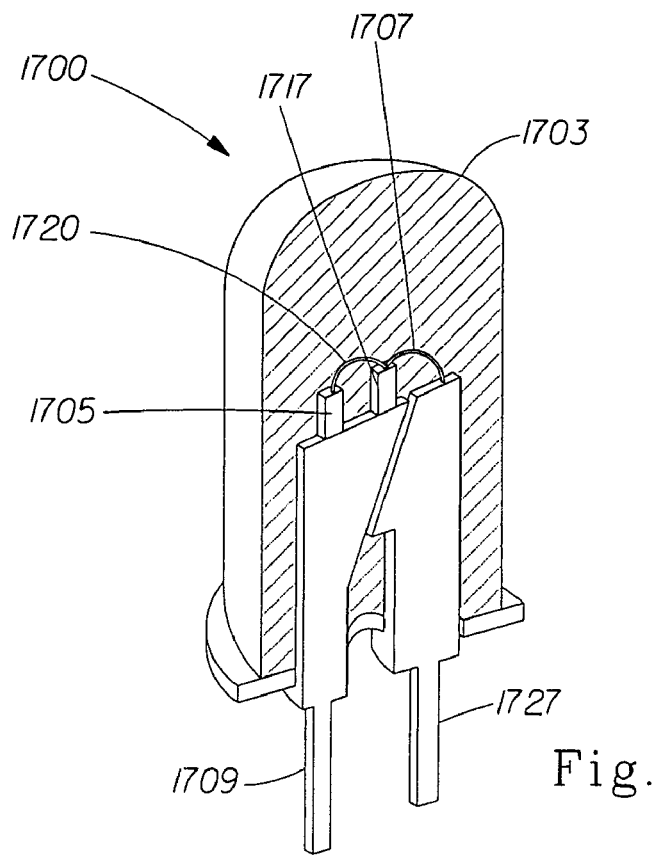
Figure 23:
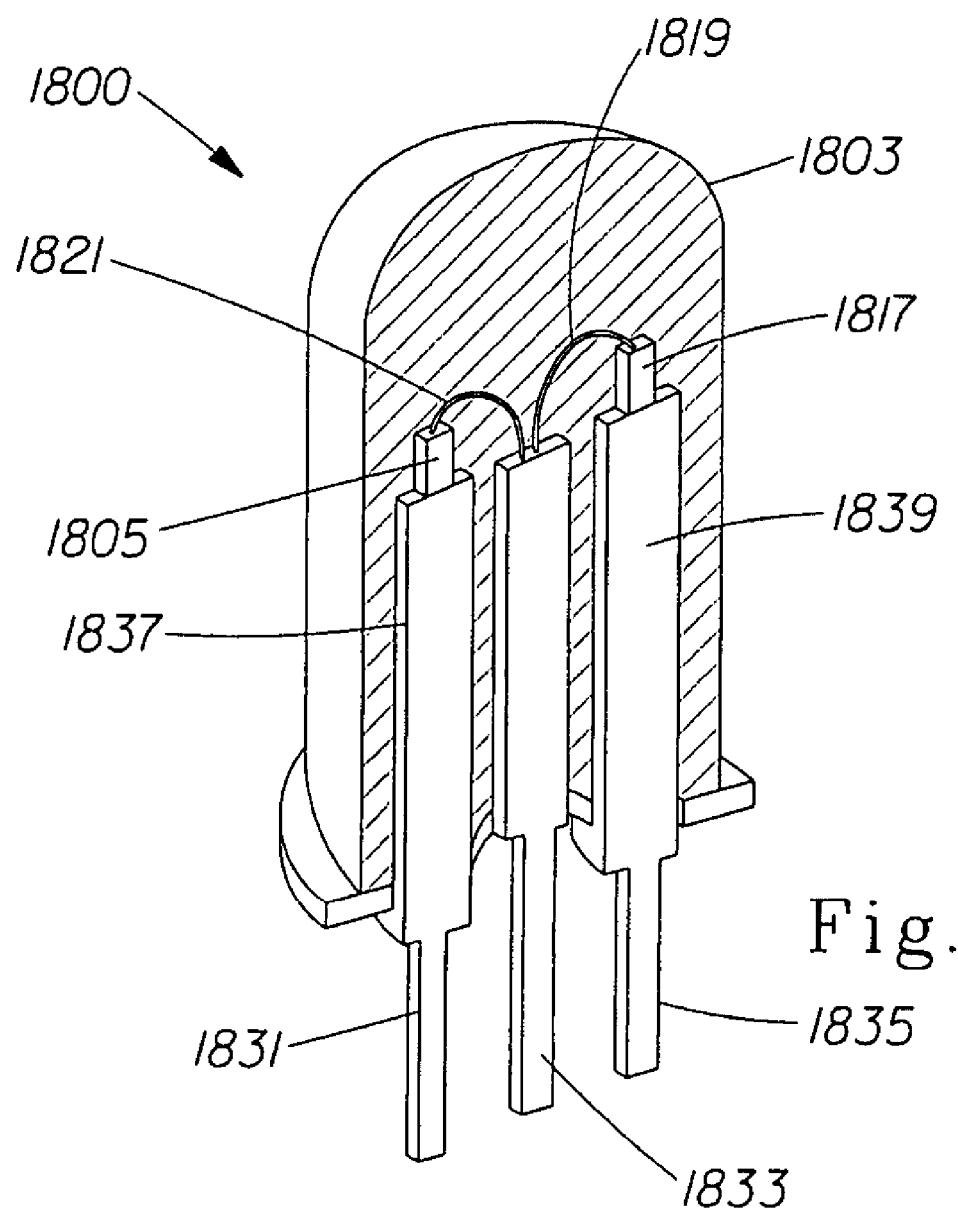

FIG. 20 shows another means for achieving the levels of luminous intensity and/or FDRT in the sensor responsive illuminated electric toothbrush by including more than one light emitter such as multiple dices. The following embodiments illustrate LEDs having two semi-conductor substrates that emit light, such as dices, however it is contemplated that the LED could comprise more than two dices. This embodiment 1500 has a single light output, the lens 1503, and one positive lead 1521 and one negative lead 1509. However, this single standard LED package contains more than one light emitter and more than one semi-conductor substrate, and can have more than two leads. All light from the light-emitting sources is combined to result in a single light output at lens 1503 of LED package 1500. The single LED package 1500 has multiple light-emitting dices 1505 and 1517 and a wire bonding 1507 and 1520. Embodiment 1500 shows a connection between the dices 1505 and 1520. This connection can be either a parallel connection or a serial connection. FIG. 21 illustrates multiple dices connected in series. This embodiment 1600 has a single light output, the lens 1603, and one positive lead 1609 and one negative lead 1627. However, this single standard LED package contains more than one dice 1605 and 1617, with each dice having an individual pedestal 1637 and 1639. The dices have a serial connection, wire bonding 1611 connects the top of dices 1605 to the bottom of dices 1617, and wire bonding 1620 connects the top of dices 1617 to the negative lead 1627. All light from the light-emitting sources is combined to result in a single light output at lens 1603 of LED package 1600. FIG. 22 illustrates multiple dices connected in parallel. This embodiment 1700 of the invention has a single light output, the lens 1703, and one positive lead 1709, and one negative lead 1727. The dices have a parallel connection, wire bonding 1720 connects the top of dices 1705 to the top of dices 1717, and wire bonding 1707 connects the top of dices 1717 to the top of the common negative lead 1727. All light from the light-emitting sources is combined to result in a single light output at lens 1703 of LED package 1700. In another embodiment 1800 (as shown in FIG. 23) of this multi-dice LED, the LED comprises a lens 1803, two semiconductor substrates, dices 1805 and 1817 shown connected in parallel, wire bondings 1819 and 1821, one positive lead 1833, and two negative leads 1831 and 1835. This LED also emits light from a single light output, the lens 1803. Each dice having an individual pedestal 1837 and 1839. It is also contemplated that the LED can comprise two positive leads, and one negative lead; and further this embodiment of the LED can be connected in series. Additionally, the LED can comprise more than two semi-conductor substrates having light-emitting properties, and the LED can comprise more than two leads. The LED can have a common or shared lead, or can have individual leads for each semi-conductor substrate having light-emitting properties. Further, each semiconductor substrate having light-emitting properties can be individually powered by a separate power source, such as a battery.

These dices can be electrically connected in parallel or in series. When they are connected in series, all current considerations are the same as for one single dice. The total voltage will be approximately $n \times V_i$ where n=number of dices, and $V_i$=forward voltage for a single dices. If the dices are connected in parallel, the total current will be approximately $n \times I_i$ and the total voltage approximately that of a single dice. Serial connection works well because it adjusts for differences between the dices. When the dices are connected in series, they automatically adjust their forward voltages and their luminous intensity and/or FDRT become very close. In either arrangement the two dices LED has approximately the luminous intensity and/or FDRT of $1.6 \times P_i$, where $P_i$ is luminous intensity and/or FDRT of a single dice. A three dices LED will likely have the luminous intensity and/or FDRT of about $2.26 \times P_i$. (Interference between the dices can prevent the luminous intensity and/or FDRT calculation from being a multiplier by the number of dice.) These dices can deliver the same color of light, or they can have different colors of light. However, if each individual light emitter emits the same light, the luminous intensity and/or FDRT of that color light from that one single LED is greater than a single standard LED emitting light of one color. Each of the individual light emitters can emit light having a wavelength of from about 440 to about 480 nm. A single LED could also contain two dices emitting different colors of light, for example a wavelength selected from the range of greater than about 370, 380, 390, 400, 425, 440, 450, 475, 480 and/or less than about 500 nanometers. The dices could also be selected such that the dices emit light of a different wavelength within the same color range; for example the dices could emit light having different wavelengths that result in the color blue. Further, the combination of the different wavelengths of light at the single optical output of the LED (the lens) could result in a specific combination of colors that delivers an oral care benefit. For example, two different compositions can be applied to the teeth, each of which reacts to a different wavelength of light. Additionally, different wavelengths of light may result in different reactions within the oral cavity; one wavelength of light may kill bacteria, another wavelength of light may whiten the teeth. Some colors are difficult to achieve by a single wavelength of light; this invention can be used to produce light of one of these unique colors. Thus the combination of different colors at the single optical output may result in a color that cannot be achieved by one dice alone. Therefore, using different colors could result in one or more oral care benefits that a single wavelength of a single color could not achieve.

Yet another means for achieving the luminous intensity and/or FDRT of the inventive illuminated electric toothbrush includes providing a non-continuous or pulsing current to the LED which results in pulsed or non-continuous light. This embodiment of the invention comprises a standard LED which provides the desired luminous intensity and/or FDRT level via a pulse forward current greater than about 100 mA, 125 mA, 150 mA, 175 mA, 200 mA, 225 mA, 250 mA, 275 mA, 300 mA, 325 mA, 350 mA, and/or 375 mA and/or less than about 900 mA, 800 mA, 700 mA, 600 mA, 500 mA, 400 mA, 375 mA, 350 mA, 325 mA, 300 mA, 275 mA, 250 mA, 225 mA, 200 mA, 175 mA, 150 mA, 125 mA, and/or 100 mA. In one embodiment the pulsed forward current is greater than about the maximum current rating for pulsed operation and less than about the current causing immediate failure of the LED. The minimum luminous intensity and/or FDRT of the light pulses can be that of continuous light, and the maximum luminous intensity and/or FDRT is Pc/Q where Pc is the luminous intensity and/or FDRT of continuous light and Q is the cycle ratio. The cycle ratio equals the duration of the pulse divided by the time period between pulses. The inventive cycle ratio is from about 0.01, 0.10, 0.25, 0.40, and/or 0.50 to about 0.50, 0.60 0.75, 0.80, and/or 0.99. The frequency of the light pulses can be about 0.01 Hz, 1 Hz, 10 Hz, 100 Hz, 500 Hz, or 1 MHz to about 1 MHz, 10 MHz, 100 MHz, 500 MHz, 1 GHz, or 10 GHz. The current amplitude for the pulsed operation of the LED can go from about $I_{maxp}$ to about 10 $I_{maxp}$, where $I_{maxp}$ is the absolute maximum current rating for pulsed operation, or from about $I_{max}$ to about 20 $I_{map}$, where $I_{max}$ is the maximum current rating for continuous operation.

Pulsing the current to the LED results in a reduction of the LED's power dissipation, and therefore prolonged battery life, as well as an increase in light brightness, and/or luminous intensity and/or FDRT. The improved battery life and increased brightness can vary depending on the properties and design of the LED.

In each of the above-described embodiments, the LED is disposed in, on, below or directly adjacent the moving and/or static bristle holders so that the light is directed onto the brushing area as efficiently as possible. Further, the LEDs are preferably arranged so that the principle direction of light emission is generally perpendicular to the top surface of the bristle holders and/or generally parallel to the direction of the bristles of the bristle holder. In other words, the LED is preferably arranged so that the centerline 90 of the LED is generally perpendicular to the top surface of the head and/or bristle holder. The centerline 90 typically passes through the lens 92 or aperture of the LED. When the LED is disposed within, on, or below a moving and/or static bristle holder, a cylindrical region or volume about the centerline 90 of the LED can be substantially devoid of bristles. The area substantially devoid of bristles can be larger and/or smaller depending on the size of the head of the toothbrush, and/or the number of bristles removed in the area surrounding the LED. The area substantially devoid of bristles can be greater than about 0.55, 0.60, 0.63, 0.64, 0.66, 0.68, 0.70, 0.72, 0.74, 0.76, 0.80, 0.85, 0.90 and/or 1.0 cm, and/or less than about 2.0, 1.5, 1.4, 1.3, 1.25, 1.20, 1.15, 1.10, 1.05 and/or 1.0 cm. The moving bristle holder still, however, preferably has at least one ring of bristles that encircle the LED, as shown by way of example in FIG. 7. Additional bristle tufts or an inner ring of bristle tufts might, however, be provided.

For tooth bleaching as well as other applications, it is often desirable to utilize a LED that provides a generally or substantially uniform distribution of radiometric power so that each tooth receives about the same of amount of radiometric power over the tooth surface. Therefore, embodiments of the inventive toothbrush comprise light radiation patterns having lamberertian or bell-shaped patterns, such as shown by way of example in FIG. 15. Other radiation patterns, such as the bat-wing pattern may also be utilized. As discussed above, however, the LED may provide a wide variety of light radiation patterns in accordance with the present invention.

An example of a commercially available light-based responsive output element useful for caries treatment is a Super Bright Red LED available from Kingbright Corporation of City of Industry, Calif. under the designation No. W53SRC/F.

The bristles of the bristle holders can be arranged to minimally interfere with the light emitted from the LED. Bristles can have a height of at least about 0.5, 0.6, 0.7, 0.8, 0.9 and/or 1.0 cm, and/or less than about 2.0, 1.5, 1.4, 1.3, 1.2, 1.1, and/or 1.0 cm. However, it is contemplated that the toothbrushes of the present invention may utilize bristle arrangements or materials that interact with the light emitted from the LED. For example, bristles and/or the top surface of the bristle holder located immediately adjacent the LED could include a reflective coating, such as nickel or chrome, to assist with directing light away from the head and toward the tooth surfaces. Alternately, bristles near the LED could be formed from a transparent or translucent material to further promote the transmission of light to the brushing area. The bristles might also be colored, pigmented, or dyed to generally match the color of the light emitted by the LED. In this way, the bristle would not absorb, but reflect, the light emitted by the LED. In addition, the use of a reflective shield that assists with directing light toward the tooth or gum surfaces which is placed around or near the LED might be utilized.

In one aspect of the invention, at least a portion of the radiation is emitted in a direction other than towards the hard tissue of teeth. This can be accomplished with the light-emitting toothbrush of the present invention by emitting radiation in a direction other than that represented by the cross sectional area defined by a circumference which surrounds the bristles or extensions thereof.

In another embodiment, optical radiation can be directed in multiple directions from the same oral appliance. For example, a light-emitting toothbrush of the invention can include two groups of LEDs, such that one group can radiate in a direction substantially parallel to the bristles, while the other group can radiate in the opposite direction.

The direction in which the optical radiation is emitted can be controlled in a variety of ways. In one embodiment, the optical radiation source can be disposed such that the radiation it produces travels toward the target tissue. This can be accomplished by positioning the optical radiation source at or near the surface of the oral appliance and placing the surface adjacent to the target tissue. In another embodiment, an optical element, e.g., a reflective or a refractive element, can be coupled to the radiation source for selectively directing radiation emitted by the source. The optical element can include, for example, rotatable mirrors, prisms, and/or diffusers, which direct the optical radiation toward target tissue. For example, a light-emitting toothbrush according to the one embodiment of the invention can include a radiation source optically coupled to a rotatable mirror that can direct radiation emitted by the source either along a plurality of bristles, or in a direction substantially opposite to the bristles.

In addition to providing single or multidirectional optical radiation, the sensor responsive light-based output toothbrushes of the present invention can supply single or multiple bands of optical radiation. For example, some treatment regimens may call for a single wavelength band such as a single blue color (central wavelength of 400-430 nm), a single green color (central wavelength of 540-560 nm), a single red color (central wavelength 620-635, 660), or a NIR single color (central wavelength 800-810 nm). Alternatively, a combination of these or other distinct wavelength bands could be applied, including two, three, or more distinct bands of optical radiation. For example, two separate wavelength bands can be employed to treat the same conditions more effectively or to treat two different conditions.

Multiple distinct wavelength bands can be achieved in a variety of ways. In one aspect of the invention, a broad band radiation source is used with an optical element to filter out unwanted wavelengths. For example, a filter or niters can remove all wavelengths from a broad spectrum with the exception of those in the blue and red portions of the spectrum. In another aspect of the invention, multiple distinct bands can be achieved with multiple radiation sources, each source providing optical radiation in a desired band. And in yet another aspect, a single radiation source which produces multiple distinct bands can be used. As an example, a single LED can be used to produce two or more distinct wavelength bands. Fluorescence conversion of radiation energy can be employed for generating additional wavelengths. As another example, a diode pumped fiber laser can be used to generate two wavelengths, one corresponding to the diode laser pumping the fiber and the other corresponding to the fiber laser wavelength. In some embodiments of the sensor-responsive toothbrush, it may be desirable to change wavelength bands. This can be accomplished with the light-emitting toothbrush of the present invention by using removable head portions. Each head portion can include a radiation source producing a light of a different wavelength. A user can then choose the desired wavelength band by selecting among removable head portions. Alternatively, the handle portion can include a broad band light source and the removable head portions can include filters to isolate desired wavelength bands. In another embodiment, one or more multi-color LEDs might be provided that are capable of emitting different wavelengths depending upon the voltage input or to which electrical lead power is provided. For example, a single LED might be capable of emitting wavelengths suitable for a bleaching treatment and treating bacteria. A controller within the toothbrush can vary the current, voltage, and/or the path of electrical power to the LED in order to provide different predetermined wavelengths and intensities based upon a detected sensor input or user selected regimen and the desired associated responsive output. A multi-color LED that may be suitable for use with the present invention is model no W154A4SUKPBVGKC available from Kingbright Electronic Co, ltd. (225 Brea Canyon Road, City Of Industry, Calif. 91789). This is a three-color LED (Red @ 635 nm, Blue @ 470 nm and Green @ 525 nm). The three LEDs inside one package have one common cathode and three separate anodes. Color choice is provided by applying voltage to a particular anode.

In yet another embodiment, the present invention can include reflective surfaces to more efficiently deliver radiation to tissue. When radiation is delivered to a target area, some of the radiation can be reflected by the tissue surface resulting in lost radiation. To save this reflected energy, the toothbrush can include a highly reflective surface which will return at least a portion of the reflected radiation to the tissue. For example, the light-emitting toothbrush includes a reflective surface for increasing radiation delivery efficiency. The tissue facing surfaces of the light-emitting toothbrush can similarly be reflective.

As previously noted, the light-based output(s) of certain embodiment sensor-responsive toothbrushes can emit or generate heat within the oral cavity. An LED, a laser diode, or a microlamp can generate heat energy that is up to 20 times higher than the generated optical energy. To accommodate unwanted waste heat, the sensor responsive light-emitting toothbrush can include heat transfer and/or cooling mechanisms. For example, a head portion of the exemplary light-emitting toothbrush can be at least partially formed of a heat conducting material for dissipating heat generated by the radiation source. For example, the head portion can include a head frame that is constructed from a material having high thermal conductivity and/or good heat capacitance and is thermally coupled to the radiation source to extract heat therefrom. This frame can be extended to external surfaces of the head, which can contact saliva or tissue during the use of the toothbrush. One skilled in the art will appreciate that a variety of materials can provide the necessary heat transfer such as, for example, metals including aluminum, copper or their alloy, ceramic and composite materials such as plastics having high thermally conductive components, such as carbon fiber. In one embodiment, heat is removed by heat transfer from the frame to adjacent tissue and/or saliva in contact with the light-emitting toothbrush. This heat can be employed for gentle heating of the oral tissue, and/or a paste applied to a portion of oral tissue, to provide additional or enhanced therapeutic effects.

In another embodiment, a sensor responsive phototherapeutic toothbrush can include a heat transfer element that transfers heat generated by a radiation source to a reservoir in which a phase transfer material can be stored. The phase transfer material, for example, ice, wax, or other suitable materials, absorbs the heat to change its phase, for example, from liquid to gas or solid to liquid, thereby dissipating the heat. Preferably, the phase transfer material has a melting or evaporation temperature in the range of about 30 to 50° C.

Although the above discussed examples of heat transfer elements are made with reference to the light-emitting toothbrush, one skilled in the art will appreciate that the heat transfer elements can be used in any of the oral appliances of the present invention. In particular, these heat transfer elements can provide for the storage or transfer of heat from the radiation source in the light-emitting mouthpiece to adjacent tissue, a handle, and/or the surrounding environment.

In some embodiments, the sensor responsive light-emitting toothbrush can include a heater for heating a target portion of the oral cavity, for example, while therapeutic radiation is applied to the target portion. Thermal therapy is useful in some treatment regimens and provides an additive or symbiotic effect when combined with phototherapy.

In some embodiments, heating is provided by a radiation source. In one aspect of the invention, the heater is a radiation source that is distinct from the radiation source generating therapeutic radiation, e.g., radiation source. In another aspect, heating can be provided by the same radiation source utilized for providing therapeutic radiation. For example, in such an embodiment, the radiation source can generate broadband radiation, or radiation in two or more bandwidths, such that at least one bandwidth is suitable for heating the oral cavity tissue. Alternatively, multiple radiation sources can be used, at least one of which provides radiation in a suitable wavelength range for deep heating of tissue. Exemplary deep healing radiation includes radiation having a wavelength in the range of about 0.38 to about 0.6 microns or a range of about 0.8 to 100 microns. One skilled in the art will appreciate that a variety of electric and non-electric heaters can be used with the oral appliances of the present invention.

Depending on the desired treatment regimen, the optical radiation delivered from the oral appliance of the present invention can be selectively directed to different regions of the oral cavity.

C. Chemical-Based Responsive Outputs

As described in greater detail herein, the various embodiment sensor-responsive toothbrushes with chemical-based outputs can be used exclusively with chemical-based outputs, or be provided with other responsive outputs such as light-based responsive outputs. For example, an LED may be used in conjunction with a whitening composition containing a responsive agent (e.g., hydrogen peroxide) for whitening teeth, and in particular, for enhancing or accelerating the whitening function of the composition by irradiating the brushing region either prior to, during, or after application of the whitening composition. As previously discussed, the chemical-based responsive outputs can be dispensed automatically by the toothbrush upon detection of an associated sensor input that indicates treatment by the chemical responsive output is desirable. Dispensing of the composition may be initiated automatically by the toothbrush in response to the detected sensor input or in response to a user selected regimen as previously discussed. The controller may initiate the dispensing by, for example, providing electrical power to a motor driven pump for a predetermined period of time.

A responsive output related to tooth whitening will now be described in more detail. Color in organic compounds is usually attributed to chromophores, which are unsaturated groups that can undergo π electronic transitions. Light can activate stain chromophores (undergo electronic transition), and reduce activation energy barrier making them more susceptible to attack by bleaching. In other words, activation of color bodies via light may enhance peroxide bleaching. Similarly, stain chromophores become more susceptible to abrasive whitening because of light treatment which results in faster and better whitening. Bleaching agents penetrate into the pores in enamel and dentin, and, therefore, both extrinsic and intrinsic color stains can be degraded and removed.

A wide variety of tooth whitening compositions may be used in combination with the sensor responsive electric toothbrushes described herein. The tooth whitening compositions may contain a bleaching agent, an abrasive agent, pH modifiers or any other agent that acts upon the chromophores of the teeth by mechanical or chemical action or a combination thereof. The tooth whitening composition can be provided in the form of a solution, paste, gel, viscous liquid, solid, or other suitable form. Illustrative bleaching agents include an oxygen radical or hydrogen radical-generating compound such as metal ion free peroxides, organic peroxides, and metal ion containing peroxides. Specific, non-limiting examples of bleaching agents include peroxides, metal chlorites, perborates, percarbonates, peroxyacids, persulfates, compounds that form the preceding compounds in situ, and combinations thereof. Suitable peroxide compounds include hydrogen peroxide, urea peroxide, calcium peroxide, carbamide peroxide, and mixtures thereof. In one embodiment the bleaching agent is carbamide peroxide. Suitable metal chlorites include calcium chlorite, barium chlorite, magnesium chlorite, lithium chlorite, sodium chlorite, potassium chlorite, and mixtures thereof. Additional bleaching agents also include hypochlorite and chlorine dioxide. In one embodiment the bleaching agent is selected from sodium chlorite, peroxide, sodium percarbonate, oxones, and mixtures thereof. The starting bleaching agent can be aqueous or solid material.

As discussed above, the various embodiments of the sensor responsive electric toothbrush may be used in combination with a whitening composition. A representative method of whitening teeth is as follows. After obtaining the sensor-responsive toothbrush and composition, the toothbrush is used within the oral cavity. A condition such as a discolored dental surface is sensed or detected by the toothbrush. The chemical-based output is then activated which for example can be in the form of dispensing of a suitable amount of a whitening composition from the toothbrush. The composition is applied to the dental surface, i.e. teeth, to be whitened. Preferably, such application is performed by ejection of the composition from the bristle holder of the toothbrush, and then transfer of the composition to the desired surfaces to be whitened. Generally, this latter step is performed in like fashion as brushing one's teeth. This process might be accompanied by a first audible signal that alerts a user that a relevant sensor input has been detected followed by a second audible signal (which may or may not be the same as the first audible signal) that alerts the user that a responsive output has been initiated. A third audible signal (which may or may not be the same as the first and/or second audible signals) might be generated to alert a user that the responsive output is complete. A user, upon hearing the first audible signal, may choose to concentrate his or her brushing in the region of the mouth where the first audible signal was provided until such time as the third audible signal is provided. Alternatively, the tooth whitening composition might be brushed, painted, or applied to the teeth with an applicator strip on the toothbrush from which the composition is dispensed. The toothbrush can further include a light-based output which is then activated and the light emitted there from is directed to the applied composition. It will be understood that the various whitening techniques of the present invention include variant strategies in which the light is directed to the dental surface before, during, and after application of the composition to the dental surface. Preferably, a brushing operation is then performed while the light continues to irradiate the composition applied to the dental surface of interest.

This whitening process is merely exemplary. The present invention includes a wide array of whitening techniques. Additionally, it is contemplated that a conventional brushing operation may be performed prior to, during, or subsequent to a whitening operation.

The oral care substance contains an active at a level where upon directed use, promotes the benefit desired by the user without detriment to the oral surfaces it is applied to. Examples of oral conditions these actives can address include, but are not limited to, appearance and structural change to teeth, whitening, stain bleaching, stain removal, plaque removal, tartar removal, cavity prevention and treatment, inflamed and/or bleeding gums, mucosal wounds, lesions, ulcers, aphthous ulcers, cold sores, and tooth abcesses.

Teeth are composite biological structures. For the purposes of stain removal, the important part of the tooth structure is the crown. The outer layer of the crown consists of enamel, which is a calcified structure that varies from translucent to yellow-gray in color. Underneath the enamel is the dentin, and then a central core chamber of pulp. Both the enamel and dentin layers are porous. Stain may migrate in these pores by diffusion due to the dynamic environment in the oral cavity from the secretions of the salivary glands.

Tooth discoloration that consumers experience in teeth is largely due to color bodies in the tooth structure itself and secondarily due to accumulated extrinsic stains from dietary tannins, which are often trapped in calculas as well. Discoloration of teeth occurs in both the enamel and dentin layers. The apparent color of the enamel-covered crowns is in part, the result of the color of the underlying dentin. Discoloration may also arise from calculus, which is the mineralized bacterial dental plaque on enamel surfaces. Tooth stains are normally due to porpyrin compounds (derivatives of porphin) originating from dietary habit and food components. They may be generated by mouth bacteria and may be accumulated under the enamel. Removal of extrinsic and intrinsic stains is important for achieving a high degree of whitening that is clinically measurable and consumer noticeable.

When the light emitted by the device is directly absorbed by the colored bodies present on and/or inside the tooth structure, the colored bodies ("chromophores") enter an excited state. When in their excited state these chromophores undergo chemical reactions resulting in loss of color and/or ease of their removal. Alternatively, the photoreactive pathways may be initiated by having a photosensitizer which is able to absorb the incident light energy and in its excited state transfer energy to the chromophores of the tooth structure and/or to oxygen. The activated choromophores may react with other chemical reactants or the active oxygen generated may react with the chromophores in their ground state causing them to be less chromogenic. Depending on the conditions employed, the active oxygen species can be singlet oxygen, superoxide, hydroxyl radical, hydroperoxyl radical, endoperoxide or a mixture of the above. The presence of amines or amides, in particular, can enhance the generation of superoxide. Additionally, a range of photosensitizers are known to promote active oxygen chemistry.

Additionally, light can activate stain choromophores (undergo electronic transition), and reduce the activation energy barrier making them more susceptible to peroxide bleaching as well as other cleaning and whitening agents. The activation of chromophores by the light may therefore, enhance the oral care benefit such as tooth bleaching and/or whitening. Similarly, stain chromophores can become more susceptible to abrasive whitening because of light treatment which results in faster and better whitening.

Chromophores (or photosensitizers) are useful as treatment agents for enhancing photodynamic and photo-thermal killing of microorganisms, as well as, tooth whitening and brightening. Chromophores include intrinsic light acceptors which induce and/or enhance chain-wise photochemical reactions leading to the generation of nitrogen oxide, singlet oxygen, and other radicals within tissue. Preferred chromophores include those which are nontoxic (i.e., those chromophores which can be provided at a concentration below which there is no action on bacteria or tissue without specific light). Exemplary exogenous chromophores for use in the present invention include dyes: methylene blue, indocyanine green, AT .A—an inductor of porphyrins in proliferating cells—, mineral photocatalysts and photosensitizers: $TiO_2$, nanoparticles, fullerenes, tubulene, carbon black, and other similar treatment agents.

Endogenous chromophores are also present within the oral cavity and the surrounding tissue. These chromophores are naturally occurring substances which provide similar radical production to the exogenous species described above when exposed to optical radiation in their absorption band. Exemplary intrinsic chromophores include porphyrines like protoporphyrins, coproporphyrins, and Zn-protoporphyrins. The absorption band for porphyrins includes blue light, and to a lesser extent, green light and red light. Other intrinsic chromophores include cytochromes such as cytogem and cytoporphyrin, bilirubin, and molecular oxygen.

A wide variety of tooth whitening substances may be used in combination with the electric toothbrush described herein, particularly an electric toothbrush comprising a light-based output. The tooth whitening substances may contain a bleaching agent, an abrasive agent, pH modifiers, chelants, surfactants, enzymes, solvents, polymers and photo-sensitizers or any other agent that acts upon chromophores of the teeth by mechanical or chemical action or a combination thereof. The tooth whitening substance can be provided in the form of a solution, paste, gel, viscous liquid, rinse, solid or other suitable form.

These embodiments are useful for treating diseases of the tongue, such as excessive bacterial growth. In another embodiment, a light-emitting component can be designed to treat tooth, gum, and/or cheek tissue. In this embodiment, optical energy is selectively directed toward cheek (wall of the oral cavity), gum, and tooth tissue. In yet a further embodiment, optical radiation from the light-emitting mouthpiece can be directed toward the soft tissue beneath the tongue, or other parts of oral cavity to support, e.g., oral drug or vitamin delivery. A drug or vitamin can be delivered to mucosa through opening, for example, in liquid form while the light source directs radiation on the drug and mucosa. This radiation can be selected to increase permeability of the mucosa for enhanced uptake and penetration of the drug into the oral cavity tissue. Alternatively, or in addition, the radiation can activate the drug for better therapeutic effect. Such a method of drug delivery can be employed at a physician's office or at home.

1. Bleaching Agents

Bleaching agents include metal ion free peroxides, organic peroxides, and metal ion containing peroxides that generate bleaching actives such as an oxygen radical. Examples of bleaching agents include, but are not limited to, peroxides, metal chlorites, perborates, percarbonates, peroxyacids, persulfates, compounds that form the preceding compounds in situ, and combinations thereof. Examples of peroxide compounds include, but are not limited to, hydrogen peroxide, calcium peroxide, carbamide peroxide, and mixtures thereof. In one embodiment the bleaching agent is carbamide peroxide. Metal chlorites include, but are not limited to, calcium chlorite, barium chlorite, magnesium chlorite, lithium chlorite, sodium chlorite, potassium chlorite, and mixtures thereof. Additional bleaching agents include hypochlorite and chlorine dioxide. In one embodiment the bleaching agent is selected from the group consisting of sodium chlorite, peroxide, sodium percarbonate, oxones, and mixtures thereof. The starting bleach can be aqueous or solid material. Peroxides, for example, penetrate into the pores in enamel and dentin, thereby degrading and removing both intrinsic and extrinsic stains.

The amount of bleaching agent in the whitening or bleaching substance may vary. For example, the bleaching agent could be present in an amount of about 3 to about 60 weight percent, based on the total amount of the tooth whitening substance. If hydrogen peroxide is the bleaching agent, according to one particular embodiment, it may be present in an amount from about 3, 5, 7, 10, 12, 15, 20, 30, 40, 50, 60 and/or less than about 60, 50, 40, 30, 20, 15, 12, 10, 7, 5 weight percent, and in another embodiment from about 7 to about 15 weight percent, based on the total amount of the tooth whitening substance. If carbamide peroxide is the bleaching agent, according to one particular embodiment, it may be present in an amount from about 3, 5, 7, 10, 12, 15, 20, 30, 40, 50, 60 and/or less than about 60, 50, 40, 30, 20, 15, 12, 10, 7, 5 weight percent, based on the total amount of tooth whitening substance. The radiant energy from the light-emitting element can be applied while the substance is in contact with the tooth, however, the light-emitting from the light-emitting element may also be applied prior to or after application of the tooth whitening substance.

In another embodiment, the whitening substance may be in the form of a multi-component system. For example, the whitening substance may be sold or supplied as a two-part system. This enables the components to be separated from each other prior to use and may promote increased bleaching efficacy and longer storage times.

In this particular embodiment, the two components, referred to herein as Part 1 and Part 2, can be mixed shortly or immediately before application. It is to be understood that this embodiment is intended to cover formulations comprising more than two components. The whitening substance may still be used more than 30 minutes after mixing, but, due to peroxide decomposition, some or most of its whitening effectiveness may be absent.

The first component, Part 1, can be of a gel or paste consistency. Thickeners and/or fillers may be added to achieve this consistency. Part 1 can comprises one or more metal peroxides, in particular those of monovalent or divalent metals. Examples of peroxides include calcium peroxide, zinc peroxide, and sodium peroxide, with other peroxides including, but not limited to, those of potassium, magnesium, and strontium also being suitable for use. In one embodiment the peroxide is suspended or dispersed in a medium to form a mixture which is from about 5% to about 40% metal peroxide by weight. In another embodiment the peroxide is from about 15 to about 30% peroxide by weight, and in another embodiment the peroxide is about 20%. In an alternative embodiment, the mixture is from about 2% to about 16% peroxide by weight, and in another embodiment the peroxide is from about 6% to about 10% peroxide by weight. The component may further comprise one or more additives to modify rheology, texture, flavor, fragrance, color, or other properties. Examples of additive components for use in Part 1 include glycerin, propylene glycol, polyethylene and/or polypropylene glycols, water, and mixtures of the foregoing. In some embodiments alcohol is added to the media.

In an alternate embodiment, the first component, the metal peroxide of Part 1, is suspended or dispersed in a liquid to form a mixture which can be from about 8% to about 25% by weight of peroxide, and in another embodiment from about 8% to about 15% by weight of peroxide.

Part 2 comprises a solution of one or more acids in water or aqueous solution which may be modified to achieve a desired consistency, such as that of a gel or paste, by the addition of thickeners and/or fillers. Acids suitable for use in the present invention include organic acids including acetic acid, tartaric acid, phosphoric acid, and citric acid. The total acid concentration in Part 2 can be from about 30% to about 100% of the stoichiometric requirement to convert metal peroxides to their salts and hydrogen peroxide, and in another embodiment from about 50% to about 80% of the stoichiometric requirement. Examples of thickening agents include xanthan gum, polyacrylic acid, and cellulose derivatives (e.g. carboxymethylcellulose) and examples of fillers include silica, diatomaceous earth, alumina, and powdered polyethylene or polypropylene or other polymers. The thickeners and/or fillers are added in a quantity sufficient to achieve the desired consistency. These same thickeners and fillers may also be used as additives in Part 1. Additives to modify rheology, texture, flavor, fragrance, and color may also be present in Part 2. In addition, alcohol or other water miscible solvents may be added to Part 2.

Parts 1 and 2 can be mixed in equal proportions to form the whitening formulation, although the ratio may vary from 1:1 depending upon the concentrations of the peroxide and the acid.

Once combined, the peroxide of Part 1 reacts with the aqueous acid of Part 2 to generate hydrogen peroxide in situ. The whitening substance utilized in conjunction with the illuminated toothbrushes described herein may also contain other appropriate additives such as stabilizing agents, boosters, alkalinizing agents, solvents, aromatizing agents, sweeteners, thickeners, adhesives and moisteners. By way of example, alkalinizing agents suitable for use include sodium hydroxide or triethanolamine, although the alkalinizing power may be modified by varying the amount of potassium salt, xylitol, sweeteners such as saccharine or derivatives of cyclamic acid, thickeners such as derivatives of starch, xanthan gum, colloidal silicas and similar substances, and moisteners, such as glycerine. Each one of the alkalinizing additives, aromatizing agents, sweeteners and thickeners can be present in the substance of gel in an amount between about 0 and about 6% by weight with respect to the total of the substance, while the moistener may be present in an amount between about 40 and about 80% by weight with respect to the total of the substance. The pH of light-activated substances of the present invention may be between about 4.5 and about 9.5, in another embodiment between about 5 and about 8, in another embodiment between about 5 and about 7 and in another embodiment between about 5 and about 6.

The light-activated compositions herein may comprise a thickening agent. In one embodiment the thickening agent (or viscosity modifier) can also function to increase retention of the composition on the teeth. The viscosity modifier may further function to inhibit settling and separation of components or control settling in a manner that facilitates re-dispersion and may control flow properties of the composition. A viscosity modifier is particularly useful to keep bleach agents or other oral care active agents that are in particulate form, suspended within the compositions of the present invention. The viscosity modifier is present at a level of from about 0.01% to about 20%, in one embodiment from about 0.1% to about 10%, and in another embodiment from about 1% to about 3%, and in yet another embodiment from about 0.4% to about 5%, by weight of the composition. Suitable viscosity modifiers herein include natural and synthetic polymers and gums such as cellulose derivatives (e.g. methylcellulose, carboxymethylcellulose, hydroxyethylcellulose, hydroxypropylcellulose etc), carbomer polymers (e.g. polyacrylic acid copolymer or homopolymer and copolymers of acrylic acid cross linked with a polyalkenyl polyether), karaya gum, guar gum, gelatin, algin, sodium alginate, chitosan, polyethylene oxide, acrylamide polymers, polyvinyl alcohol, polyamines, polyquarternary compounds, ethylene oxide polymers, polyvinylpyrrolidone, cationic polyacrylamide polymers and mixtures thereof. In one embodiment the thickening agent is selected from carbomers, e.g. the class of homopolymers of acrylic acid crosslinked with an alkyl ether of pentaerythritol or an alkyl ether of sucrose. Carbomers are commercially available from B.F. Goodrich as the Carbopol series. In one embodiment the carbopols are Carbopol 934, 940, 941, 956, and mixtures thereof. In another embodiment the viscosity modifier is a hydrophobically modified carbomer. Hydrophobically modified carbomers can increase the retention of compositions herein and/or integral carriers on tooth surfaces and slow the erosion of the compositions once applied on the tooth surfaces. Suitable hydrophobically modified carbomers include acrylate/C10-C30 alkyl acrylate crosspolymer such as Carbopol 1382, Carbopol 1342, Carbopol 1392, and Carbopol ETD 2020, all available from BF Goodrich, and acrylates/C10-C30 alkyl acrylate crosspolymer such as Pemulen TR-1 and Pemulen TR-2 both available from B.F. Goodrich. In one embodiment mixtures of hydrophobically modified carbomers with carbomers can be used. In another embodiment carboxy functional silicones (diacid, monoacid) are used to increase retention of bleaching agents on teeth.

The sensor-responsive toothbrushes described herein providing one or more chemical-based outputs may be used in conjunction with nearly any tooth whitening substance and/or substance, such as, but not limited to, the substances described in U.S. Pat. Nos. 6,488,914; 5,851,514; 4,980,152; 3,657,413; 4,983,380; 5,084,268; 5,171,564; 5,376,006; 5,645,428; 5,713,738; RE 34,196; 5,122,365; 6,558,654; 6,555,020; 6,536,628; 6,533,582; 6,521,215; 6,514,543; 6,479,037; 6,447,757; 5,891,453; 6,555,020; and 6,419,905 and Application Nos. WO 03/007680, and U.S. Ser. No. 10/154,020. It is not necessary that the substance exhibit an enhanced whitening function upon exposure to light. Benefits may result simply from exposure of the tooth surface to light from the electrical toothbrush prior to application of the whitening substance. Furthermore, additional benefits may stem from greater brushing or cleaning efficacy resulting from illuminating the brushing area.

2. Non-Bleach Tooth Whitening and Stain Removal Agents

Additional actives which provide an oral care benefit, such as whitening and/or stain removal, to the teeth include polymers, solvents, chelants, surfactants, and/or enzymes and mixtures thereof. These actives can activate the chromophores, and when used in combination with light-emitting from the head of an electric toothbrush, can result in whitening and/or stain removal. Additionally, some of the actives, such as polymers, can serve as oral care carriers to deliver an active to the surfaces of the oral cavity. Examples of polymers include polyvinylpyrrolidone, vinyl pyrrolidone/vinyl acetate copolymer ("PVP-VA"), Carbopol, Polyox resin, and/or silicones and mixtures thereof. The polymers can be added to the tooth whitening and/or stain removing substances in an amount from about 0, 5, 10, 30, 30, 40, 50, 60, 70, 80, 90 and/or less than about 90, 80, 70, 60, 50, 40, 30, 20, 10, 5 weight percent, based upon the total amount of tooth whitening substance. Examples of solvents include but are not limited to: hexamethyldisilozane ("HMDS"); ethyl acetate ("EtAC"); acetone; poly dimethyl siloxane("PDMS"); hexane; and isododecane and mixtures thereof. Solvents can be added to the tooth whitening and/or stain removing substances in an amount from about 0, 5, 10, 30, 30, 40, 50, 60, 70, 80, 90 and/or less than about 90, 80, 70, 60, 50, 40, 30, 20, 10, 5 weight percent, based upon the total amount of tooth whitening substance. Examples of chelants include, but are not limited to: pyrophosphates, including tetrasodium pyrophosphate ("TSPP") and tetrapotassium pyrophosphate ("TKPP"); glycine ("G1-H"); ethylenediamine tetraacetic acid ("EDTA"); ethane hydroxy diphosphonate ("EHDP"); and/or nitrilotriacetic acid ("NTA") and mixtures thereof. Chelants can be added to the tooth whitening and/or stain removing substances in an amount from about 0, 2, 3, 5, 10, 30, 30 and/or less than about 30, 20, 10, 5 weight percent, based upon the total amount of tooth whitening substance. Examples of surfactants include, but are not limited to: sodium lauryl sulfate ("SLS"); pluronics; polyethyleneoxide; quaternary ammonium; and/or zwitterionics and mixtures thereof. Surfactants can be added to the tooth whitening and/or stain removing substances in an amount from about 0.1, 2, 3, 5, 10, 30, 30, 40, 50 and/or less than about 50, 40, 30, 20, 10, 5 weight percent, based upon the total amount of tooth whitening substance. Examples of enzymes include, but are not limited: to proteases; carbohydrates; laccase; glucox; and/or papain and mixtures thereof. Enzymes can be added to the tooth whitening and/or stain removing substances in an amount from about 0, 1, 2, 3, 4, 5 and/or less than about 5, 4, 3, 2, 1, 0.5 weight percent, based upon the total amount of tooth whitening substance.

3. Photosensitizers

Boosters which facilitate or accelerate the action of a bleaching agent can include abrasives, metal catalysts and photosensitizers. Some of these photosensitizers may also be suitable for use in treating bacteria, caries, or other conditions with a light-based responsive output, some examples of which were previously discussed. Factors such as the amount of time, intensity, and wavelength of the light-based responsive output can be varied depending upon the photosensitizer and the desired treatment. These boosters can be added to the tooth whitening and/or stain removing substance in an amount from about 0, 2, 3, 5, 10, 30, 30, 40, 50, 60 and/or less than about 60, 50, 40, 30, 20, 10, 5 weight percent, based upon the total amount of tooth whitening substance. Suitable abrasives include silica, sodium carbonate, calcium phosphate and mixtures thereof. Metal catalysts include Copper, Iron, Manganese and other transition metal ions. A range of photosensitizers are known to produce active oxygen chemistry. These photosensitizers can absorb and can be activated by light in the wavelength of from about 380 to about 700 nm. Photosensitizers or their precursors are selected from the group consisting of: chlorophyll, in particular chlorophyll a & b, and bacterial chlorophyll; rose bengal; methylene blue; Zn phthalocyanine; porphyrin, in particular hematoporphyrin, uroporphyrin, and tetraphenylporphyrins and their complexes of Zn, Al, Si, Sn, phthalocyanines and their complexes with Zn, Al, Si, Sn and Curcumin.; chlorins, in particular bacterialchlorins; riboflavin; bilirubin; curcumin; EDTA; diethylenetriamine pentacetic acid (DEPTA); NTA; EHDP; ethylenediamine tetra(methylenephosphonic acid); and diethylenetriamine penta(methylenephosphonic acid). Photosensitizers can be added to the tooth whitening substance in an amount from about 0.1, 0.5, 1, 2, 3, 5, 7, 10 and/or less than about 10, 7, 5, 3, 2, 1, 0.5, 0.1 weight percent, based upon the total amount of tooth whitening substance. Superoxide may be generated using any of the above sensitizers in combination with an electron donor such as amines and amides— EDTA, DTPA, diethylene triamine pentaphosphonic acid, triethanolamine, triethylamine, tryptophan, tyrosine or acetanilide. In another embodiment nanometer scale zinc diode and titanium dioxide may be used as photosensitizers.

In some embodiments, it may be desirable that the illuminated toothbrush and whitening substance be "matched." That is, it is desirable that if the whitening substance exhibits enhanced or accelerated whitening function upon exposure to light of a certain wavelength or range of wavelengths, i.e. a band, then the wavelength of light emitted from the lighting unit of the toothbrushes described herein is the same or substantially so as that certain wavelength. For example, if a particular whitening substance is identified for use with the illuminated toothbrushes described herein, and if that substance exhibits enhanced effects upon exposure to light of a peak wavelength of 430 nm to 470 nm, then the toothbrush to be used in conjunction with that substance can emit light having a wavelength within the range of 430 nm to 470 nm.

4. Additional Oral Care Actives

Other oral care actives that can be used with the present invention to provide an oral care benefit include, but are not limited to: stannous ion; anti-microbial agents; anti-plaque agents; anti-inflammatory agents; nutrients such as minerals, vitamins, oral nutritional supplements; antioxidants; anti-viral agents; analgesic and anesthetic agents; H-2 antagonists; and additional actives such as insulin, steroids, herbal and other plant derived remedies, anti-neoplastics, and anti-gingivitis or gum care agents. These oral care actives can be added to the oral care substance in an amount from about 0.01, 1, 5, 10, 20, 30, 40 and/or less than about 40, 30, 20, 10, 5, 1, 0.5 weight percent based on the total amount of the oral care substance.

5. Oral Care Carries and Gelling\Agents

The oral care substances disclosed herein can comprise an orally acceptable oral care carrier. Additionally, some of the actives disclosed herein can also act as an oral care carrier. In some embodiments an oral care active such as a polymer can be used as a polymer oral care carrier to deliver improved substantivity of the actives, to further adhere the oral care active to the desired surface of the oral cavity and/or to improve delivery of an oral care active to the desired surface of the oral cavity. For some of the actives, the longer the active remains on the oral care surface, the greater the oral benefit that can be delivered. In one embodiment the oral care active is light activated, and therefore, use of a polymer which increases substantivity of the active on the oral surface allows for more exposure of the oral care active to light. Increased exposure time to the light can result an increase in the oral care benefit. An oral care carrier comprises one or more compatible solid or liquid filler diluents or encapsulating substances which are suitable for topical oral administration, and can improve the delivery of oral care actives to the surfaces of the oral cavity. The oral care carrier should be compatible with the actives used in the substances; "compatible" as used herein, means that the components of the substance are capable of being commingled without interaction in a manner which would substantially reduce the substance's stability and/or efficacy. In particular the oral care carrier can include a polymer carrier, such as those described in U.S. Pat. Nos. 6,682,722 and 6,589,512 and U.S. application Ser. Nos. 10/424,640 and 10/430,617. Examples of polymers suitable for use in the present invention include but are not limited to: silicone gums and resins, in particular silicone resins having a molecular weight of from about 1000 to about 10,000; dicarboxy functionalized polyorganosiloxanes; water soluble or water dispersible copolymers prepared by copolymerizing one or a mixture of vinyl pyrrolidone monomers (in particular, copolymers of vinyl pyrrolidone with vinyl acetate, vinyl propionate or vinyl butyrate) with one or mixture of C1-C19 alkyl carboxylic acid C2-C12 alkenyl ester monomer; carbopol; Gantrez; and/or polyvinylpyrrolidone.

In one embodiment of the present invention, the polymer carrier comprises as an essential ingredient at least one siloxane polymer functionalized with carboxylic acid groups, for application to polar surfaces such as teeth, ceramics, skin, fabrics, hair, glass and paper. The substances comprise at least about 0.1% of the carboxy functionalized siloxane polymer in a formulation that effectively deposits the polymer to the treated surface. The present polymers comprise a hydrophobic siloxane backbone and pendant anionic moieties containing carboxy groups and have the ability to deposit onto surfaces from aqueous-based formulations such as cleaning and detergent substances and from essentially non-aqueous based formulations. When applied to a suitable surface, the present substance comprising the carboxy functionalized siloxane polymers forms a substantially hydrophobic coating on the treated surface, the coating having prolonged retention thereon.

The carboxy functionalized siloxane polymers useful in the present invention are believed to attach themselves to polar surfaces and to form a coating thereon by electrostatic interaction, i.e., complex formation between the pendant carboxy groups of the polymer with cations or some other positively charged sites on the treated surface. For example, in the case of oral application it is believed the carboxy groups will interact with the calcium ions present in teeth. In the case of fabrics, the interaction may be with calcium ions or cellulose groups; in the case of hair or skin, with the protein residues; in the case of glass or ceramics, with calcium and other metal ions. The carboxy groups thus serve to anchor the siloxane polymer backbone onto a surface thereby modifying it to be hydrophobic.

The functional group pendant from the polysiloxane main chain comprises two carboxy groups, resulting in improved deposition and retention of the polymer particularly on surfaces such as teeth that contain positively charged calcium ions. The interaction between the carboxy groups and the tooth surface is electrostatic in nature in which the anionic carboxy groups form a complex with the positively charged calcium ions.

Dicarboxy acid functionalized polyorganosiloxanes useful in the present invention have the formula

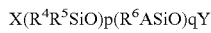

wherein
the X end group represents a triorganosiloxyl end group of formula $R^1R^2R^3SiO-$, or a Z end group wherein Z represents —OH;
the Y end group represents a triorganosilyl end group of formula $-SiR^3R^2R^1$ or a W end group wherein W represents —H;
$R^1$ to $R^6$, which may be identical or different, each represents a linear or branched C1-C8 alkyl or phenyl radical, preferably methyl;
A represents a dicarboxy acid radical of formula

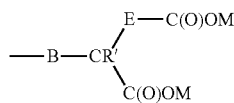

wherein
B represents an alkylene residue having from 2 to 30 carbon atoms, preferably from 3 to 8 carbon atoms, optionally substituted by one or more alkyl radicals having from 1 to 30 carbon atoms,
R' represents a hydrogen atom or an alkyl radical having from 1 to 30 carbon atoms,
E is nil or is an alkylene residue having from 1 to 5 carbon atoms, preferably from 1 to 3 carbon atoms, optionally substituted by one or more alkyl radicals having from 1 to 30 carbon atoms; and
M is H, a cation or an alkyl radical having from 1 to 4 carbon atoms optionally substituted with hydroxy or alkoxy groups;
p is an average value ranging from 0 to 1000, preferably from 0 to 500, more preferably from 5 to 200;
q is an average value ranging from 1 to 100, preferably from 1 to 50; and
the ratio of the number of Z and W end groups to the total number of end groups X and Y ranges from 0/100 to 75/100, preferably from 0/100 to 30/100.
In one embodiment, the p/q ratio is from 1/3 to 99/1 (corresponding to 1-75% of pendant diacid groups relative to the siloxyl units), in another embodiment the p/q ratio is from 1/1 to 10/1. The products where Z is —OH and/or Y is H, are by-products.

The cation salts of the dicarboxy radical can be alkali metal (sodium, potassium, lithium) salts, alkaline earth metal (calcium, barium) salts, non-substituted or substituted ammonium(methyl-, dimethyl-, trimethyl-, or tetramethylammonium, dimethylpiperidinium) salts or can derive from an alkanolamine(monoethanolamine, diethanolamine, triethanolamine).

In addition to the mono- or diester derivatives of the dicarboxy radical (M=alkyl), the present invention includes the amide and diamide derivatives.

The present dicarboxy functionalized siloxane polymers are generally prepared by a hydrosilylation reaction of a polyalkylhydrogensiloxane and an alpha-olefinic anhydride, the precursor of the dicarboxy A groups, with the aid of an effective amount of a hydrosilylation metal catalyst (platinum), as described for example, in U.S. Pat. Nos. 3,159,601; 3,159,662; and 3,814,730, followed by hydrolysis of the anhydride groups.

In particular, with respect to bleach delivery from an oral care substance such as dentifrice or mouth rinse, the present polymers having a hydrophobic polysiloxane backbone and pendant moieties containing dicarboxy groups are uniquely suited to facilitate delivery and retention of the bleaching agent on teeth for a period of time sufficient to provide a noticeable whitening benefit, particularly with repeated use of the substances. The present method of using a substantive polymer to deposit and retain the bleaching agent for a prolonged contact time thus represents a novel approach.

In another embodiment the polymer carrier is a vinyl pyrrolidone (VP)/vinyl acetate (VA) copolymer having 60/40 weight ratio of VP/VA and an average molecular weight ranging from about 1000 to about 1,000,000 available from BASF Corp and ISP. Copolymers having a VP/VA ratio ranging from about 30/70 to about 90/10 are also suitable.

The oral care substance of the present invention can be in many forms, including a gel, and in particular including an aqueous gel. A gel is a high viscosity matrix formed from gelling agents. If a gel form is used, a gelling can be used. The gelling agents that can be used in the present invention are safe for oral use, do not readily dissolve in saliva, and do not react with or inactivate the oral care compounds incorporated into them. Generally the gelling agent is a swellable polymer. Suitable gelling agents for use in the present invention include carboxypolymethylene,. carboxymethyl cellulose, carboxypropyl cellulose, poloxamers, carrageenan, Veegum, carboxyvinyl polymers, and natural gums such as gum karaya, xanthan gum, Guar gum, gum Arabic, gum tragacanth, and mixtures thereof. The gelling agent can be added to the oral care substance, and in particular to a tooth whitening substance in the form of a gel in an amount from about 0.1, 1, 2, 3, 5, 7, 10, 12, 15 and/or less than about 15, 12, 10, 8, 7, 5, 3, 2, 1, 0.5 weight percent based upon the total amount of the oral care substance.

Another treatment agent which can be used with the present invention is an optical coupling agent. These compounds provide increased optical access into underlying tissue by reducing the amount of light scattering at the tissue surface. Exemplary optical coupling agents include glycerol; glucose; propylene glycol; polyethylene glycol; polyethylene glycol; x-ray contrasting agents (Trazograph-60, Trazograph-76, Verogrann-60, Verografin-76, and Hypaque-60); proteins (hemoglobin, albumin); and combinations thereof. The optical coupling agents can also be used with additives such as ethanol and water (e.g., ethanol, glycerol and water).

Additional treatment agents may further include desensitizing agents (e.g., sodium citrate and potassium nitrate); gelling agents (e.g., sodium chloride and glycerol), sticky matrix materials (e.g., CARBOPPOL 974 NF); and conventional toothpastes. Materials which stabilize or adjust pH levels within the oral cavity may also be added as a treatment agent.

EXAMPLES

The following examples further illustrate the preferred embodiments within the scope of the present invention. These examples are given solely for the purpose of illustration and are not to be construed as limitations of the present invention as many variations of the invention are possible without departing from its spirit or scope. Unless otherwise indicated, all ingredients are expressed as a weight percentage of the composition.

TOOTHPASTE/DENTIFRICE EXAMPLES

Dentifrice compositions according to the present invention are shown below. These compositions are made using conventional methods.

Example Set 1

| Components | 8A | 8B | 8C | 8D | 8E | 8F |
|---|---|---|---|---|---|---|
| Color FD&C Blue#1 | | 0.300 | | | 0.200 | 0.200 |
| Carbomer 956 | 2.000 | | | 2.000 | 0.300 | 0.300 |
| Citric Acid | | | 0.180 | | | |
| Flavor | 0.900 | 1.100 | 1.000 | 0.900 | 1.200 | 0.800 |
| Saccharin | 0.300 | 0.400 | 0.450 | 0.400 | 0.300 | 0.350 |
| Glycerin | 10.000 | 30.000 | 30.000 | QS | | |
| Monosodium Phosphate | | 0.500 | | | 0.590 | 0.500 |
| Trisodium Phosphate | | | | | 1.450 | 1.400 |
| Xanthan Gum | | | | | 0.475 | 0.500 |
| Na Hydroxide (50% soln) | 1.100 | | | | | |
| PEG 40 SDIS | | | 1.240 | | | |
| Poloxamer 407, NF | | 15.000 | 15.000 | 5.000 | | |
| Powdered Polyethylene | | 20.000 | 15.430 | | | |
| Silica | | | | 10.000 | 20.000 | 15.000 |
| Sodium Stannate | | | 0.090 | | | |
| Sodium Fluoride | 0.243 | 0.243 | 0.243 | 0.243 | 0.243 | 0.243 |
| Sorbitol (70% soln) | | | | | 50.000 | 40.000 |
| Sodium Alkyl Sulfate (28% soln) | 3.000 | | | | 4.000 | 5.000 |
| Propylsuccinic Acid Polysiloxane Polymer | | 5.000 | | 3.000 | | 1.000 |
| Propylsuccinic Acid/ Propylene Glycol ester Polysiloxane Polymer | 3.000 | | 2.000 | | 4.000 | |
| Urea Peroxide | 10.000 | | | 4.000 | | |
| Hydrogen Peroxide (35% soln) | | 5.000 | 3.000 | | | |
| Triclosan | 0.300 | | | | 0.300 | |
| Cetyl Pyridinium Chloride | | | 0.530 | | | |
| Vitamin E | | | | | | 2.000 |
| Water, Purified USP | QS | QS | QS | | QS | QS |

Example Set 2

| INGREDIENT | Formula Wt/Wt % | Formula Wt/Wt % | Formula Wt/Wt % | Formula Wt/Wt % | Formula Wt/Wt % | Formula Wt/Wt % |
|---|---|---|---|---|---|---|
| Saccharin Sodium USP (a) | 0.320 | — | 0.50 | 0.70 | 0.50 | 0.50 |
| Trisodium Phosphate | 1.450 | — | — | — | — | — |
| Xanthan Gum NF | 0.475 | 6.00 | — | — | — | — |
| Sodium Fluoride USP | 0.243 | — | — | — | — | — |
| Carbomer 956/Pemulen | 0.300 | 2.00 | — | — | — | — |
| Monosodium Phosphate | 0.590 | — | — | — | — | — |
| Sorbitol Soln USP (70%) (b) | 62.242 | — | — | — | — | — |
| Silica Abrasive USP | 20.000 | 5.00 | — | — | — | — |
| Purified Water, USP (b) | 8.980 | — | 60.00 | 24.00 | 60.00 | 60.00 |
| Sodium Lauryl Sulfate 28% Soln | 4.000 | — | — | — | — | — |
| Flavor | — | — | — | 1.50 | — | — |
| Dye, FD&C Blue No. 1 Soln (c) | 0.200 | — | — | — | — | — |
| Dimethicone (linear PDMS) 10 cst | — | 80.00 | — | | | |

-continued

| INGREDIENT | Formula Wt/Wt % | Formula Wt/Wt % | Formula Wt/Wt % | Formula Wt/Wt % | Formula Wt/Wt % | Formula Wt/Wt % |
|---|---|---|---|---|---|---|
| PDMS (SE 30) | — | 7.00 | — | — | — | — |
| Ethanol | — | — | 32.50 | — | — | — |
| Sodium Tripolyphosphate | — | — | 2.00 | 5.00 | — | 5.00 |
| 60/40 PVP/VA | — | — | 5.00 | 5.00 | 5.00 | 5.00 |
| Propylene Glycol | — | — | — | 53.00 | 30.00 | 25.00 |
| Sodium Benzoate | — | — | — | 0.32 | — | — |
| Bezoic acid | — | — | — | 0.02 | — | — |
| Poloxamer 407 | — | — | — | 10.00 | 4.50 | 4.500 |
| Papain (Enzyme) | — | — | — | — | 0.002 | — |
| Glucose Oxidase | — | — | — | — | — | 0.005 |
| Total | 100.00 | 100.00 | 100.00 | 100.00 | 100.00 | 100.00 |

MOUTH RINSE EXAMPLES

Mouth rinse compositions according to the present invention are shown below. These compositions are made using conventional methods.

Example 1

| Ingredient | Weight % |
|---|---|
| Water | 29.000 |
| Propylene Glycol | 53.459 |
| Sodium Benzoate | 0.320 |
| Benzoic Acid | 0.021 |
| Sodium Saccharin | 0.700 |
| Propylsuccinic Acid Functionalized Polysiloxane (AMW = 1700) | 5.000 |
| Poloxamer 407 | 10.000 |
| Flavor | 1.500 |

Example 2

| Ingredient | Weight % |
|---|---|
| Water | 24.00 |
| Propylene Glycol | 53.46 |
| Sodium Tripolyphosphate | 5.000 |
| Sodium Benzoate | 0.320 |
| Benzoic Acid | 0.020 |
| Sodium Saccharin | 0.700 |
| 60/40 PVP/VA | 5.00 |
| Poloxamer 407 | 10.00 |
| Flavor | 1.500 |

Example 3

| Ingredient | Weight % |
|---|---|
| Purified Water | 76.638 |
| Glycerin | 23.000 |
| Flavor (Teaberry) | 0.120 |
| Saccharin | 1.018 |
| CPC | 0.074 |
| Poloxamer 407 | 0.050 |
| FD&C Blue #1 | 0.100 |

Example 4

| Ingredient | Weight % |
|---|---|
| Purified Water | 49.568 |
| 3% H2O2 | 25.000 |
| CPC | 0.053 |
| Poloxamer 407 | 0.050 |
| PVP/VA | 0.200 |
| Sucralose | 0.010 |
| Glycerin | 25.000 |
| Menthol | 0.040 |
| Methyl Salicylate | 0.07 |
| FD&C Blue #1 | 0.009 |

GEL EXAMPLES

Gel compositions according to the present invention are shown below. These compositions are made using conventional methods.

Example 1

| Ingredient | Weight % |
|---|---|
| Dimethicone (linear PDMS) 10 cst | 80 |
| PDMS (SE30) | 7 |
| Xanthan Gum | 6 |
| Pemulen | 2 |
| Silicone Dioxide Collodial | 5 |

Example 2

| Ingredient | Weight % |
| --- | --- |
| Ethanol | 32.50 |
| Water | 60.00 |
| Sodium Tripolyphosphate | 2.00 |
| Sodium Saccharin | 0.50 |
| 60/40 PVP/VA | 5.00 |

Example 3

| Ingredient | 8A | 8B | 8C | 8D | 8E | 8F | 8G |
| --- | --- | --- | --- | --- | --- | --- | --- |
| Flavor | 0.500 | 0.500 | 0.500 | 0.500 | 0.500 | 0.500 | 0.500 |
| Saccharin | 0.100 | 0.100 | 0.100 | 0.100 | 0.100 | 0.100 | 0.100 |
| Propylsuccinic Acid Polysiloxane Polymer (AMW = 1700) | 80.000 | 25.000 | 70.000 | | | 80.000 | |
| Propylsuccinic Acid Polysiloxane Polymer | | | | 75.000 | 66.000 | | 75.000 |
| Urea Peroxide | 10.000 | 15.000 | 20.000 | 15.000 | 15.000 | | |
| Triclosan | | | | | | 3.000 | |
| Cetyl Pyridinium Chloride | | | | | | | 1.00 |
| PEG 600 | QS | QS | QS | QS | QS | QS | QS |

Example 4

| Ingredient | Weight % |
| --- | --- |
| Glycerin | 70 |
| Carboxypolymethylene | 5 |
| Carbamide Peroxide | 10 |
| Water (pH 6.5) | 15 |

7. Chemical-Based Responsive Output elements or Devices

A variety of structures and mechanisms suitable for use with the present invention for dispensing of compositions as a chemical-based responsive output will now be described devices exist for delivering an oral care substance to the surfaces of the oral cavity including, but not limited to, dispensing or release of the substance from the sensor-responsive toothbrush. Generally, a sensor-responsive toothbrush utilizing a chemical-based output includes a reservoir or container defined within the body or housing of the toothbrush that contains one or more oral care substances. The substances may be in the form of a liquid, gas, semi-solid, or other suitable form. Preferably the substances are in flowable form, such as a solution or gel, and/or under pressure to assist in their discharge or release from the toothbrush. The oral care substances can in certain embodiments, be in solid form such as granular, pellets, or preferably in small particulate form. It is also contemplated to utilize one or more micro pumps to effect transfer of an oral care substance from the toothbrush to the oral cavity. The one or more oral care substances can be dispensed from the sensor-responsive toothbrush at nearly any location along the brush, however it is preferred that dispensing occur at the head and/or neck regions of the toothbrush. Dispensing can occur through one or more orifices or apertures provided in the housing or a component such as a bristle carrier along the exterior of the housing. In another embodiment, an oral care substance is delivered to an oral surface by a delivery system comprising a strip of material exposed or otherwise accessible along the exterior of the toothbrush. Applied or coated onto the strip of material is an oral care substance. The oral care substance can be uniform and continuously coated onto the strip of material. Alternatively, the oral care substance can be a laminate or separated layers of components, an amorphous mixture of components, separate stripes or spots or other patterns of different components, or a combination of these structures including a continuous coating of oral care substance along a portion of the strip of material.

The sensor-responsive toothbrushes described herein can provide a chemical-based output, which can dispense one or more oral care compositions. For these embodiments, the toothbrushes can utilize a dispensing system that includes one or more cartridges, each containing a particular oral care composition.

The cartridges may be manually or motor driven to dispense the oral care materials, either directly onto the applicator of a toothbrush, or through passages in the toothbrush onto or through an applicator. Preferably, the dispensing is motor-driven and controlled by the controller but it is contemplated that a signal can be provided to a user for the user to manually provide the responsive output such as by manually pumping a composition to effect dispensation of the composition. The applicator may be any suitable device for applying materials to teeth or to another device, including bristles, hollow dispensing tube (for application of the materials directly to the teeth/gums or to another device such as a toothbrush), sponge, and/or nubs (a knobbed, roughened, or multi-contoured surface for contacting teeth and/or gums). The dispensing system generally also includes a cartridge holder, and a dispensing actuator, as in a knob, button, or similar means.

Any suitable reservoir or cartridge may be utilized in the present invention. It should be understood that the reservoir or cartridge utilized may be fully or partially internal to the dispensing system, or fully or partially external to the system, and may or may not be removable from the system. Additionally, the reservoir or cartridge utilized may be permanent to the system, or may be disposable, including a single use disposable reservoir. Non-limiting examples of suitable reservoirs include positive displacement type reservoirs which are generally rigid-walled such as a cartridge, and also include pump-evacuated type reservoirs which are generally soft-walled such as sachets, bladders, and blisters.

The dispensing amount of any particular cartridge may be adjusted by any suitable means, non-limiting examples of which include varying the motor speed to the dispensing mechanism, and include changing the mechanical advantage of the dispensing mechanism (for example by substituting screws having various screw pitch or by utilizing different ratio gears for driving the screw). For other variations of cartridge designs, rate and amount of product can be controlled by means such as orifices, speed/timing relationships, pumps, etc.

Additional details of cartridges, dispensing systems and the like are set forth in U.S. patent application Publication No. 2003/0194678 filed Apr. 25, 2003.

Examples of strips which are suitable for use in the inventive method include, but are not limited to, the strips disclosed in U.S. Pat. Nos. 6,096,328, 6,136,297, 6,045,811, 5,989,569, 5,894,017, 5,891,453, 5,879,691, 6,277,458, 6,287,120 and 6,343,932.

The oral care substance can also be provided to the oral surfaces with a bleaching tray that is interchanged with a replaceable head assembly. Examples of trays suitable for use in the inventive method include, but are not limited to, those described in U.S. Pat. Nos. 5,846,058, 5,816,802 and 5,895,218, and other pre-loaded devices such as those described in U.S. Pat. No. 5,310,563.

Additionally, an applicator can be used to paint-on the oral care substance to the desired surfaces of the oral cavity. The applicator can be interchangeable with a replaceable head assembly. The delivery devices can comprise one for the upper teeth and one for the lower teeth. The delivery devices can be disposable, or reusable.

D. Kits and Replaceable Toothbrush Components

The sensor responsive electric toothbrush can be packaged as a kit comprising one or more oral care substances, each having or more responsive agents, and/or one or more replaceable heads containing a responsive output element, such as a light-emitting element. The oral care substances may be provided in the form of a dentifrice that is used with the toothbrush or packaged in a cartridge for dispensation from the toothbrush as previously discussed. Alternately, one or more replaceable heads comprising a chemical-based output and means for dispensing can be provided. The heads can thus be replacements or individually assigned to different members of a family. Color distinction is thus often a part of the different heads in a kit. Although the handle is discussed as battery powered, the invention also includes other well known power supplies such as cords for outlet connection or rechargeable batteries and an associated brush holder/charger (not shown). The kit may further include one or more packaged, light-activated oral substances, such as a packaged tooth whitening composition. Additionally, the kit can include other non-light activated oral care substances and toothbrush heads that do not comprise a light-emitting element.

Figure 25:
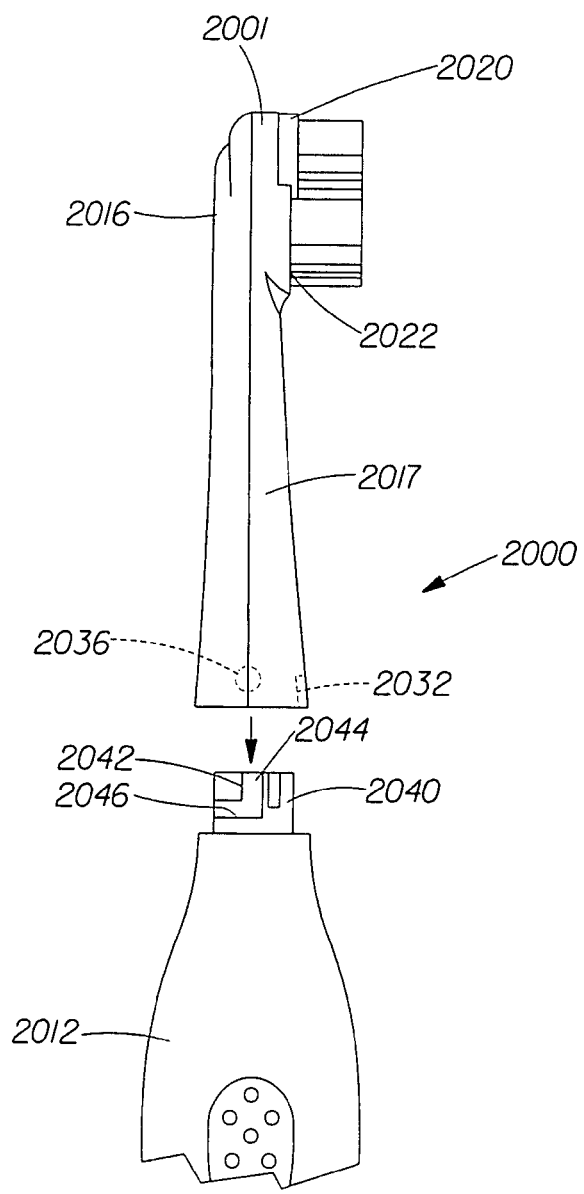
FIGS. 25 and 26 are partial side elevational views illustrating installation of a replaceable head and neck onto a handle or body portion of the sensor responsive illuminated electric toothbrush.
Figure 26:
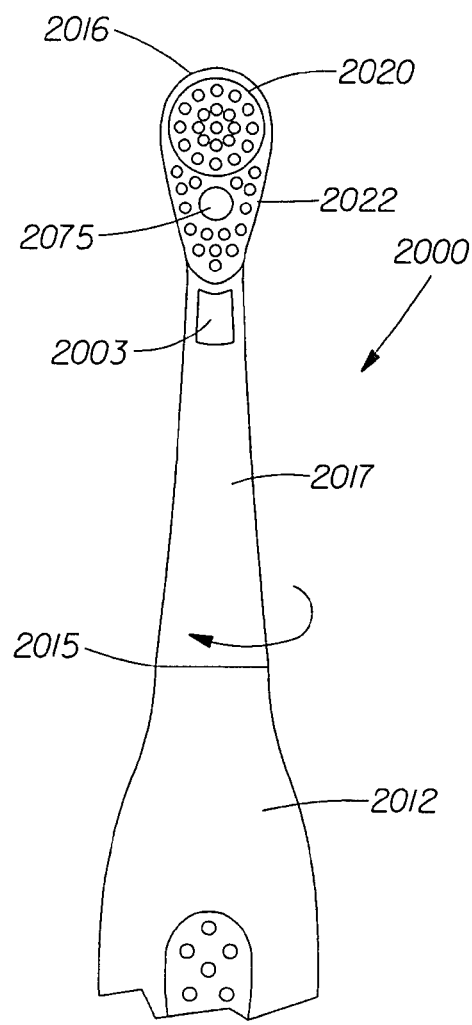

Referring now to FIGS. 25 and 26, a sensor-responsive toothbrush 2000 is shown. The toothbrush comprises a replaceable head 2016. The head 2016 further includes a moving bristle holder 2020 and a static bristle holder 2022. Disposed on the static bristle holder 2022 is a LED 2075. The sensor-responsive toothbrush 2000 further comprises one or more sensors such as 2001 and 2003. Although these sensors are shown as located on the replaceable head and neck component, the present invention includes the provision of one or more sensors located on the body or housing 2012 of the toothbrush 2000.

A neck 2017 separates from a handle 2012 at joint 2015. The neck 2017 has two small pins or projections 2036 [in phantom] located inside the neck end portion 2032. The small projections are dimensioned to fit into L-shaped slots 2042 found on a mating end portion 2040 of the handle 2012. The width of the L-shaped slots 2042 is slightly wider than the width of the small projections to enable the L-shaped slots to receive the small projections. The depth of the L-shaped slots is substantially equal to the height of the small projections so that the L-shaped slots can receive the small projections.

To connect the head and neck to the handle, the user aligns the small projections with a top surface 2044 of the L-shaped slots. The user pushes or presses the head 2016 down so that the small projections contact a bottom surface 2046 of the L-shaped slots 2042. When the small projections have contacted the bottom surface 2046 of the L-shaped slots, the user then turns the head 2016 and/or the neck 2017 approximately 90 degrees with respect to the handle 2012 locking the head into place, as seen in FIGS. 25 and 26. A top surface of each of the projections becomes locked under a top surface of each of the L-shaped slots 2042. The user thus exerts a press-and-twist action on the cooperating pins and guide slots to put the head into a fully attached disposition on the handle and realize a locking engagement between the two.

One or more electrical contacts are provided along the mating region of the neck and the handle to provide a releasable electrical connection there between.

Generally, the present invention relates to an oral care implement for use in the mouth having a replaceable or removable head and/or neck and one or more electrical elements on the brush head, including, but not limited to, light-emitting elements and/or one or more sensors. Such oral care implements can include, but are not limited to electric toothbrushes, powered flossers, tooth polishers, gum massagers etc. For simplicity sake hereinafter the present invention will be discussed as embodied in a sensor responsive electric toothbrush. Such electric toothbrushes can be used in personal hygiene to clean one's teeth and gums using a motorized movement, while the electrical element is activated, such as a light-emitting element which can illuminate the region of brushing, including the teeth and/or gums. The present invention includes any type of electrically powered elements used or provided on the head. Furthermore, the present invention relates to the use and incorporation of selectively engageable electrical connectors in an electric toothbrush having a removable brush head and that provides electrical communication between the head of the toothbrush and the handle of the toothbrush. The head of the toothbrush can further comprise a neck, to which the handle of the toothbrush can be attached. Further, the handle of the toothbrush can comprise a neck, to which the head of the toothbrush can be attached. For simplicity hereinafter the connections discussed will be between the head and the handle of the toothbrush. However, it should be appreciated that this discussion also includes connections between the head and the neck, and/or a head and neck assembly connecting to the handle and/or the body. All of these connections have the similar elements, but a different location of the connection along the length of the toothbrush.

In one embodiment, a sensor responsive illuminated electric toothbrush is provided that includes an elongated handle, a head, and a neck extending from the head to form a head and neck assembly. This head and neck assembly can be attached to the handle. The present invention includes embodiments in which the head and neck as a single integral assembly, are removable from the handle of the toothbrush. However, it is contemplated that the neck and handle can also be an assembly, from which a head is removable. Provided along the mating or engagement regions of the removable portions is the severable electrical connector described herein. One or more electrical elements such as light-emitting elements can be disposed on the head, adjacent to, on, or in one or more static or moving bristle holders or any combination thereof. The bristle holders may have bristles disposed thereon, and the bristles may be formed into one or groups of tufts. These aspects are described in greater detail herein.

The toothbrushes further comprise an electrical connector. An electrical connector is a system of components on the head, neck and/or handle of an electric toothbrush that when connected provides an electrical path and electrical communication between the head and the handle. As the head is removable from the handle portion of the toothbrush, the electrical connector can be designed such that the electrical connection can be severed or disengaged upon removal of the head and can be readily reconnected upon reattachment. An electrical connector comprises at least one electrical input and at least one electrical output. Multiple electrical inputs can be provided where, for example, a multi-color LED is provided on the toothbrush head. The electrical connector can include, but is not limited to, components which come into mechanical contact with each other "contacts", inductive components which electrically connect the head to the handle via a magnetic field, and capacitive components which electrically connect the head to the handle with an electric field created when a capacitor is formed. Provided along the region of engagement between the handle or body and the head is an electrical connector, examples of which are described herein. The toothbrush can also have more than one connector. It is also contemplated that if a neck extends from either the head and/or the handle, a portion of the connector can be disposed on the neck.

Providing a readily separable engagement configuration between a brush head, and a handle in an electric toothbrush offers several advantages. First, the brush head or handle for that matter may be easily replaced. The brush head may be easily interchanged with another brush head depending upon the particular preferences of a consumer. Furthermore, such quick and simple engagement provides ease of assembly, and also promotes storage and shipping concerns in that the relatively long length of the brush may be significantly reduced In certain embodiments, a toothbrush having a removable head utilizes a member projecting outward from one of the handle or head portions of the toothbrush that is received by a corresponding recess, slot, or receiving region defined in the other portion of the toothbrush. The member and receiving region cooperate with one another to provide selective removal of the head from the handle, and reattachment of the head to the handle. In such a configuration, an electrical connector is positioned proximate to the member and its receiving region. For example, if the connector includes two electrically conducting contacts, a first contact can be disposed on the member and the second contact can be disposed within the receiving region. The contacts are positioned such that upon attachment of the head to the handle and thus, engagement of the head within the receiving region, the contacts are positioned in electrical communication with each other thereby providing an electrical pathway between the handle and the head of the toothbrush.

In an alternate embodiment, the engagement assembly between the housing and brush head may utilize a screw or threaded configuration in which one of the housing and brush head includes a radially projecting screw member, and the other defines a groove or recessed region that is configured to receive the projecting screw member. A corresponding electrical connector is provided, for example electrical contacts can be disposed on the mating surfaces of the engagement assembly.

Other engagement configurations can be used for providing a sensor-responsive toothbrush having a removable head and handle. For example, the present invention includes, but is not limited to engagement configurations utilizing a male-female arrangement, a releasable locking pin arrangement, a releasable detent arrangement, a snap-fit arrangement, a friction fit arrangement, and combinations of these configurations. The severable electrical connector can be provided between the head and handle portion, and have components of the connector adjacent or within the regions of engagement or mating between the head and handle portion. However, it is contemplated that the head components of the connector can be received within the handle portion of the toothbrush and/or the handle components of the toothbrush can be received within the head portion of the toothbrush.

In any or all of the embodiments herein, one or more connector wiping elements can be provided that serve to wipe the electrical connector face of one or more of the connectors as the head is re-attached to the handle of the toothbrush. Such a wiping element is provided and positioned such that upon engagement of the head and handle, the wiping element passes over and essentially wipes the outer face of the electrical connector. This action serves to clean the connector face and remove any water or debris accumulated thereon. The wiping element can be formed from nearly any element, such as, but not limited to, a pliable rubber or other elastomeric material.

In accordance with the present invention, some type of releasable engagement is utilized between the drive shaft and one or more movable bristle carriers disposed or otherwise retained along the brush head. For example, a "snap-fit" engagement assembly could be utilized between an end of a drive shaft extending within the brush head, and a movable bristle carrier disposed on the brush head. It will be appreciated that a releasable engagement assembly be utilized at some location or point in the drive mechanism so that the brush head and handle can be readily separated from one another.

In certain embodiments of the toothbrush wherein the components of the connector includes contacts, the contacts can engage one another directly, in a face-to-face fashion as the head is engaged with the handle of the toothbrush. In certain embodiments, the faces of the respective contacts slide across each other, or at least partially so, during the engagement process. The various contacts may be in the form of relatively flat surfaces that contact each other to provide electrical communication. Or, the contacts may utilize a male-female connection as known in the art, including a pin-socket or plug-receiver configuration. The contacts may also utilize sloping or ramp surfaces that contact each other, or depending upon the particular application, may engage each other with relatively large contacting forces due to the ramped configuration. Alternately, or in addition, the contacts may include one or more spring members or other biasing members that impart a force to one or both contacts to further promote the establishment of electrical communication between the contacts. However, the connectors may use the aforementioned designs to come into electrical communication, thereby providing electrical power to the electrical element disposed on the head of the toothbrush, without having mechanical connection i.e. electrical communication established by induction or capacitance. Regardless of the type of connector, once the head and handle are engaged with one another, the connectors are in a configuration and position to provide electrical communication is provided between the head and the handle.

A wide array of connector designs, shapes, and configurations may be utilized in the toothbrushes according to the present invention. In one aspect, a sliding rail configuration is used in which one or more rails are provided on either the brush head or handle, and a receiving slot or recessed region is defined in the other, e.g. brush head or handle, that is of a size and orientation to receive the rails when the brush head and handle are engaged with each other. Contacts can be incorporated in these one or more rail(s) and slot(s) to provide electrical communication between the brush head and handle when the head engages the handle. Specifically, one or more pairs of the contacts are incorporated directly on the exposed surfaces of the rail(s) and slot(s). The respective contacts can be aligned and positioned such that upon final engagement between the brush head and the handle, the contacts provide electrical communication between the brush head and the handle.

In another embodiment, one or more contacts are positioned on side posts or otherwise outwardly projecting members of a brush head or handle that, upon engagement with a corresponding structure provided on the other head or handle, are in electrical communication with one or more additional contacts. Additionally, the handle and/or head, and/or portions of the handle and/or head can comprise electrically conductive substrates such that the handle and/or the head, or portions thereof, can be the electrically conductive contacts. Regardless of the contact placement, the resulting electrical communication enables electrical power to be transferred from the handle region to the brush head of the toothbrush.

In yet another embodiment, electrical communication is established by an axial configuration in which the respective contacts are brought into electrical communication with one another by rotating one of the brush head or handle portion with respect to the other. This configuration may be achieved with a variety of arrangements of electrical contacts. For example, circular, semi-circular, or arcuate shaped contacts may be used. The contacts may be appropriately positioned on engaging regions of the brush head and the handle.

In yet another embodiment electrical communication is established between the head and the handle by induction. In this embodiment the head has a secondary coil which is connected to the electrical element disposed on the head of the toothbrush, and the handle has a primary coil which is connected to the battery. When the head and handle are connected, the primary coil and secondary coil are magnetically coupled to transfer electricity. Further electrical communication can be established between the head and the handle with capacitance by including the appropriate conductive materials in the handle, which are further connected to the battery, and the head, which are further connected to the electrical element disposed on the head. When the head is connected to the handle the two pieces of conductor are separated by a distance such that the two pieces of conductor form a capacitor.

Material selection for the components of the connector is also another important aspect of the present invention. Generally, a wide variety of metals and non-metallic materials may be used for the components of connectors. Suitable metals include, but are not limited to copper, platinum, silver, nickel, aluminum, gold, tungsten, and alloys of these metals.

Electrically conductive non-metallic materials can be used such as electrically conductive polymers. The term "electrically conductive non-metallic materials" as used herein includes materials comprising one or more non-metals and one or more metals, such as polymeric compositions containing metal particles. Often such compounds are made by mixing solid conductive particles such as carbon black, stainless steel fibers, silver or aluminum flakes or nickel-coated fibers with electrically insulating bulk thermoplastics, for example polystyrene, polyolefins, nylons, polycarbonate, acrylonitrile-butadiene-styrene co-polymers (ABS), and the like.

Recently, there has been an increased interest in replacing carbon black or metal particle-filled compounds of the above-described type with intrinsically electrically conductive polymers and their blends with common insulating polymers including, but not limited to polyanilines. Polyaniline (or abbreviated PANI) and its synthesis and the preparation of the electrically conductive form of this polymer by, for example, contacting polyanilines with protonic acids resulting in salt complexes has been described in the prior art. Additionally, electrically conductive polymers are known and used in industrial settings, particularly in the manufacture of electronic component parts. Some examples of electrically conductive polymer compositions are illustrated in U.S. Pat. Nos. 5,256,335; 5,281,363; 5,378,403; 5,662,833; 5,958,303; 6,030,550; and 6,149,840. Particularly attractive electrically conductive polymer compositions for use in the connector assemblies described herein include those polymers described in U.S. Pat. Nos. 5,866,043 and 6,685,854. The term "electrically conductive non-metallic materials" as used herein also includes these types of compositions.

Another electrically conductive substrate suitable for use in the present invention is discussed in U.S. Pat. Nos. 6,291, 568, 6,495,069, and 6,646,540. This substrate has a first level of conductance when quiescent, or inactive, and a second level of conductance resulting from a change of stress; i.e. mechanical or electrical stress. The mechanical stress can include stretching and/or compressing. This substrate comprises a granular composition, each granule of which comprises at least one substantially non-conductive polymer and at least one electrically conductive filler. The conductive filler can be one or more metals, other conductive or semi-conductive elements and oxides or intrinsically conductive semiconductive inorganic or organic polymers. The granules are typically up to 1 mm, and the granule (conductor) to polymer volumetric ratio is suitably at least 3:1. It is contemplated that other substrates which conduct electricity when compressed are suitable for use in the present invention.

As previously noted, the toothbrushes can employ one or more electrically powered elements incorporated or otherwise included in the brush head that utilize a source of electrical power. In the toothbrushes described herein, an electrical power source, e.g. one or more batteries, is retained within the handle position of the toothbrush. The electrical connectors described herein establish and provide electrical communications between the brush head and the electrically powered elements requiring electrical power disposed thereon, and the power source, typically residing in the handle of the toothbrush.

E. Methods of Use

Figure 24:
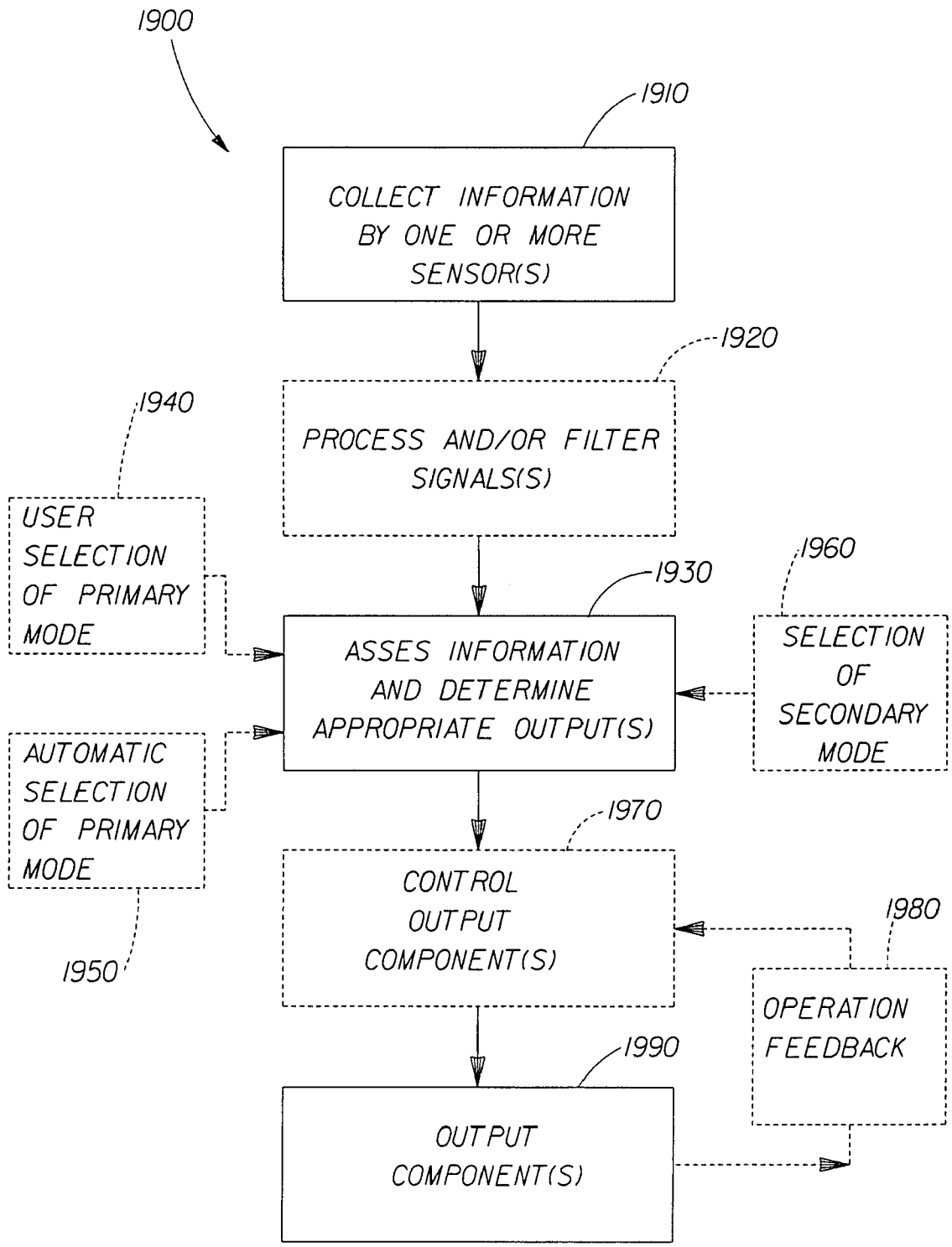
FIG. 24 is a flowchart depicting a representative process by which the sensor-responsive toothbrushes operate.

In certain embodiments, a preferred embodiment sensor-responsive toothbrush as described herein can operate as follows. FIG. 24 schematically illustrates a process flowchart depicting a representative operation of a toothbrush as described herein. The dashed lines denote optional operations. Referring to FIG. 24, information is collected 1910 by one or more sensors utilized by the toothbrush. As previously described, such sensors are incorporated or otherwise provided on the toothbrush. The information collected or obtained by the one or more sensors generally relates to the oral cavity of the user, although it can relate to other conditions such as the brushing habits of the user. Typically, the information pertains to one or more conditions in the oral cavity, the presence of one or more substances, chemicals, or agents in the oral cavity, or combinations of these aspects. The one or more sensors generate a signal or set of signals indicative of the collected information. The signals are typically low voltage or low amperage electrical signals as known in the art.

The toothbrushes can optionally comprise one or more components for processing or filtering 1920 the signal(s). For example, an archiving (for storing data such as a history of detected conditions or brushing habits) or delay function may be utilized which can further be used with a statistical routine or algorithm to process and/or filter the signal(s).

The one or more signals are then analyzed and appropriate output actions determined 1930. The analysis is preferably performed by one or more microprocessors incorporated in the toothbrush. The analysis may be optionally performed in conjunction with one or more external parameters that can originate from the user or, the toothbrush itself. For example, a primary mode selection can be performed by either the user 1940 or by the toothbrush 1950. The primary mode selection can for instance be with regard to (i) whether the toothbrush is to assess the condition of the oral cavity, (ii) whether the toothbrush is to detect the presence of any agents or markers in the oral cavity, or (iii) a combination of these objectives. A further mode selection can optionally be made, such as a secondary mode selection 1960. This selection can in certain embodiments, dictate or specify particular objectives based upon the primary mode selection. For example, if the primary mode selection is directed to identifying the conditions within the oral cavity, the secondary mode selection could be with regard to (i) a specific type of caries output is to be directed toward, (ii) a specific type of whitening action the output is to perform, . . . etc.

Upon assessing the information from the one or more sensors, and determining the appropriate responsive output(s) and optionally further making such determination in conjunction with external parameters such as mode selection, a signal is transmitted to the one or more responsive output components of the toothbrush. The signal governs 1990 the responsive output component(s) in accordance with the assessment and determination previously made.

The preferred embodiment operation can also include an optional feedback loop in which a signal indicative of the responsive output component or the operation or action of the responsive output component is directed to a control routine or algorithm such as block 1970 and/or 1980. Upon deviation of the output or action of the output component, the control routine can appropriately adjust the output or action of the output component to reduce the deviation, if so desired.

Figure 27:
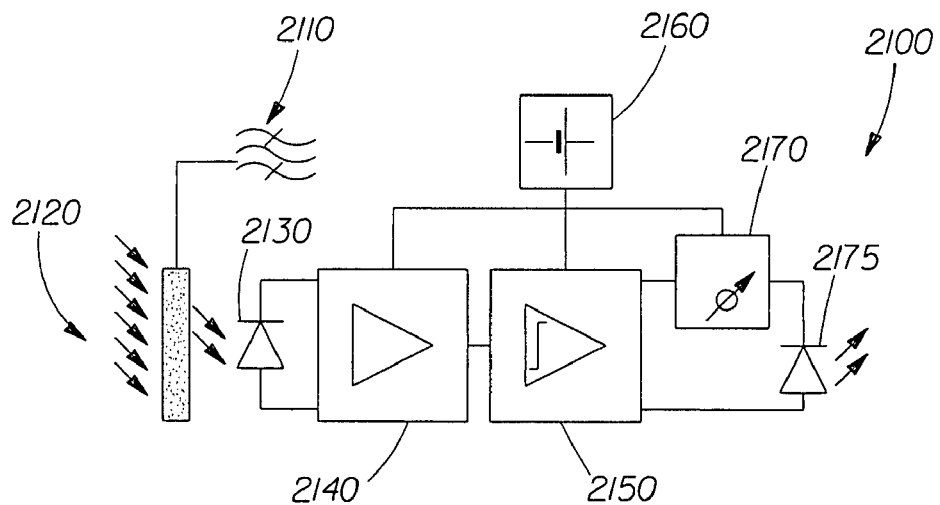
FIG. 27 is an electrical schematic for an embodiment of the sensor-responsive toothbrush.

The following simplified electrical schematics further illustrate operation and configuration of embodiments of the sensor-responsive toothbrushes described herein. FIG. 27 illustrates a system 2100 comprising one or more sensors such as a light sensor 2130 adapted to sense or detect light or changes in light characteristics, denoted by 2120, associated with a condition or agents within the oral cavity 2110. The sensor(s) 2130 provide a signal that can be processed or filtered by one or more of an amplifier 2140 and a filtering element 2150. The system 2100 further comprises an output component such as a light-based output component which can be in the form of an LED 2175. One or more capacitors, batteries, or electrical power supplies denoted by 2160 and 2170 can be utilized to power or drive the noted elements or components in system 2100.

Figure 28:
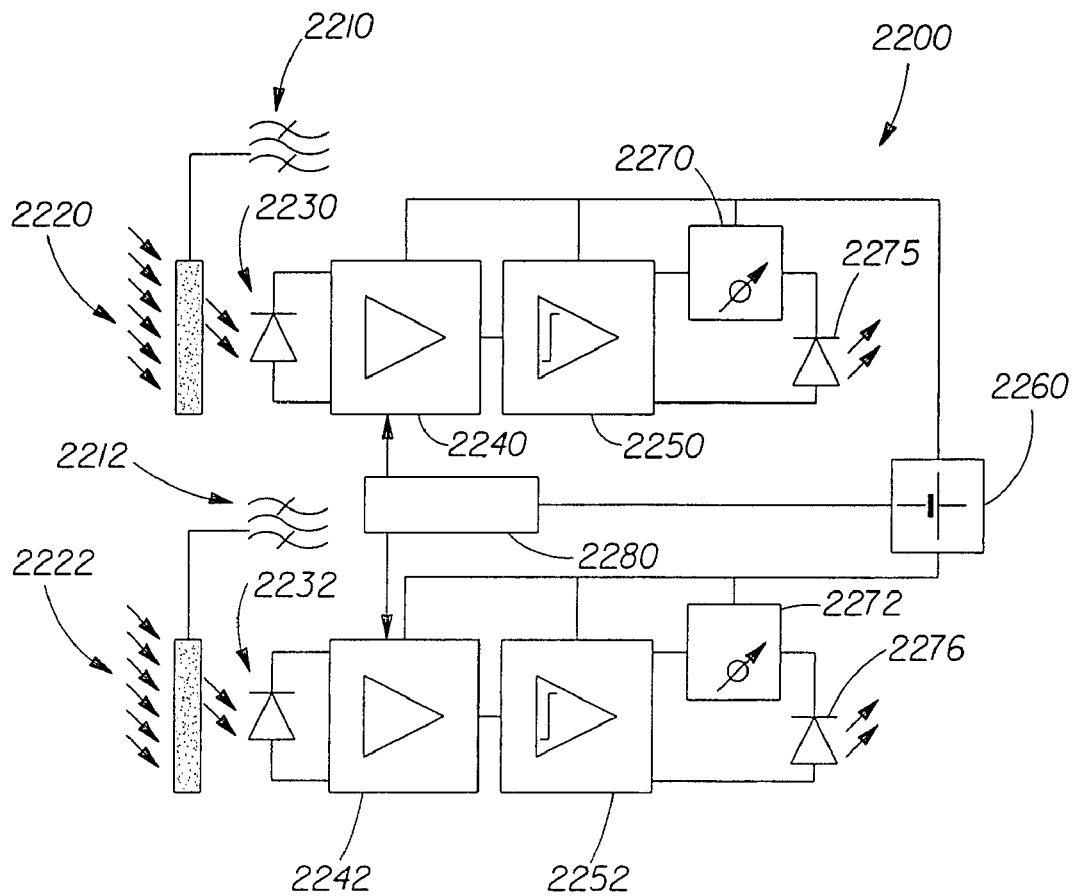
FIG. 28 is an electrical schematic for another embodiment of the sensor-responsive toothbrush.

FIG. 28 is a simplified electrical schematic for a dual function sensor-responsive toothbrush in accordance with the present invention. FIG. 28 generally includes two of the previously described systems denoted in FIG. 27, the operation of each being governed by a control unit or timer. FIG. 28 illustrates a representative schematic for the previously noted AM/PM toothbrush. More specifically, FIG. 28 illustrates a system 2200 comprising one or more sensors such as a light sensor 2230 adapted to sense or detect light or changes in light characteristics, denoted by 2220 associated with a condition or agents within the oral cavity 2210. The sensor(s) 2230 provide a signal that can be processed or filtered by one or more of an amplifier 2240 and a filtering element 2250. The system 2200 further includes an output component such as an LED 2275. One or more charge storing or power modules denoted by 2260 and 2270 can be utilized to provide power.

The system 2200 further comprises one or more secondary sensors such as a light sensor 2232 adapted to sense or detect light or changes in light characteristics, denoted by 2222 associated with another or secondary condition or agents within the oral cavity, identified by 2212. The secondary sensor(s) 2232 provide a signal that can be processed or filtered by one or more of an amplifier 2242 and a filtering element 2252. The system 2200 further includes an output component such as an LED 2276. One or more charge storing or power sources denoted by 2260 and 2272 can be utilized.

The system 2200 further comprises a controller, which can be in the form of a timer 2280, that governs which portion of the system operates and at what times. For example, and in the case of an AM/PM toothbrush, the timer 2280 can activate the upper portion of the system 2200 to detect certain conditions or agents that may have an increased importance at one time, such as the morning, and then, activate the lower portion of the system to detect certain conditions or agents that may have an increased importance at another time, such as the evening. Non-limiting applications of the system 2200 can include a morning phase in which the sensor 2230 detects markers or signals in the oral cavity indicative of malodor, and then activation of the output 2275 to address the malodor. Such output can include dispensing of a breath freshening composition or emission of light at a wavelength designated to reduce such malodor by, for example, killing bacteria. An evening phase is contemplated in which the sensor 2232 detects markers or signals in the oral cavity indicative of another condition such as discoloration of teeth. Upon sensing such discoloration for example, the output 2276 is activated to address the discoloration. Alternatively, the treatment regimen associated with each phase can be user selected and automatically provided by the toothbrush at the appropriate time. Remedial outputs can include for example emission of light at a wavelength designated to reduce such discolorations, or dispensing of an oral care composition that serves to reduce such discoloration. The sensor responsive electric toothbrush of the present invention can be used to deliver an oral benefit when used alone or in combination with an oral substance. In some embodiments the teeth are pre-treated with the oral care substance. This pre-treatments allows the oral care substances to absorb further into the oral care surface, such as the teeth, and therefore can increase the resulting oral care benefit when the oral surfaces are exposed to light.

In one embodiment, the invention includes a method wherein a uniform coating of an oral care substance can be applied onto a delivery device and then the oral care substance can be applied to the desired oral surface, such as a plurality of adjacent teeth, the gums, and/or any other surface of the oral cavity by use of the sensor-responsive toothbrush. The toothbrush is then removed from the oral surface, leaving behind some amount of the oral care substance on the oral surface. The portion of the oral care substance that remains on the teeth after the delivery device, such as a strip is removed can be from about 0.1, 0.5, 1, 2, 5, 10, 15, 20, 30, 40, 50, 60, 70, 80, 90% to about 100, 90, 80, 70, 60, 50, 40, 30, 20, 15, 10, 5% of the tooth whitening substance. The teeth are then brushed using the sensor-responsive toothbrush, exposing the surfaces of the oral cavity to the emissions from the head of the toothbrush. Additionally, a dentifrice can be used with the sensor-responsive toothbrush to clean the surfaces of the oral cavity. The surfaces of the oral cavity can be cleaned with a dentifrice prior to and/or after the application of the oral care substance if desired.

In another embodiment, the invention includes a method for whitening the teeth. The method includes providing a sensor-responsive toothbrush comprising a tooth whitening substance and applying the substance via the toothbrush to a plurality of teeth, or alternatively, applying the substance directly to the teeth and then, if desired, placing a delivery device such as a tray and/or a strip of material over the substance. The sensor-responsive toothbrush can be utilized to detect when a whitening operation is complete. The tooth whitening substance contains can contain from about 5% to about 50% of a tooth whitening active, and the substance is placed into contact with the teeth. The delivery device can remain on the teeth for from about 2, 4, 6, 8, 10, 15, 20, 25, 30, 35, 40, 45, 50, 55, 60 to less than about 60, 55, 50, 45, 40, 35, 30, 25, 20, 15, 10, 5 minutes. The delivery device is then removed, and at least a portion of the tooth whitening substance remains on the teeth. The portion of the tooth whitening substance that remains on the teeth after the strip is removed can be from about 0.1, 0.5, 1, 2, 5, 10, 15, 20, 30, 40, 50, 60, 70, 80, 90% to about 100, 90, 80, 70, 60, 50, 40, 30, 20, 15, 10, 5% of the tooth whitening substance.

In another embodiment the delivery device is a strip of material with a uniform coating of a tooth whitening substance disposed thereon. The strip of material is applied to the teeth and the delivery device can remain on the teeth for from about 2, 4, 6, 8, 10, 15, 20, 25, 30, 35, 40, 45, 50, 55, 60 to less than about 60, 55, 50, 45, 40, 35, 30, 25, 20, 15, 10, 5 minutes. When the strip of material is removed from the teeth, the strip releases from about 0.1 to about 80% of the tooth whitening substance, leaving a plurality of teeth with a coating of tooth whitening substance disposed thereon. The teeth are then brushed with the sensor responsive electric toothbrush comprising a head, a handle, a movable bristle holder, and a light-emitting element which is disposed on and emits light from the head of the toothbrush. The teeth can be brushed with the electric toothbrush for from about 30 seconds, 1 minute, 1.5 minutes, 2, minutes, 4, minutes, 5 minutes, 8 minutes and/or less than about 8 minutes, 5 minutes, 4 minutes, 3 minutes, 2 minutes, 1.5 minutes, 1 minute, 30 seconds. The light-emitting element can emit light having a wavelength of from about 420 to about 470 nm. This method can be performed from about 1 to about 4 times a day, for about 1 to about 8 weeks. Additionally, this method can be used to replace an every day oral care regimen, and can be used continuously to reduce and prevent staining of the teeth.

In another embodiment a uniform coating of the tooth whitening substance is disposed on the teeth via a delivery device or an applicator, and at least a portion of the tooth whitening substance is allowed to remain on the teeth overnight. The teeth can be brushed with a sensor responsive lighted electric toothbrush according to the present invention for from about 30 seconds, 1 minute, 1.5 minutes, 2, minutes, 4, minutes, 5 minutes, 8 minutes and/or less than about 8 minutes, 5 minutes, 4 minutes, 3 minutes, 2 minutes, 1.5 minutes, 1 minute, 30 seconds.

In yet another embodiment a rinse is used to treat the surfaces of the oral cavity either prior to and/or after the exposure to the emissions from the sensor responsive electric toothbrush. The rinse comprises a whitening active and a polymer which gives substantivity to the tooth whitening active, and/or helps adhere the tooth whitening active to the surfaces of the teeth. The teeth are then brushed using the earlier described oral care implement; exposing the surfaces of the oral cavity to the emissions from the head of the oral care implement.

The aforementioned methods can be repeated from about 1, 2, 3, 4 to about 5, 4, 3, 2, 1 times a day for from about 1 day to about 8 weeks. Additionally, the aforementioned methods can be used indefinitely, for example in place of an every day oral care regimen. In addition to removing stains, plaque and bacteria, if the methods are used in place of an every day oral care regimen, additional staining of teeth, plaque, and/or caries may be prevented from forming.

A sensor-responsive toothbrush according to the invention can be employed for application of single-wise and/or multi-wise treatment procedures, e.g., twice per day for a few weeks or a month. The toothbrush of the present invention can be used with a variety of output responsive agents, such as chromophores and optical couplers, to improve effectiveness. These agents can be part of an oral appliance system comprising a treatment agent for applying to the oral cavity and an oral appliance such as a light-emitting toothbrush or a light-emitting mouthpiece. In one embodiment, the treatment agent is applied to the oral cavity in the form of a paste, film, liquid rinse, spray, or combination thereof.

The sensor-responsive toothbrush of the present invention can be used for a variety of photodynamic and phototherapeutic treatments in and around the oral cavity. These responsive outputs can be provided in response to a sensor input or may be automatically applied based upon the date/time of toothbrush use as programmed by the manufacturer or selected by the user. These treatments are based on several biophysical phenomena that result from delivering light energy in the range of about 280 to 3000 nm with power densities in the range of about 1 to 10000 mW/cm and are collectively referred to as biostimulation. In a preferred embodiment, biostimulation is effected with an energy flux in the range of about 1 $J/cm^2$ to 1000 $J/cm^2$, and in an even more preferred embodiment in the range of about 10 $J/cm^2$ to 100 $J/cm^2$.

Biostimulation can include, for example, increase in blood and lymph microcirculation of gingiva, tongue, salivary glands and ducts, tonsils, vocal cords, lips, cheeks, perioral facial skin, and other tissue due to light absorption by endogenous porphyrins, cytochroms, and tissue molecular oxygen. The light absorption can induce photo stimulated nitric oxide (NO) which causes dilatation of blood and/or lymph vessels and can also induce $Ca^{2+}$ storage in cell mitochondria and activation of $Ca^{2+}$ dependent ATPase in vascular smooth muscle cells which causes photo attenuated sympathetic vasomotor nerve activity. These processes activate a tissue drainage function; endothelium cells and endot-helial leukocytes proliferative potency; and the formation of a new capillary net that helps regeneration of oral cavity epithelium, gingival tissue, neural tissue, skin collagen, and other tissue. In addition, the combined action of light therapy with heating can also cause activation of blood and lymph microcirculation of above mentioned tissues and glands.

Other effects include activation of blood microcirculation in tooth pulp due to light concentration in the tooth pulp caused by waveguide light propagation through enamel and dentin, and a corresponding increase in calcium ion flux from pulp to enamel through the protein matrix, which assists calcium ions to fill vacancies in the hydroxyapatite structure.

Biostimulation can also include an increase in local (oral and surrounding tissues) macrophage activity and fibroblast, osteoblast, and odontoblast proliferation. This can result in epithelium, collagen, nerve tissue, and hard tooth tissue regeneration. An additional important benefit can also be the killing of bacteria, fungi, and viruses. This effect is induced by light action on endogenous porphyrins, molecular oxygen, incorporated exogenous dyes, mineral photosensitizers, and/or mineral photocatalysts.

Another desirable effect is the normalization of oral cavity pH caused by bacteria activity reduction and oral lesions (stomatitis) healing which leads to decrease in oral tissue swelling and in osmotic pressure.

The systemic beneficial (biostimulation) effect can also provide improved immunocompetence via blood and lymph irradiation. In particular, biostimulation can cause light improved immunocompetence of blood and lymph macrophages, which produce superoxide and nitric oxide; erythrocyte membrane elasticity; and lymphocyte proliferation activity. Other whole body effects can include light-induced control of human circadian rhythms.

The sensor-responsive toothbrushes of the present invention can be used for a variety of other therapeutic treatments which include directly radiating areas of the oral cavity with optical radiation. Both the light-emitting toothbrush and the light-emitting mouthpiece can be used to radiate hard and/or soft tissue in the oral cavity with or without additional treatment steps such as heating, vibrating, and applying treatment agents such as chromophores and optical coupling agents.

In one embodiment the light-emitting toothbrush and/or the light-emitting mouthpiece can be used to treat dental problems such as gum bleeding, tooth hypersensitivity, tooth pain, bone problems, enamel degeneration, caries, root canal inflammation, and periodontal problems by radiating hard and/or soft oral tissue. The therapy can include directly radiating the problem area, and in some cases using heat or chromophores to assist with treatment.

F. Examples of Some Responsive Outputs and Uses of the Sensor-Responsive Toothbrush Reduction of gum bleeding. Gum bleeding is mostly caused by a poor proliferation of epithelial cells and other connective tissues. The sensor-responsive toothbrushes of the present invention can provide light irradiation and soft heating to activate increased fibroblast proliferation, causing regeneration of epithelium, collagen, and other connective tissue that helps stop gum bleeding. Light acceptors include endogenous porphyrins, cytochromes, and molecular oxygen and therefore irradiation of oral mucus and underlining tissue at power density of 1-1000 mW/cm2 and daily doses of 0.06-30 J/cm2 at the wavelengths corresponding to porphyrins, cytochromes, and molecular oxygen are preferred. Blue light (400-430 nm) is very effective for porphyrin excitation; green light (540-580 nm) and red light (600-650 nm) are also capable of activating porphyrins. In particular, coproporphyrins can be excited at the wavelengths: 402±20 (extinction at maximum≈480), 495O±20, 540+30 (extinction at maximum≈17), 580±30 (extinction at maximum≈6), 623±20 nm; and cytochroms: cytogem (the prosthetic group of cytochromoxidase) at 414±20 (extinction at maximum≈70), 439±20 (extinction at maximum≈117), 446±20 (extinction at maximum≈10), 534≈20 (extinction at maximum≈11), 598±20 (extinction at maximum≈16), 635±20 nm (extinction at maximum≈9), and cytoporphyrin at 415±20 (extinction at maximum≈160), 520≈20 (extinction at maximum≈9), 560±20 (extinction≈21), 580±20 (extinction at maximum≈11), 617±20, 646±20 nm (extinction at maximum≈1)). Cytoporphyrin, which is found in bacteria, is very photosensitive. Protoporphyrin IX contained in bacteria and fungi can be excited at the wavelengths: 410±20 (extinction at maximum≈270), 504±20 (extinction at maximum≈15), 556±20 (extinction at maximum≈15), 600±20 (extinction at maximum≈6), 631±20 nm (extinction at maximum≈5)

Molecular oxygen can be photoactivated at the wavelengths 580±20, 630±20, 760±20, 1060±20, and 1268±20 nm. Moderate hyperthermia provided by a heater up to 43° C. during a tooth cleaning procedure of 0.5-3 min in duration is also desirable to provide a synergetic effect on blood and lymph microcirculation.

Reduction of tooth hypersensitivity. Tooth sensitivity results mostly from the increased movement of fluid through the dentinal tubes toward nerve endings in the tooth due to osmotic pressure induced by drink and/or saliva components. Tooth hypersensitivity depends on enamel porosity caused by temporal or permanent enamel demineralization induced by a low value of the oral liquid pH. At more acidic pH of the oral liquid (4.0-5.0), the enamel permeability increases 3-4-fold. Therefore, the process of enamel light-induced remineralization will assist in the reduction of tooth hypersensitivity. Bacteria killing will also lead to reduction of tooth hypersensitivity due to pH normalization and less gingival swelling and less osmotic pressure applied to hypersensitive tooth compounds. Therefore, irradiation of a tooth surface at a power density of 1-1000 mW/cm$^2$ and a daily dose of 0.06-30 J/cm$^2$ at wavelengths corresponding to porphyrins, cytochromes, and molecular oxygen are preferred. Blue light (400-430 nm) is very effective for bacterial porphyrin excitation; green light (530-580 nm) and red light (600-700 nm) are also capable of activating porphyrins in bacteria and killing them via radical generation. Green (540-580 nm) and red (600-650 nm) light are capable of activating tooth pulp porphyrins and increasing blood and lymph microcirculation in pulp, with a corresponding increase in calcium ion flux from pulp to enamel through the protein matrix, which assists calcium ions to fill vacancies in hydroxyapatite structure. Molecular oxygen dissolved in tissues and tooth pulp can be photoactivated at the wavelengths 580±20, 630±20, 760±20, 1060±20, and 1268±20 nm. Moderate hyperthermia provided by a heater can also provide a synergetic effect on blood and lymph microcirculation. More effective bacteria killing can be accomplished by exogenous chromophore application and irradiation at wavelengths corresponding to the chromophore; in particular, for Methylene Blue (MB) dye at concentration of 0.01-1.0%, irradiation at 660±10 nm and power densities 5-1000 mW/cm$^2$; or for Indocyanine Green (ICG) dye at concentration of 0.01-1.0%, irradiation at 805±5 nm and power densities 5-1000 mW/cm$^2$.

Pain reduction in teeth is mostly due to improved pulpal blood and lymph microcirculation caused by dilatation of blood and/or lymph vessels induced by photo stimulated NO action on endothelial cells of vessel wall and by photo attenuated sympathetic vasomotor nerves activity. Direct light induced inhibition of nerve activity is also possible. Therefore, irradiation of a tooth surface at a power density of 1-1000 mW/cm$^2$ and a daily dose of 0.06-30 J/cm at the wavelengths corresponding to porphyrins, cytochromes, and molecular oxygen are needed. Green (530-580 nm) and red light (600-650 nm) are capable of activating tooth pulp porphyrins and increasing blood and lymph microcirculation in pulp. Molecular oxygen dissolved in tissues and tooth pulp can be photoactivated at the wavelengths 580±20, 630±20, 760±20, 1060±20, and 1268±20 nm. Moderate hyperthermia provided by an electrical heater (or LED radiation heating) up to 43° C. during a tooth cleaning procedure of 0.5-3 min in duration is desirable to get a synergetic effect on blood and lymph microcirculation.

Periodontal and bone regeneration and implant connection are mostly caused by increase in macrophage activity, in fibroblast, osteoblast, and odontoblast proliferation, induced by light and/or combined light and thermal action. Increased blood and lymph microcirculation also improves tissue growing and regeneration. Irradiation of teeth and periodontal tissue at power density of 1-1000 mW/cm² and daily dose of 0.06-30 J/cm² at the wavelengths corresponding to porphyrins, cytochromes, and molecular oxygen will produce radicals responsible for increased macrophage activity, increased fibroblast, osteoblast, and odontoblast proliferation, and increased blood and lymph micro-circulation. Blue light (400-430 nm) is very effective for porphyrin excitation; green light (530-580 nm) and red light (600-650 nm) are also capable of activating porphyrins. Green (530-580 nm) and red light (600-650 nm) are capable of activating tooth pulp porphyrins. Molecular oxygen can be photoactivated at the wavelengths 580±20, 630±20, 760±20, 1060±20, and 1268±20 nm. Moderate hyperthermia provided by a special heater (or LED current heating) up to 43° C. during a tooth cleaning procedure of 0.5-3 min in duration is desirable to obtain a synergetic effect in macrophage activity, in fibroblast, osteoblast, and odontoblast proliferation, and increased blood and lymph microcirculation.

Remineralization of enamel. Enamel demineralization is induced mostly by a low value of the oral liquid pH. Light and soft heating activates blood and lymph microcirculation of gingiva and therefore increases calcium ion flux from saliva to enamel through the protein matrix; ions of calcium fill vacancies in hydroxyapatite structure. Bacteria killing leads to pH normalization and therefore prevents enamel demineralization. Therefore, irradiation of a tooth surface at a power density of 1-1000 mW/cm² and a daily dose of 0.06-30 J/cm² at the wavelengths corresponding to porphyrins, cytochromes, and molecular oxygen are needed. Blue light (400-430 nm) is very effective for bacterial porphyrin excitation; green light (530-580 nm) and red light (600-650 nm) are also capable of activating porphyrins in bacteria and killing them via radical generation. Green (530-580 nm) and red light (600-650 nm) are capable of activating tooth pulp porphyrins and increasing blood and lymph microcirculation in pulp and a corresponding increase in calcium ion flux from pulp to enamel through the protein matrix, which assists calcium ions to fill vacancies in hydroxyapatite structure. Molecular oxygen dissolved in tissues and tooth pulp can be photoactivated at the wavelengths 580±20, 630±20, 760±20, 1060±20, and 1268±20 nm. Moderate hyperthermia provided by a special heater (or LED current heating) up to 43° C. during a tooth cleaning procedure of 0.5-3 min in duration is desirable to get a synergetic effect on blood and lymph microcirculation. Sonophoresis and/or electrophoresis will assist in increasing blood and lymph flow, and in smoother distribution of Ca and P elements within hard tooth tissue. More effective bacteria killing (if needed) can be achieved by exogenous chromophore application and irradiation at wavelengths corresponding to the chromophore; in particular, for Methylene Blue (MB) dye at concentration of 0.01-1.0%, irradiation at 660±10 nm and power densities 5-100 mW/cm²; or for Indocyanine Green (ICG) dye at concentration of 0.01-1.0%, irradiation at 805±5 nm and power densities 5-100 mW/cm².

Prevention of caries, which is usually caused mostly by Streptococcus mutants bacteria. Thus, bacteria killing via photodynamic effect induced by light and endogenous porphyrins, and/or cytochroms, and/or molecular oxygen, and/or exogenous dyes, and/or mineral photosensitizers, and/or mineral photocatalysts incorporated in the oral cavity, is a technique for caries prevention and healing. Light and thermal induced blood and lymph microcirculation in pulp and gingiva and increased calcium flux from saliva to enamel also prevents caries. Therefore, irradiation of a tooth surface at a power density of 1-1000 mW/cm² and a daily dose of 0.06-30 J/cm² at the wavelengths corresponding to porphyrins, cytochromes, and molecular oxygen are needed. Blue light (400-430 nm) is very effective for bacterial porphyrin excitation; green light (530-580 nm) and red light (600-650 nm) are also capable of activating porphyrins in bacteria and killing them via radical generation. Green (540-580 nm) and red light (600-650 nm) are capable of activating tooth pulp porphyrins and increasing blood and lymph microcirculation in pulp and a corresponding increase in calcium ion flux from pulp to enamel through the protein matrix, which assists calcium ions to fill vacancies in hydroxyapatite structure. Molecular oxygen dissolved in tissues and tooth pulp can be photoactivated at the wavelengths 580±20, 630±20, 760±20, 1060±20, and 1268±20 nm. Moderate hyperthermia provided by a special heater (or LED current heating) up to 43° C. during a tooth cleaning procedure of 0.5-3 min in duration is desirable to get a synergetic effect on blood and lymph microcirculation. Sonophoresis, and/or electrophoresis will assist in increasing blood and lymph flow, and in smoother distribution of Ca and P elements within hard tooth tissue. More effective bacteria killing (if needed) can be achieved by exogenous chromophore application and irradiation at wavelengths corresponding to the chromophore; in particular, for Methylene Blue (MB) dye at concentration of 0.01-1.0%, irradiation at 660±10 nm and power densities 5-100 mW/cm²; or for Indocyanine Green (ICG) dye at concentration of 0.01-1.0%, irradiation at 805±5 nm and power densities 5-100 mW/cm². Very effective and nonspecific singlet oxy-gen and other radical production can be provided at broadband (300-900 nm) excitation of carbon nanoparticles or nanotubes, like carbon black, fullerene, or tubulene, and/or at application of a photocatalyst, like $TiO^2$ nanoparticles, in mixture with MB and/or ICG dyes.

Root canal sterilization and inflammation prevention also can be realized by pholodynamic effect induced by light and endogenous porphyrins, in particular Protoporphyrin IX, and/or molecular oxygen, and/or exogenous dyes incorporated in tooth pulp via local blood and lymph micro-circulation. Due to waveguide propagation, light is concentrated in the tooth pulp, and therefore enhances photodynamic efficiency and activates pulp blood and lymph microcirculation. Light also improves immunocompetence of macrophages, which produce SO and NO responsible for host defense against microorganisms. Therefore, irradiation of a tooth surface at a power density of 1-1000 mW/cm² and a daily dose of 0.06-30 J/cm² at the wavelengths corresponding to porphyrins, cytochromes, and molecular oxygen are needed. Green (540-580 nm) and red (600-650 nm) light are capable of activating tooth pulp porphyrins to produce radicals for bacteria killing, improvement of macrophage immunocompetence, and increased blood and lymph micro-circulation in pulp. Molecular oxygen dissolved in tissues and tooth pulp can be photoactivated at the wavelengths 580±20, 630±20, 760±20, 106±20, and 1268±20 nm. Moderate hyperthermia provided by a special heater (or LED current heating) up to 43° C. during a tooth cleaning procedure of 0.5-3 min in duration is desirable to get a synergetic effect on blood and lymph microcirculation. Sonophoresis and/or electrophoresis will assist in increase of blood and lymph flow. The light which penetrates to the root canal and apex area can prevent or decrease inflammation associated with bacteria growth Periodontal problem prevention and healing is also due to the lethal effect of light on bacteria via excitation of endogenous porphyrins, and/or molecular oxygen, and/or exogenous dyes, and/or mineral photosensitizers, and/or mineral photocatalysts incorporated in the periodontal lesions via production of active (singlet) oxygen and other radicals. Light also improves immunocompetence of macrophages, which produce SO and NO responsible for host defense against microorganisms. Light and soft heating activate blood and lymph microcirculation and therefore activate endotheliocytes proliferative potency and formation of new capillary net that helps to keep gingiva attached to the teeth. Therefore, light power densities, daily doses, and wavelengths are the same as used for prevention of caries (see, Prevention of caries).

Soft Tissue Treatments:

Another advantage of the sensor-responsive toothbrushes of the present invention is that they allow directional radiating. In some cases discussed below it is desirable to optically radiate primarily soft tissue such as tongue tissue, nerve tissue, throat tissue, vascular tissue, hair follicles, sebaceous follicles, sebaceous glands, facial subcutaneous fat, facial muscular tissue, lymph systems, collagen, pigmented spots, and/or other tissue including other facial tissue and other oral tissue. The toothbrushes allow for directing radiation toward these tissue areas by choosing the direction in which the optical radiation is emitted. For example, to radiate facial tissue, the optical radiation source can be positioned on the outer perimeter of a light-emitting toothbrush. Unlike conventional toothbrushes which only radiate in the direction of the bristle (toward the hard tissue of the teeth), the radiation provided by these sensor-responsive toothbrushes can be directed such that the emitted radiation penetrates the mucosal lining of the oral cavity to deliver phototherapy to a region within the user's soft facial tissue.

In addition, the sensor-responsive toothbrushes of the present invention allow certain conditions, which had in the past been treated from outside the oral cavity, to be treated by employing an optical radiation source from within the oral cavity. For example, instead of treating acne by radiating the effected skin, the toothbrushes can directly radiate from within the oral cavity out toward the target tissue. This is advantageous because the tissue within the oral cavity is easier to penetrate due to the limited amount of collagen contained in the tissue walls of the oral cavity. As a result, optical energy more easily penetrates tissue to provide treatment at a lower level of energy and reduce the risk of tissue damage. Preferable range of wavelength for this type of treatment is in the range of about 280 nm to 1400 nm and even more preferably in the range of about 590 nm-1300 nm.

Improvement of oral mucus inflammatory disease (stomatitis—superficial erosions and fissuring at the angle of the mouth, an acute infection of the oral mucosa with vesicle formation, due to the herpes simplex virus, stomatitis with shallow ulcers on the cheeks, tongue, and lips) due to lethal effect of light on viruses and bacteria via excitation of endogenous porphyrins, and/or molecular oxygen, and/or exogenous dyes, and/or mineral photosensitizers, and/or mineral photocatalysts incorporated in the oral mucus lesions via production of active (singlet) oxygen and other radicals. Light also improves immunocompetence of macrophages, which produce SO and NO responsible for host defense against microorganisms. Light and soft heating activate blood and lymph microcirculation and therefore activate epithelial cell proliferative potency. Light power densities, daily doses, and wavelengths are the same as used for prevention of caries (see, Prevention of caries).

Tongue diseases (black tongue—the presence of a brown fur-like patch on the dorsum of the tongue, composed of hypertrophied filiform papillae with microorganisms and some pigment; coated tongue—one covered with a whitish or yellowish layer consisting of desquamated epithelium, debris, bacteria, fungi, etc.) improvement due to lethal effect of light on microorganisms via excitation of endogenous porphyrins, and/or molecular oxygen, and/or exogenous dyes, and/or mineral photosensitizers, and/or mineral photocatalysts incorporated in the tongue lesions via production of active (singlet) oxygen and other radicals. Light also improves immunocompetence of macrophages, which produce SO and NO responsible for host defense against microorganisms. Light and soft heating activate blood and lymph microcirculation and therefore activate epithelial cell proliferative potency. Light power densities, daily doses, and wavelengths are the same as used for prevention of caries (see, Prevention of caries).

Recovery from inflammation of salivary glands and small sublingual ducts, which open into the mouth on the sublingual fold (ducts of Rivinus). The same mechanisms of recovery as for stomatitis and tongue lesions are expected. Light power densities, daily doses, and wavelengths are the same as used for prevention of caries (see, Prevention of caries).

Pain reduction in oral tissue results mostly from improved blood and lymph microcirculation caused by dilatation of blood and/or lymph vessels induced by photo stimulated NO action on endothelial cells of vessel wall and by photo attenuated sympathetic vasomotor nerves activity. Direct light induced inhibition of nerve activity is also possible. Light power densities, daily doses, and wavelengths are the same as used for dental pain reduction (see, Pain reduction in teeth).

Improvement of sore throat, angina, acute or chronic tonsillitis, etc. caused mostly by growth of Staphylococcus aureus bacteria (tonsillitis inflammation of tonsils, especially the palatine tonsils; follicular tonsillitis, tonsillitis especially affecting the crypts; parencbymatous tonsillitis; acute tonsillitis, that affecting whole substance of the tonsil; pustular tonsillitis, a variety characterized by formation of pustules). Such improvement is due to lethal effect of light on bacteria via excitation of endogenous porphyrins, and/or molecular oxygen, and/or exogenous dyes, and/or mineral photosensitizers, and/or mineral photocatalysts incorporated in tonsil lesions via production of active (singlet) oxygen and other radicals. Light also improves immunocompetence of macrophages, which produce SO and NO responsible for host defense against microorganisms. Light and soft heating activate blood and lymph microcirculation and therefore activate epithelial cell proliferative potency. Light power densities, daily doses, and wavelengths are the same as used for prevention of caries. ALA related treatment with low concentration of ALA, an inductor of porphyrins in proliferating cells, at 620-640 nm excitation can be used for suppression of abnormal proliferation or oral mucous epithelial cells, glands growing, microbial colonies within oral tissues (gingival, glands, tongue, throat, etc). In particular, treatment of pharyngomycosis can be provided.

Sinusitis caused mostly by Streptococcus pneumoniae bacteria. The same mechanisms of recovery as for angina and tonsillitis. Light power densities, daily doses, and wavelengths are the same as used for prevention of caries (see, Prevention of caries).

Recovery from laryngitis and other inflammations of the vocal cords. The same mechanisms of recovery as for angina, tensilities, and sinusities. Light power densities, daily doses, and wavelengths are the same as used for prevention of caries (see, Prevention of caries).

Improvement of skin texture, elasticity, as well as wrinkle reduction (i.e., skin rejuvenation) around lips and cheeks via increased macrophage and fibroblast proliferation activities and new collagen production induced by light and/or combined light and thermal action. Increased blood and lymph microcirculation also improves tissue growth and regeneration. Light power densities, daily doses, and wavelengths are the same as used for periodontal and bone regeneration and implant connection (see, Periodontal and bone regeneration and implant connection).

Improvement of acne. Due to high penetration depth of red light, it is possible to provide needed irradiation dose to sebaceous glands through cheek tissues for a lethal light effect on acne causing bacteria concentrated within the sebaceous glands. The light excitation of bacteria porphyrins will generate active (singlet) oxygen and other radicals which selectively kill these bacteria. Therefore, irradiation of cheeks inside the oral cavity at a power density of 1-1000 mW/cm$^2$ and a daily dose of 0.06-30 J/cm$^2$ at the wavelengths corresponding to bacterial porphyrins is desirable. Green (530-580 nm) and red light (600-650 nm) can penetrate through cheek tissue and activate acne bacterial porphyrins to produce radicals which kill bacteria. The acne treatment efficiency can be enhanced by application of an appropriate photosensitizer (e.g., methylene blue, indocya-nine green, ALA, etc) to the acne lesion in combination with utilizing red and/or NIR radiation.

Hair growth control can be provided by normalization of blood and lymph microcirculation within hair follicles by light, and/or combined light and thermal action. Irradiation of oral cavity tissues at a power density of 1-1000 mW/cm$^2$ and a daily dose of 0.06-30 J/cm$^2$ at the wavelengths corresponding to porphyrins, cytochromes, and molecular oxygen will produce radicals responsible for vessel dilatation and corresponding increase of blood and lymph microcirculation. Green (530-580 nm) and red light (600-650 nm) penetrate through cheek tissue and activate porphyrins and cytochromes. Molecular oxygen can be photoactivated at the wavelengths 580±20, 630±20, 760±20, 1060±20, and 1268±20 nm. Moderate hyperthermia provided by a special heater (or LED current heating) up to 43° C. during a tooth cleaning procedure of 0.5-3 min in duration is desirable to get a synergetic effect in increase of blood and lymph microcirculation. Hair growth control can, for example, includes hair removal or reduction by selective destruction of multiple hair follicles using a single or time-dependent sequence of radiation.

Vascular improvement can be associated with increased macrophage and fibroblast proliferation activities and new collagen and epithelium production induced by light and/or combined light and thermal action. Irradiation of oral cavity tissues at a power density of 1-1000 mW/cm$^2$ and a daily dose of 0.06-30 J/cm$^2$ at the wavelengths corresponding to porphyrins, cytochromes, and molecular oxygen will produce radicals responsible for increase in macrophage activity, fibroblast proliferation, and collagen growth. Green (530-580 nm) and red light (600-650 nm) penetrate through cheek tissue and activate tissue porphyrins and cytochroms. Molecular oxygen can be photoactivated at the wavelengths 580±20, 630±20, 760±20, 1060±20, and 1268±20 nm. Moderate hyperthermia provided by a special heater (or LED current heating) up to 43° C. during a procedure of 0.5-3 min in duration is desirable to get a synergetic effect in macrophage activity, fibroblast proliferation, and collagen growth.

Perioral dermatitis treatment is due to light improved immunocompetence of macrophages, and light activated blood and lymph microcirculation caused epidermal cell proliferative potency. Irradiation of oral cavity tissue at a power density of 1-1000 mW/cm$^2$ and a daily dose of 0.06-30 J/cm$^2$ at the wavelengths corresponding to porphyrins, cytochromes, and molecular oxygen will produce radicals responsible for increased macrophage activity and increased blood and lymph microcirculation. Green (530-580 nm) and red light (600-650 nm) penetrate through cheek tissue and activate porphyrins and cytochroms. Molecular oxygen can be photoactivated at the wavelengths 580±20, 630±20, 760±20, 1060±20, and 1268±20 nm. Moderate hyperthermia provided by a special heater (or LED current heating) up to 43° C. during a procedure of 0.5-3 min in duration is desirable to get a synergetic effect in macrophage activity and increase of blood and lymph microcirculation.

Repair of damaged trigeminal facial nerve peripheral receptors in the oral cavity tissues, including gingiva, teeth, lips, and tongue, and other nerves controlling oral tissue functioning, can be caused by Ca$^{2+}$ storage in neural cell mitochondria and followed activation of Ca$^{2+}$-dependent ATPase in these cells. Increase of blood and lymph microcirculation induced by light and/or combined light and thermal action also should be important for neural tissue regeneration. Light power densities, daily doses, and wavelengths are the same as used for perioral dermatitis treatment.

Pain reduction in oral tissue results mostly from improved blood and lymph microcirculation caused by dilatation of blood and/or lymph vessels induced by photo stimulated NO action on endothelial cells of vessel wall and by photo attenuated sympathetic vasomotor nerve activity. Direct light induced inhibition of nerve activity is also possible. The following nerves may be involved in the process: buccal nerve which innervate oral mucosa and cheek skin at the mouth nook; inferior and superior alveolar nerves which innervate teeth, periosteum and gingiva; glos-sopharyngeal, hypoglossal, and lingual nerves, which innervate gullet, tongue and chin-tongue muscles, and oral cavity bottom mucosa; inferior, recurrens, and superior laryngeal nerves which innervates gullet muscles and mucosa; mas-seteric nerve which innervates masticatory muscle. Light power densities, daily doses, and wavelengths arc the same as used for dental pain reduction.

Beneficial influence on human organism immuno-competence, in particular by light improved immunocompetence of blood and lymph macrophages, which produce superoxide and nitric oxide; erythrocytes membrane elasticity and lymphocyte proliferation activity. Light acceptors are endogenous porphyrins, cytochrorns, and molecular oxygen. Therefore, irradiation of oral mucus and underlying tissue, well supplied by blood vessels, should be at power density of 1-1000 mW/cm$^2$, daily doses of 0.06-30 J/cm$^2$ and at the wavelengths corresponding to porphyrins, cytochromes, and molecular oxygen. Blue light (400-430 nm) is very effective for porphyrins excitation; green light (530-580 nm) and red light (600-650 nm) are also capable to activate porphyrins. In particular, coproporphyrins can be excited at the wavelengths: 402±20 (extinction at maximum≈480), 495±20, 540±30 (extinction at maximum≈17), 580±30 (extinction at maximum≈6), 623±20 nm; and cytochroms: cytogem at 414±20 (extinction at maximum≈70), 430±20 (extinction at maximum≈117), 446±20 (extinction maximum≈10), 534±20 (extinction at maximum≈11), 598±20 (extinction at maximum≈46), 635±20 nm (extinction at maximum≈9), and cytoporphyrin (porphyrin a) at 415±20 (extinction at maximum≈160), 520±20 (extinction at maximum≈9), 569±20 (extinction≈21), 580±20 (extinction at maximum 11), 617±20, 646±20 nm (extinction at maximum≈1). Protoporphyrin IX can be excited at the wavelengths: 410±20 (extinction at maximum≈270), 504±20 (extinction at maximum≈15), 556±20 (extinction at maximum≈15), 600±20 (extinction at maximum≈6), 631±20 nm (extinction at maximum≈5) Molecular oxygen can be photoactivated at the wavelengths 580±20, 630±20, 760±20, 1060±20, and 1268±20 nm.

Control of circadian rhythms. Blue light at 470 nm affects the circadian rhythms of humans and might be applicable to anyone who has biological rhythms disorder. The possible light acceptors are blood bilirubin and/or coproporphyrins. Light irradiation of oral mucus and underlining tissue, well supplied by blood vessels, is desirably at power density of 1-1000 mW/cm$^2$, one-day dose of 0.06-30 J/cm$^2$ and wavelengths corresponding to bilirubin absorption (455±20 nm) and/or Coproporphyrins I and III absorption (402±20, 470±20, 540±30, 580±30, 623±20 nm). In some embodiments of the invention, a light-emitting toothbrush is provided that can be utilized to irradiate the user's oral cavity in the morning with radiation having a selected wavelength, e.g., blue light (or other biostimulating light), and to irradiate the oral cavity in the evening with radiation having another wavelength, e.g., red light (or light having a sedative effect), so as to help regulate the user's circadian cycle.

Controllable destruction of metabolic components of blood, in particular bilirubin, appearing in the blood stream due to normal or pathological decay of erythrocytes, allows for prevention of such diseases as bilirubinemia. Light irradiation of oral mucus and underlining tissue, well supplied by blood vessels at 450-460 nm with power density of 1-1000 mW/cm$^2$ and one-day dose of 0.06-30 J/cm$^2$ is preferable.

Killing viruses within the blood microcirculatory system via photodynamic effect by topical application (e.g., to oral mucous) or intravenous injection of an appropriate photodynamic agent like ALA, hematoporphyrin, etc. Light irradiation of oral mucus and underlining tissue, well supplied by blood vessels, for this treatment should be preferably at a power density of 1-1000 mW/cm$^2$, one-day dose of 0.06-30 J/cm$^2$ and wavelengths corresponding to absorption spectra of the photodynamic agent which is used. For ALA application, these wavelengths correspond to absorption bands of Protoporphyrin IX (409±20, 503±20, 538±20, 555±20, 576±20, 600±20, 632±20 nm); while for Hematoporphyrin derivatives (HPD) the wavelength is 620±20 nm.

Diseases of the lip can also be treated light and/or combined light and thermal action. Irradiation of oral cavity tissues at a power density of 1-1000 mW/cm$^2$ and a daily dose of 0.06-30 J/cm$^2$ at the wavelengths corresponding to porphyrins, cytochromes, and molecular oxygen will produce radicals responsible for increase in macrophage activity, fibroblast proliferation, and collagen growth. Green (530-580 nm) and red light (600-650 nm) penetrate through cheek tissue and activate tissue porphyrins and cytochroms. Molecular oxygen can be photoactivated at the wavelengths 580±20, 630±20, 760±20, 1060±20, and 1268±20 nm. Moderate hyperthernia provided by a special heater (or LED current heating) up to 43° C. during a procedure of 0.5-3 min in duration is desirable to get a synergetic effect in macrophage activity, fibroblast proliferation, and collagen growth.

Drug delivery. Radiating soft tissue within the oral cavity, and particularly the area under the tongue, can improve the efficiency of drug delivery into the blood stream. The optical radiation creates NO species which in turn causes blood vessel to dilate and can thereby increase the absorption rate and efficiency of pharmaceutical agents placed on the tissue surface. In one embodiment a drug is placed under the tongue and optical radiation is directed toward the adjacent soft tissue. Another more complex drug delivery involves in situ activation of chemical therapeutic components, which in an inactive state can readily diffuse into the oral cavity tissue, by radiation. For example, such agents in an inactive form can be administered to a patient's oral cavity tissue followed by activation via irradiation at a selected wavelength.

Another use for the sensor-responsive toothbrushes oral appliances of the present invention is tooth whitening and brightening. All current tooth whitening technologies are based on chemical bleaching effects of peroxides. Tooth color is defined by its structure and optical properties of acquired pellicle, enamel, dentin. All these components are generally responsible for presenting a stained appearance. Cosmetic appearance of the tooth depends on reflection from enamel and dentine. Extrinsic and/or intrinsic staining results in tooth color. Usually, compounds such as tannins, other food pigments, and poly-phenolic components of smoke which become trapped in and tightly bounded to the proteinaceous layer on the surface of the teeth cause extrinsic staining of the acquired pellicle, and typically can be removed mechanically using a toothbrush. Natural color of a tooth is determined by the light scattering and absorption properties of dentine and enamel-dentine junction. With aging, many proteins, including collagen, contained in dentin become more yellowish due to changes in molecular structure. Such age-dependent coloration is an example of intrinsic coloration. For heavy smokers, coffee drinkers and red wine drinkers, food colorants may penetrate in tooth depth, in enamel and even dentin, and therefore could not be removed by mechanical cleaning, and should be considered as intrinsic. Some systematic lesions caused by a surplus of fluorine in drinking water or by prolonged usage of tetracycline are other examples of intrinsic colorants. To bleach intrinsic tooth stains, chemical methods, based on oxidation or enzymes application are usually used.

Use of optical radiation from the sensor-responsive toothbrushes of the present invention can provide effective tooth whitening and brightening. An additional benefit from using a light-emitting toothbrush can be concurrent prophylaxis and/or treatment in the user's home of periodontal disease, caries and other oral diseases, which are based mostly on effective bacteria killing and lesion healing.

The sensor-responsive toothbrush can provide optical teeth whitening and brightening based on the following exemplary mechanisms of color centers bleaching in enamel and dentin: 1) short wavelength (300-500 nm) direct photobleaching; 2) wavelengths in the range 960±20 nm, and/or 1200-12000 nm, more preferably 1450±150 nm, and/or 1890±250 nm and/or 2400-3200 nm; 9000-12000 nm are used for photo thermal bleaching; and 3) direct photo and photochemical production of singlet oxygen within enamel and dentin using light absorption by oxygen in tissue at 580±20, 630±20, 760±20, 1060±20, and 1268±20 nm, and/or light absorption at selective wavelengths in the range 300-900 nm corresponding to absorption bands of a photosensitizer due to a photodynamic effect upon endogenous and/or externally applied ghotosensitizers and/or photocatalysts (FDA approved dyes, and/or carbon black (graft copolymers), fullerenes (carbon nanoparticles), and/or tubulenes (carbon nanotubes), and/or $TiO^2$ nanoparticles).

In one aspect, the present invention directs radiation deep into the tooth to treat intrinsic stains in the dentine structure and the pulp. In some embodiments, a sensor-responsive toothbrush of the present invention optically radiates stains within the dentine. One of the main advantage of this invention is the possibility to produce active radicals like singlet oxygen not only on the tooth surface, but also depth in hard tissue (enamel and dentin), and therefore effectively bleach intrinsic colorants. The waveguiding (photonic crystal) structure of dentin gives the possibility to concentrate light within narrow dentin tubules (1-5 microns in diameter) filled by water and odontoblast surrounded by organic (collagen)

materials. The specific feature of this invention to bleach bulky light absorbers provides not only tooth whitening, but also tooth brightening due to a decrease in bulk absorption of light and an increase in back scattering. Photobiostimulation can also be employed to cause new dentine growth by radiation targeting of odonoplast and pulp, thereby enhancing cosmetic appearance of deep tooth structure. Further, utilizing low dose radiation every day can cause tooth rejuvenation.

In another embodiment, the sensor-responsive toothbrush of the present invention is used to irradiate teeth so as to reduce staining within the dentine and the enamel; the teeth are thereby whitened and brightened. In one embodiment, teeth are optically radiated with radiation in the wavelength band between approximately 300 and 1350 nm. The toothbrush can also include a mechanical vibrator for better cleaning, and/or electrodes for electrophoresis of the photosensitizer. In addition, a photodetector and a microchip for detection of reflected and/or fluorescent light from enamel can be used to monitor tooth color.

Heating with electrical heaters or with radiation in the wavelength range above about 800 nm to about 100,000 nm (100 microns) can be used to facilitate whitening and brightening. The use of optical radiation is particularly advantageous because it allow for deep, selective heating. By choosing an appropriate wavelength, the tooth can be heated to a predetermined depth and color centers can be destroyed and removed from enamel due to thermally induce bleaching and diffusion. The stain will diffuse out of the tooth and can be dissolved in saliva or saline (if present). Preferred wavelength ranges include 960±20 nm, and/or 1200-100,000 nm; more preferably 1450±150 nm, and/or 1890±250 nm and/or 2400-3200 nm.

The sensor-responsive toothbrushes of the present invention can also directly photobleach teeth using only intrinsic light absorbers. Alternatively, the exogenous chromophores discussed above can be use to improve the effectiveness of tooth whitening and brightening. The chromophores (and other treatment agents) can be applied to teeth and then the teeth irradiated.

In another embodiment, dentine stains can be selectively photobleached by direct optical radiation within the absorption range of the stain. Unlike conventional tooth whitening, the present invention allows a user to use select wavelength ranges centered around the absorption spectrum of the stain, which can be in a range of about 280 to about 800 nm. The result is whitening and brightening with a very specific wavelength band.

In another aspect of the invention, biostimulating and/or dental phototherapies are disclosed for conditions that are normally responsive to a known power density of phototherapeutic radiation (1-10 treatments spaced 1-30 days). However, in the present invention a series of temporally spaced treatment sessions are delivered to a patient, where each session provides a power density of therapeutic radiation lower than typical power density needed to treat the condition according to the conventional protocols. The method can comprise the steps of selecting a condition normally responsive to oral application of a known power density of phototherapeutic radiation, and delivering a series of temporally spaced treatment sessions to a patient. Each session provides a power density of therapeutic radiation lower than the typical power density needed to treat the patient condition. The series of temporally spaced treatment sessions can be continued until the patient's condition is ameliorated by a cumulative effect of the series of treatment sessions. The power density applied to the patient's skin surface is between approximately 1 mW/cm$^2$ and approximately 100 W/cm$^2$, and depends at least on the condition being treated and the wavelength of the radiation. Preferably, the energy at the tooth or muscosal surface is between 10 mW/cm$^2$ and 10 W/cm$^2$. The radiation can be applied for a duration of one second to one hour. Energy flux can be in the range of about 1 J/cm$^2$ to 1000 J/cm$^2$, and preferably in the range of about 10 J/cm$^2$ to 100 J/cm$^2$. In many embodiments, an emitting area of an LETM or LEMP can be in a range of about 0.1 to about 100 cm$^2$ and the power delivered is in a range of about 1 mW to about 10 W, and preferably in a range of about 10 mW to about 1 W. This power can be delivered by employing highly efficient light sources, such as those described above, with power supplies that can be as small as a batter, or wall plug power supplies.

It is significant to note that any of the features, aspects, or details of an embodiment described herein can be combined, either entirely or partially, with any other feature, aspect, or detail of one or more other embodiments described herein. For example, the present invention sensor-responsive toothbrush can include (1) one or more sensors such as for example (i) one or more sensor input elements, (ii) one or more sensor output elements, or combinations of these elements in combination with (2) one or more outputs such as (i) one or a plurality of mechanical outputs, (ii) one or a plurality of light-based outputs, (iii) one or a plurality of chemical-based outputs, or (iv) combinations of any of these outputs. The resulting sensor-responsive toothbrush can be provided in conjunction with a kit and/or be provided with one or more replaceable head or neck assemblies.

Moreover, although the present invention sensor-responsive toothbrushes have been primarily described in conjunction with an electric toothbrush having a powered moveable bristle assembly, the invention includes oral care instruments that do not use powered bristles. For example, the present invention includes a manual toothbrush having one or more sensors as described herein in conjunction with one or more outputs as also described herein. In certain embodiments, it is also contemplated that the present invention includes non-toothbrush oral appliances or instruments.

The following patent applications and patents provide further details as to various aspects of the sensor-responsive toothbrushes described herein. U.S. application Ser. No. 60/501,266 filed on Sep. 9, 2003; U.S. application Ser. No. 10/832,168 filed on Apr. 26, 2004; U.S. application Ser. No. 10/847,429 filed on May 17, 2004; U.S. application Ser. No. 10/842,302 filed on May 10, 2004; U.S. application Ser. No. 10/887,644 filed on Jul. 9, 2004; U.S. application Ser. No. 10/887,667 filed on Jul. 9, 2004; U.S. application Ser. No. 10/888,206 filed on Jul. 9, 2004; U.S. published application US 2004/0191729A1 filed on Feb. 10, 2004; U.S. published application US 2004/0193235A1 filed on Feb. 10, 2004; U.S. published application US 2004/0193236A1 filed on Feb. 10, 2004; U.S. published application 2004/0199227A1 filed on Feb. 10, 2004; U.S. published application US 2004/0204745A1 filed on Feb. 10, 2004; U.S. published application US 2004/0210276A1 filed on Feb. 10, 2004; and U.S. Pat. No. 6,648,904.

Further aspects, details, and variant designs relating to the sensor-responsive toothbrushes described herein are set forth in U.S. Pat. Nos. 3,624,219; 4,066,745; 4,834,969; 5,057,308; 5,057,309; 5,057,310; 5,082,444; 5,095,615; 5,096,699; 6,214,320; and 6,509,007. Published U.S. applications that may also contain similar information include 2001/0002994; 2003/0082113; 2003/0190292; and 2004/0014001. Also, European publication No. EP 1104669 can also include relevant information.

All documents cited herein are, in relevant part, incorporated herein by reference; the citation of any document is not to be construed as an admission that it is prior art with respect to the present invention.

While particular embodiment of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sensor-responsive toothbrush comprising:
    a handle, a head, and a neck extending between the handle and the head, the handle having a hollow interior region, the head having bristles disposed thereon, and the toothbrush having a longitudinal axis;
    a sensor disposed on the toothbrush;
    a sensor filter;
    at least one movable bristle holder disposed on the head, the at least one movable bristle holder having a plurality of bristles disposed thereon;
    a motor disposed in the hollow interior region, wherein the motor is operatively connected to the at least one movable bristle holder to move the at least one bristle holder; and
    at least one output component in association with the sensor, wherein the at least one output component provides, in response to a sensor input, an output selected from the group consisting of a chemical-based output, a combination of a mechanical based output and a chemical based output, and a combination of a light based output and a chemical based output
    wherein the chemical-based output comprises dispensing an oral care composition.

2. The sensor-responsive toothbrush of claim 1, wherein the component associated with the sensor output emits light of a first wavelength, and the sensor input detects light of a second wavelength different than the first wavelength.

3. The sensor-responsive toothbrush of claim 1, wherein the plurality of bristles are moveable, and the mechanical based output comprises movement of the plurality of bristles or changing aspects of the movement.

4. The sensor-responsive toothbrush of claim 1 wherein the light-based output comprises generating heat.

5. The sensor responsive toothbrush of claim 1, wherein the light based output is a first light-emitting element.

6. The sensor responsive toothbrush of claim 5, wherein the toothbrush further comprises a second light-emitting element disposed on a bristle-bearing surface of the head of the toothbrush.

* * * * *